(12) United States Patent
Doty

(10) Patent No.: US 7,799,080 B2
(45) Date of Patent: Sep. 21, 2010

(54) SPINAL DISC PROSTHESIS AND METHODS OF USE

(76) Inventor: Keith L. Doty, 316 NW. 17th St., Gainesville, FL (US) 32603-1615

(*) Notice: Subject to any disclaimer, the term of this patent is extended or adjusted under 35 U.S.C. 154(b) by 855 days.

(21) Appl. No.: 11/540,620

(22) Filed: Sep. 29, 2006

(65) Prior Publication Data

US 2007/0021836 A1    Jan. 25, 2007

Related U.S. Application Data

(63) Continuation-in-part of application No. 11/112,832, filed on Apr. 22, 2005, now Pat. No. 7,361,192.

(51) Int. Cl.
*A61F 2/44* (2006.01)
(52) U.S. Cl. ............. 623/17.13; 623/17.12; 623/17.15
(58) Field of Classification Search ... 623/17.11–17.16; 403/53, 57, 62
See application file for complete search history.

(56) References Cited

U.S. PATENT DOCUMENTS

| | | |
|---|---|---|
| 4,309,777 A | 1/1982 | Patil |
| 4,394,921 A | 7/1983 | Miskinis |
| 4,595,663 A | 6/1986 | Krohn et al. |
| RE32,449 E | 6/1987 | Clausen et al. |
| 4,714,469 A | 12/1987 | Kenna |
| 4,759,766 A | 7/1988 | Buettner-Jantz et al. |
| 4,759,769 A | 7/1988 | Hedman et al. |
| 4,846,840 A | 7/1989 | Leclerq et al. |
| 4,863,476 A | 9/1989 | Shepperd |
| 4,911,718 A | 3/1990 | Lee et al. |
| 4,932,975 A | 6/1990 | Main et al. |
| 4,936,848 A | 6/1990 | Bagby |
| 4,947,378 A | 8/1990 | Jinbo et al. |
| 4,961,740 A | 10/1990 | Ray et al. |
| 4,997,432 A | 3/1991 | Keller |
| 5,002,576 A | 3/1991 | Furhmann et al. |
| 5,024,670 A | 6/1991 | Smith et al. |
| 5,037,438 A | 8/1991 | Davidson |
| 5,047,055 A | 9/1991 | Bao et al. |
| 5,071,437 A | 12/1991 | Steffee |

(Continued)

FOREIGN PATENT DOCUMENTS

DE    2263842    7/1974

(Continued)

OTHER PUBLICATIONS

Bao, Q.-B. et al. "Artificial Disc Technology" *Neurosurg Focus*, 2000, vol. 9, No. 4.

(Continued)

*Primary Examiner*—Thomas C Barrett
*Assistant Examiner*—Andrew Yang
(74) *Attorney, Agent, or Firm*—Saliwanchik, Lloyd & Saliwanchik

(57) ABSTRACT

Spinal disc prosthetic devices are provided having up to six-degrees-of-freedom with three rotational and three translational degrees-of-freedom within the entire workspace of a Functional Spinal Unit (FSU). Certain embodiments of the prosthetic disc mechanisms attach to upper and lower plates anchored between vertebrae of an FSU allowing modularity of the devices. Scaling, conjoined mechanical programmability allow the devices to realize almost any nominal required spinal articulation, from the cervical to lumbar regions.

64 Claims, 47 Drawing Sheets

U.S. PATENT DOCUMENTS

| | | | |
|---|---|---|---|
| 5,080,675 A | 1/1992 | Lawes et al. | |
| 5,258,031 A | 11/1993 | Salib et al. | |
| 5,258,043 A | 11/1993 | Stone | |
| 5,306,307 A | 4/1994 | Senter et al. | |
| 5,306,308 A | 4/1994 | Gorss et al. | |
| 5,306,309 A | 4/1994 | Wagner et al. | |
| 5,306,412 A | 4/1994 | Whitehouse et al. | |
| 5,314,477 A | 5/1994 | Marnay | |
| 5,314,478 A | 5/1994 | Oka et al. | |
| 5,320,644 A | 6/1994 | Baumgartner | |
| 5,401,269 A | 3/1995 | Buettner-Jantz et al. | |
| 5,415,704 A | 5/1995 | Davidson | |
| 5,425,773 A | 6/1995 | Boyd et al. | |
| 5,458,642 A | 10/1995 | Beer et al. | |
| 5,562,738 A | 10/1996 | Boyd et al. | |
| 5,674,296 A | 10/1997 | Bryan et al. | |
| 5,676,701 A | 10/1997 | Yuan et al. | |
| 5,782,832 A | 7/1998 | Larsen et al. | |
| 5,827,328 A | 10/1998 | Buttermann | |
| 5,865,846 A | 2/1999 | Bryan et al. | |
| 6,001,130 A | 12/1999 | Bryan et al. | |
| 6,019,792 A | 2/2000 | Cauthen | |
| 6,136,031 A | 10/2000 | Middleton | |
| 6,156,067 A | 12/2000 | Bryan et al. | |
| 6,179,874 B1 | 1/2001 | Cauthen | |
| 6,296,664 B1 | 10/2001 | Middleton | |
| 6,315,797 B1 | 11/2001 | Middleton | |
| 6,348,071 B1 | 2/2002 | Steffee et al. | |
| 6,368,350 B1 | 4/2002 | Erickson et al. | |
| 6,375,682 B1 | 4/2002 | Fleischmann et al. | |
| 6,395,032 B1 | 5/2002 | Gauchet | |
| 6,419,706 B1 | 7/2002 | Graf | |
| 6,458,159 B1 | 10/2002 | Thalgott | |
| 6,520,996 B1 | 2/2003 | Manasas et al. | |
| 6,572,653 B1 | 6/2003 | Simonson | |
| 6,579,321 B1 | 6/2003 | Gordon et al. | |
| 6,626,943 B2 | 9/2003 | Eberlein et al. | |
| 6,645,248 B2 | 11/2003 | Casutt | |
| 6,656,224 B2 | 12/2003 | Middleton | |
| 6,669,732 B2 | 12/2003 | Serhan et al. | |
| 6,733,532 B1 | 5/2004 | Gauchet et al. | |
| 6,736,850 B2 | 5/2004 | Davis | |
| 6,749,635 B1 | 6/2004 | Bryan | |
| 6,770,095 B2 | 8/2004 | Grinberg et al. | |
| 6,802,867 B2 | 10/2004 | Manasas et al. | |
| 6,960,232 B2 | 11/2005 | Lyons et al. | |
| 6,966,929 B2 | 11/2005 | Mitchell | |
| 7,361,192 B2 | 4/2008 | Doty | |
| 2003/0235525 A1* | 12/2003 | Honjo et al. | 423/210 |
| 2006/0136063 A1* | 6/2006 | Zeegers | 623/17.14 |
| 2006/0178744 A1* | 8/2006 | de Villiers et al. | 623/17.13 |
| 2006/0235525 A1* | 10/2006 | Gil et al. | 623/17.13 |
| 2006/0235527 A1 | 10/2006 | Buettner-Janz et al. | |
| 2007/0067038 A1 | 3/2007 | Studer et al. | |

FOREIGN PATENT DOCUMENTS

| | | |
|---|---|---|
| DE | 3023353 | 4/1981 |
| EP | 0042271 | 12/1981 |
| EP | 0176728 | 4/1986 |
| EP | 2718635 | 10/1995 |
| EP | 0699426 | 3/1996 |
| SU | 1225561 | 4/1986 |
| WO | WO 91/13598 | 9/1991 |
| WO | WO 92/14423 | 9/1992 |
| WO | WO 93/10725 | 6/1993 |
| WO | WO 94/04100 | 3/1994 |
| WO | WO 98/14142 | 4/1998 |

OTHER PUBLICATIONS

Bao, Q.-B. et al. "The Artificial Disc: Theory, Design and Materials" *Biomaterials*, 1996, pp. 1157-1167, vol. 17, No. 12.

Bogduk, N. et al. "A Biological Basis for Instataneous Centres of Rotation of the Vertebral Column" *Proc. Instn. Mech. Engrs.*, 1995, pp. 177-183, vol. 209.

Bogduk, N. et al. "Biomechanics of the Cervical Spine. I: Normal Kinematics" *Clinical Biomechanics*, 2000, pp. 633-648, vol. 15.

Bogduk, N, et al. "Clinical Anatomy of the Lumbar Spine,"ISBN 0-443-03505-9, Churchill-Livingstone Melbourne Edinburgh London New York, 1987.

Buttner-Jantz K., et al. "The Artificial Disc", ISBN 3-540-41779-6, Springer-Verlag, Berlin Heidelberg New York, 2003.

Herman, A.M. et al. "A new Computer-Aided Technique for Analysis of Lateral Cervical Radiographs in Post-Operative Patients with Degenerative Disease" Cervical Spine Research Society, 13th Annual Meeting, Dec. 5-7, 2002, Miami Beach, FL.

Mameren, H. van et al. "Cervical Spine Motion in the Sagittal Plane II: Position of Segmental Averaged Instantaneous Centers of Rotation—A Cineradiographic Study" *Spine*, 1992, pp. 467-474, vol. 17, No. 5.

Margulies, J.Y. and Adler, R.L., "Geometry of Scoliotic Space Curves" Biotechnologies for Spinal Surgery Meeting, Apr. 11-13, 2002, Halle, Germany (Abstract).

Mow, V.C. and Hayes, W.C. "Basic Orthopaedic Biomechanics", 2nd Edition, Lippincott-Raven Publ., NY, 1997.

Panjabi, M. M. et al. "Articular Facets of the Human Spine: Quantitative Three-Dimensional Anatomy" *Spine*, 1993, pp. 1298-1310, vol. 18, No. 10.

Panjabi, M. M. "Point of View: Instantaneous Center of Rotation and Instability of the Cervical Spine" *Spine*, 1997, pp. 647-648, vol. 22.

Yoganandan, N, Maiman DJ, Pintar FA: Biomechanics of the cervical spine. In Principles of Spinal Surgery, Menezes AH, Sonntag VKH (ed), McGraw-Hill, 1996. Chapter 5, pp. 69-83.

Zigler, Jack, "Lumbar Artificial Disc Surgery for Chronic Back Pain", 2004, pp. 1-24 found at www.spine-health.com/research/discupdate/artificial/artificial01.html.

* cited by examiner

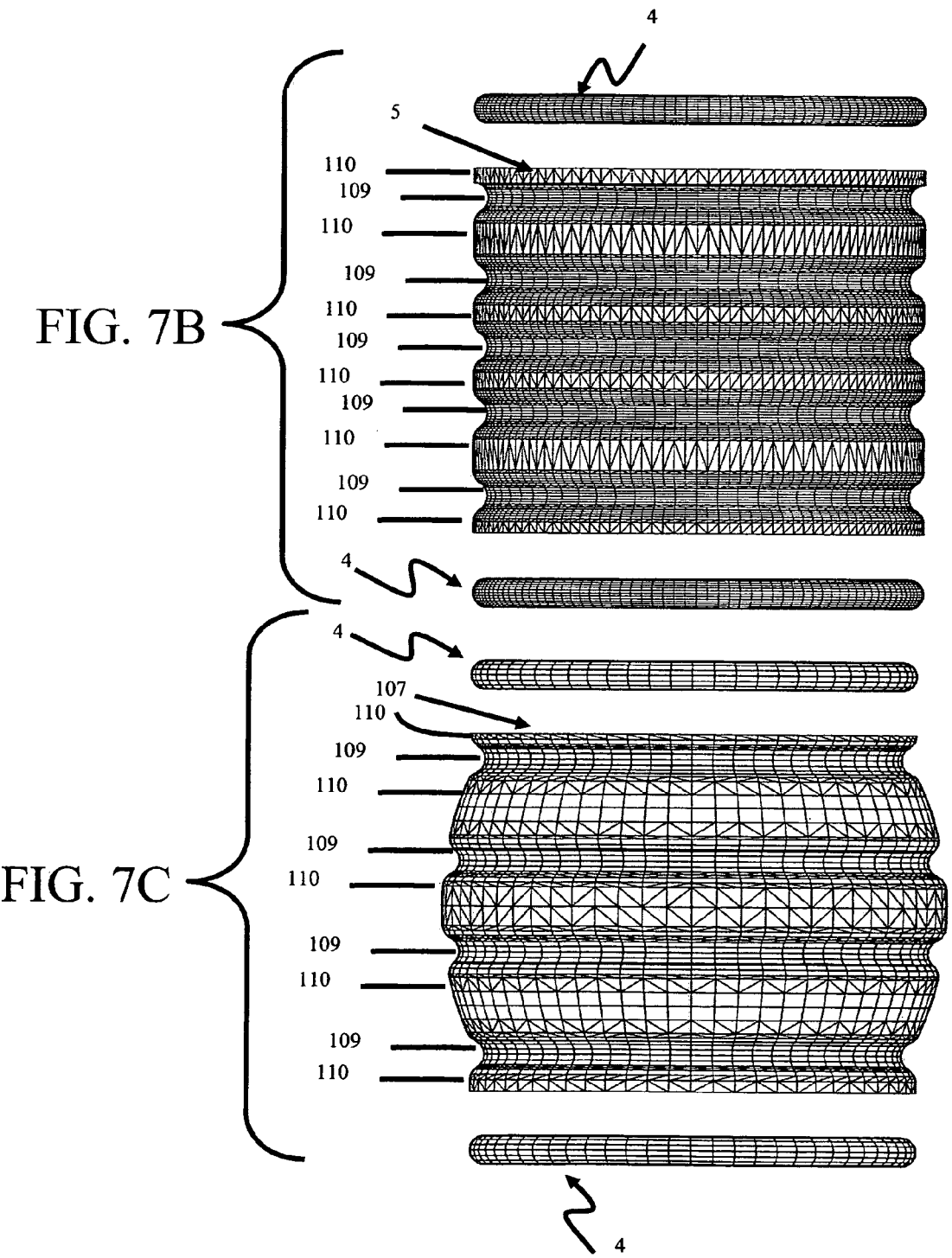

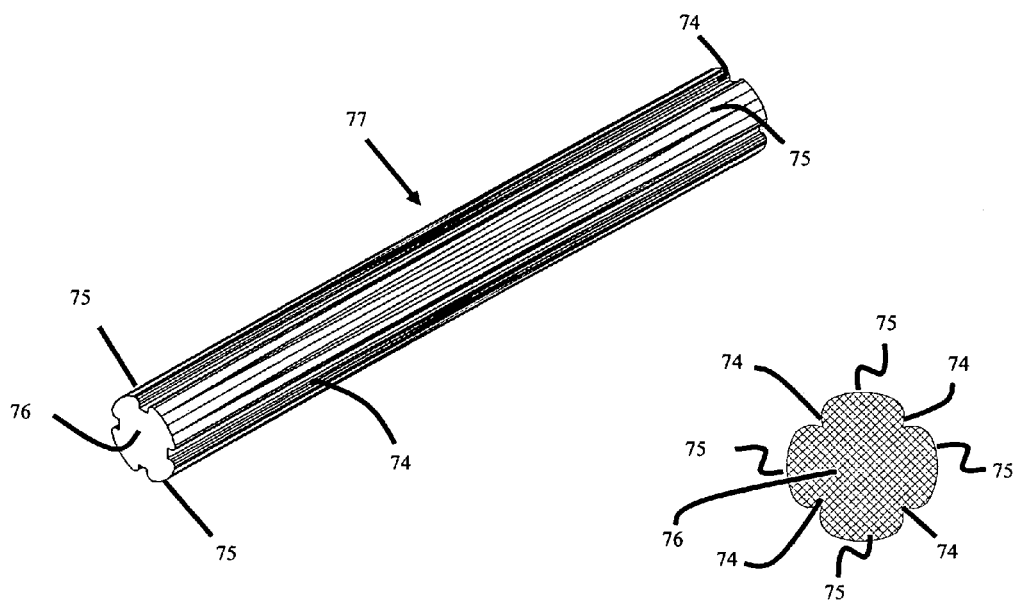
FIG. 23A
FIG. 23B
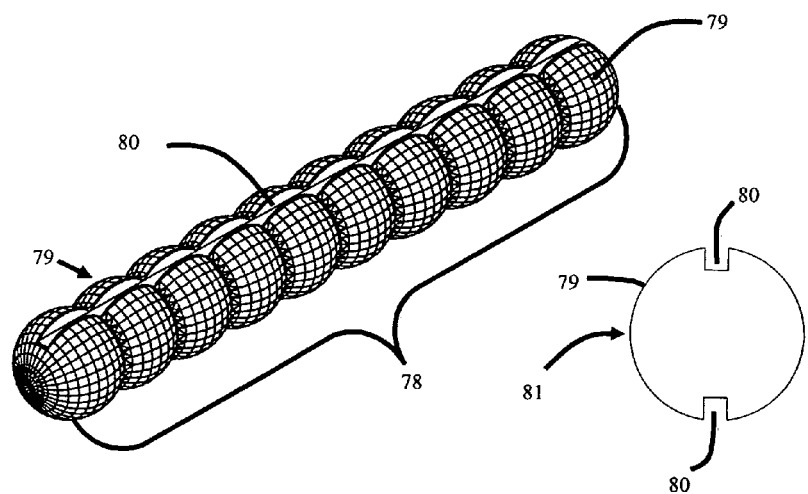
FIG. 24A
FIG. 24B

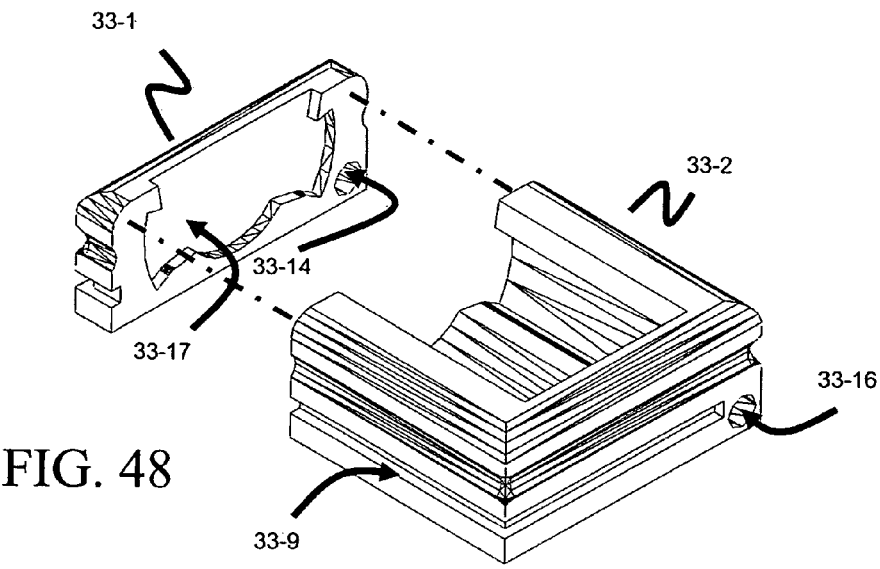
FIG. 48
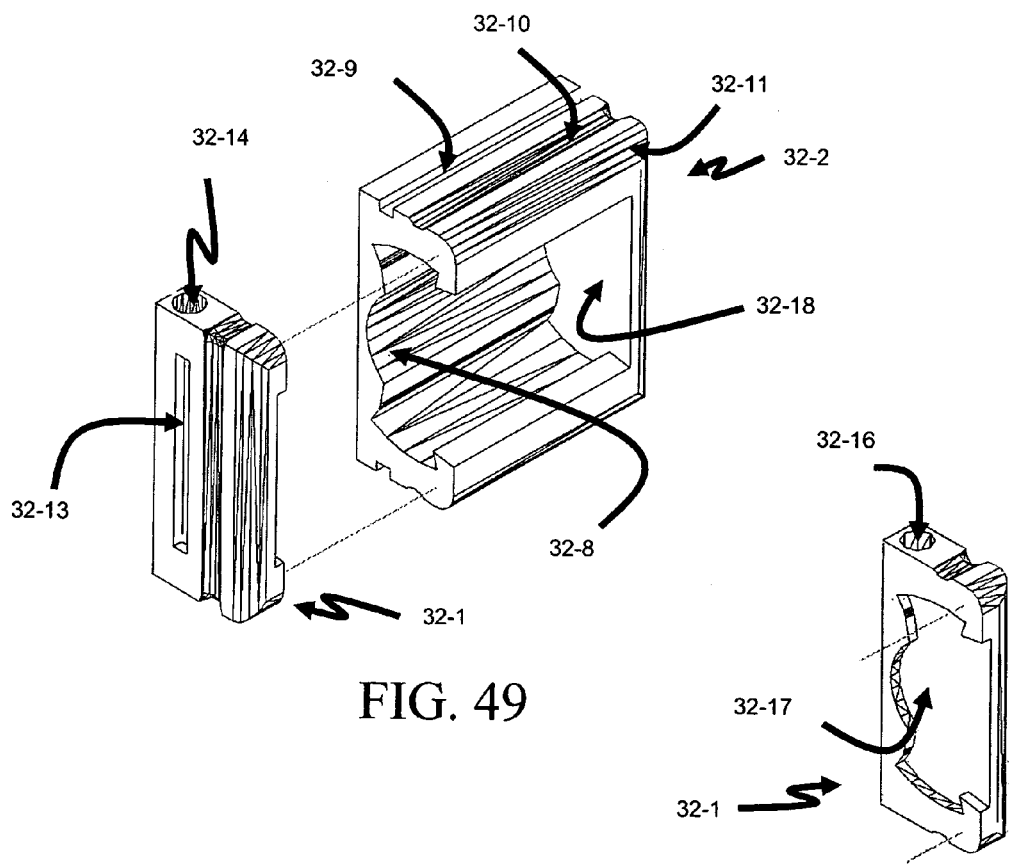
FIG. 49
FIG. 50

SPINAL DISC PROSTHESIS AND METHODS OF USE

CROSS-REFERENCE TO RELATED APPLICATION(S)

The present application is a continuation-in-part of U.S. application Ser. No. 11/112,832, filed Apr. 22, 2005 now U.S. Pat. No. 7,361,192, which is hereby incorporated by reference herein in its entirety, including any figures, tables, or drawings.

BACKGROUND OF INVENTION

Spinal disc herniation, a common ailment, often induces pain, as well as neurologically and physiologically debilitating processes for which relief becomes paramount. If conservative treatments fail, the more drastic measures of discectomies and spinal fusion may be indicated. The later treatment, while providing short term relief, often leads to excessive forces on facet joints adjacent to the fusion and creates further problems over time. Drastic treatments are usually unable to restore normal disc function. The loss of disc function has led to a number of disc prosthesis that attempt to provide natural motion.

The literature documents that the instantaneous axis of rotation (IAR) during sagittal rotation of the superior vertebra with respect to the inferior vertebra of a Functional Spinal Unit (FSU) in the cervical spine moves significant distances during flexion and extension of the spine (Mameren H. van, Sanches H., Beursgens J., Drukker, J., "Cervical Spine Motion in the Sagittal Plane II: Position of Segmental Averaged Instantaneous Centers of Rotation-A Cineradiographic Study", *Spine* 1992, Vol. 17, No. 5, pp. 467-474). This motion varies widely between functional spinal units on an individual spine and between individuals and depends on age, time-of-day, and the general health and condition of the intervertebral discs, facet joints and other components of the FSU and spine. A moving IAR means that the superior vertebra both rotates and translates while moving with respect to the inferior vertebra of an FSU. Natural spinal motions place severe requirements on the design of a prosthetic disc; simple rotational joints are not able to meet those requirements.

In addition, motion coupling between axial and lateral bending and other functional spinal units involved in the overall spinal motion increases the complexity and difficulty in developing a prosthetic disc replacement that realizes natural spinal motion. The complex facet surfaces in an FSU significantly influence and constrain sagittal, lateral and axial motions. The orientation of these facet surfaces vary with FSU location in the spine and induce wide variations in motion parameters and constraints. The complex motion of a superior vertebra with respect to the associated inferior vertebra of an FSU, certainly in the cervical spine, cannot be realized by a simple rotation or simple translation, or even a combination of rotation and translation along a fixed axis, and still maintain the integrity and stability of the FSU and facet joints.

One advantage of a general motion spatial mechanism as a disc prosthesis, as described in this application, is that it solves the complex, challenging motion problem posed by nature for disc prosthesis and offers a scalable mechanism for disc replacement without loss of general motion capabilities in the FSU.

Researchers have engineered various spinal disc prosthetic devices that attempt to mimic the natural FSU motions. For example, U.S. Pat. No. 6,733,532, utilizes a cylindrical arrangement of leaf springs (bellows) with a central cushion that provides a non-linear compression response similar to a natural FSU. However, such a design can be limited to the lumbar region of the spine and may not be stable under lateral spinal forces. Another example is U.S. Pat. No. 6,579,321 which utilizes a helical spring with central cushions seated on support balls. This device appears unable to provide lateral or sagittal linear displacements, which can limit motion when implanted in a natural FSU. A further example is U.S. Pat. No. 5,827,328, which provides a spinal disc prosthesis having multiple springs with adjustable platforms that fit within the vertebrae of a natural FSU. However, the size constraints of the device can limit implantation to the lumbar FSU region, and may still require excessive vertebral bone loss to facilitate implantation, even in the lumbar region of a spine.

Other researchers have also attempted to design a successful intervertebral disc for years. Salib et al., U.S. Pat. No. 5,258,031; Marnay, U.S. Pat. No. 5,314,477; Boyd et al., U.S. Pat. No. 5,425,773; Yuan et al., U.S. Pat. No. 5,676,701; and Larsen et al., U.S. Pat. No. 5,782,832 all use ball-and-socket arrangements fixed to the superior and inferior plates rigidly attached to the vertebrae of an FSU. However, these designs limit motion to rotation only about the socket when the two plates are in contact. As the literature points out (Bogduk N. and Mercer S., "Biomechanics of the cervical spine. I: Normal kinematics", *Clinical Biomechanics, Elsevier,* 15(2000) 633-648; and Mameren H. van, Sanches H., Beursgens J., Drukker, J., "Cervical Spine Motion in the Sagittal Plane II: Position of Segmental Averaged Instantaneous Centers of Rotation-A Cineradiographic Study", Spine 1992, Vol. 17, No. 5, pp. 467-474), this restricted motion does not correspond to the natural motion of the vertebrae, even for sagittal plane motion, much less for combined sagittal, lateral and axial motion. Further, when the two plates, as described in the cited patents, are not in contact, the devices are unable to provide stability to the intervertebral interface, which can allow free motion and lead to disc related spondylolisthesis, FSU instability and excessive facet loading.

As a further elaboration on the many ball-and-socket configurations, consider Salib et. al. (U.S. Pat. No. 5,258,031) as an example of previous efforts to address this problem. The Salib ball-and-socket arrangement only provides 3 independent axes of rotation and no translation when engaged.

During complex motions of an FSU, the superior vertebra, in general, requires translation along three independent directions. A sliding ovate structure in an oversized socket cannot perform such general translation motions, either, as it must engage in a trajectory dictated by its socket's geometrical surface and does not change the deleterious effects that may occur on the facet joints of the unit. The current invention overcomes these deficiencies of prior art devices by providing a full 6 degrees-of-freedom throughout the motion space of the FSU. In a preferred embodiment, the subject invention is also able to provide shock absorption, static compression and extension load bearing, as well as some torsion load bearing from a strong, flexible, corrugated boot covering.

The Cauthen rocker arm device (U.S. Pat. Nos. 6,019,792 and 6,179,874) appears to have similar motion and instability limitations as do the freely moving sliding disc cores found in the Bryan et al. patents (U.S. Pat. Nos. 5,674,296; 5,865,846; 6,001,130; and 6,156,067) and the SB Charité™ prosthesis, as described by Büttner-Jantz K., Hochschuler S. H., McAfee P. C. (Eds), *The Artificial Disc,* ISBN 3-540-41779-6 Springer-Verlag, Berlin Heidelberg New York, 2003; and U.S. Pat. No. 5,401,269; and Buettner-Jantz et al. U.S. Pat. No. 4,759,766) devices. In addition, the sliding disc core devices of the Bryan et al. and SB Charité™ devices do not permit natural motion of the joint for any fixed shape of the core.

When the FSU extends, the prosthesis's sliding core, in some cases, generates unnatural constraining forces on the FSU by restricting closure of the posterior intervertebral gap in the FSU. In any case, the core does not mechanically link the upper and lower plates of the prosthesis and has no means of maintaining the intervertebral gap throughout the range of motion. Such conditions inevitably contribute to prosthetic disc spondylolisthesis. In general, unconstrained or over-constrained relative motion between the two vertebral plates in a prosthetic disc contributes to FSU instability over time.

Further, current prosthetic disc technology is able only to minimally and rigidly support static loading. For example, load bearing and shock absorption in the SB Charité™ design and others (e.g. Bryan et al., U.S. Pat. No. 5,865,846) rely on the mechanical properties of the resilient, ultra-high-molecular-weight polyethylene core to provide both strength and static and dynamic loading. The rigidity of the sliding core appears to offer little energy absorption and flexibility to meet the intervertebral gap requirements during motion, and most likely generates excessive reaction forces on the spine during flexion, forces that potentially produce extra stress on facet joints and effect mobility.

With respect to the lower vertebra in an FSU, all possible, natural loci of motion of any four non-planar, non-collinear points located in the superior vertebra define the natural workspace of the FSU. This workspace varies from FSU to FSU on the spine, creating considerable spinal disc prosthesis design problems.

The FSU workspace boundary is dictated by the sagittal, lateral and axial angle limits reported in the literature (Mow V. C. and Hayes W. C., *Basic Orthopaedic Biomechanics*, Lippincott-Raven Pub., N.Y., $2^{nd}$ Addition, 1997). However, these angle limits do not reveal the underlying complex motion between two vertebrae in an FSU. The study by Mameren H. van, Sanches H., Beursgens J., Drukker, J., "Cervical Spine Motion in the Sagittal Plane II: Position of Segmental Averaged Instantaneous Centers of Rotation-A Cineradiographic Study", Spine 1992, Vol. 17, No. 5, pp. 467-474 demonstrates this complexity in the cervical spine, even when the motion is restricted to flexion and extension. The subject invention is able to accommodate a broader range of motions, since it moves freely with 6-degrees-of-freedom (DOF) within the angle limits reported for all axes.

BRIEF SUMMARY

The subject invention provides spinal disc prostheses capable of up to 6 independent degrees of freedom that further allow the engineering of spring parameters to realize a dynamical response for each of those degrees of freedom that approximates the mechanical response of a human spinal disc undergoing motion. The modular prosthetic discs of the subject invention contain the mechanisms responsible for their general motion and dynamical response capabilities. In certain embodiments, the devices of the subject invention facilitate sagittal, lateral, and polar, or axial, vertebral movement when utilized in the spine of an animal, particularly a human.

Certain embodiments of the subject invention also provide modular spinal disc prostheses comprising superior and inferior vertebral plates, as well as a flexible, boot-protected replaceable 6-degrees-of-freedom (DOF) modular prosthetic disc mechanism (linkage). The up to 6-DOF achieved by the subject invention are provided by means of up to 3 independent rotational degrees of freedom and by means of up to 3 independent linear degrees of freedom (DOF), the most general motion possible in 3 dimensional space.

For example, in one embodiment, the rotational degrees of freedom can be provided by means of a ball and socket joint, a cylinder and socket joint, a piston and socket joint, a universal (or Hooke) joint, or variations thereof. In this embodiment, the modular prosthetic disc mechanism of the subject invention can comprise three orthogonal prismatic joints for general positioning in three-dimensional space and a spherical joint for three-dimensional orienting.

Preferably, this embodiment of the subject invention comprises a socket-base for containing a chambered-ball such that the chambered-ball is capable of rotating within the socket-base, providing 3-DOF for orienting the superior vertebral plate with the inferior vertebral plate. The chambered-ball itself possesses a cavity for containing a piston. The piston is slidably fixed within the cavity of the chambered-ball such that the piston is capable of sliding to and fro in the chambered-ball cavity.

The piston possesses a cavity for containing a spring or similar device or material to absorb shocks and excessive loads on the disc prosthesis. The spring is fixedly attached at one end at or near the floor of the chambered-ball and extends within the cavity of the chambered-ball such that the piston, inserted into the cavity of the chambered-ball, is able to rest on top of the opposite end of the spring or similar device. The combined piston and chambered-ball joint constitutes a polar-axis prismatic joint. The piston slides in and out of the chambered-ball cavity along the piston centerline, which also coincides with the polar-axis of the chambered-ball. The piston and chambered-ball unit thereby function as a rotating telescoping joint. Loads placed on the top piston are absorbed by the spring or similar device as the piston is recessed into the chambered-ball cavity.

In yet a further embodiment, a dual-track, orthogonal linear bearing is fixedly attached to the distal end of the piston. This linear bearing is slidably attached to a further element of the device referred to as a plane-bearing guide to create yet a further kinematically connected element of the device of the subject invention. The plane-bearing guide has two linear raceways, sagittal-oriented and lateral-oriented, on opposite sides, which are perpendicular to each other. The linear bearing on the piston is slidably affixed within the sagittal-oriented raceway. When positioned within a spine, the combined piston and plane-bearing guide allows movement of the functional spinal unit (FSU) along the raceway within the plane described by the polar axis and the line of action of this joint. This joint is called the sagittal prismatic joint since the aforementioned plane which moves about in space, is the sagittal plane for pure flexion of the spine.

The arrangement of sliding pathways and sliding guide differs from Khandkar et al (U.S. Pat. No. 6,994,727 B2 Feb. 7, 2006 FIG. 1) in that the bearing guide in this particular embodiment is planar and not arcate for the two orthogonal directions, so that the plane-bearing guide can be slidably fixed to the upper and lower sliding bearing surfaces, preventing the plane-bearing guide from being ejected out of the device and, simultaneously, leaving unbroken the kinematic chain that maintains the connectedness of all the elements of the prosthetic device with the inferior and superior vertebrae to which the prosthetic device attaches. Further, the lower planar bearing surface has 3-degrees-of rotation freedom via the ball-and-socket joint, thus, allowing the plane of the two sliding bearings to be at any orientation with respect to the ball joint. The Khandkar et al. device permits only 2-degrees of rotation freedom and 2-degrees of sliding motion, one for each bearing surface, that are not kinematically chained.

In still a further embodiment, additional dual-track, orthogonal linear bearings, located on a part of the device referred to as a cap-plate, are slidably affixed within the lateral-raceways on the plane-bearing guide. When positioned within a spine, the combined cap-plate and plane-bearing guide allows movement of the FSU along the raceway within the plane described by the polar axis and the line of action of this joint. This joint is called the lateral prismatic joint. The aforementioned plane moves about in space, but is the frontal plane for pure lateral bending.

Thus, the plane-bearing guide element provides two prismatic joints: the cap-plate and the plane-bearing guide for the lateral prismatic joint, and the plane-bearing guide and the piston for the sagittal prismatic joint. Together, the prismatic joints provide two orthogonal degrees-of-freedom.

In a preferred embodiment, ball-bearings are utilized in combination with the sagittal and lateral prismatic joint raceways. Ball-bearings are able to provide smooth movement and reduced friction between the elements of the prismatic joints. Alternative embodiments utilize bearing stops to limit movement within one or more of the prismatic joints. In another embodiment, the sagittal and lateral prismatic joints use surface bearings dictated by the geometry of the lower pair forming the joint.

An alternative embodiment provides a disc prosthesis utilizing three mutually orthogonal cylindrical joint mechanisms that provide six-degrees-of-freedom over the allowed motions (workspace) of the spinal disc. Each cylindrical joint allows translation and rotation along its axis. One cylinder provides for sagittal rotation and lateral translation, another lateral rotation and sagittal translation, and the third for axial compression, extension and rotation. In a preferred embodiment, each cylinder consists of a spring device that allows compression/extension and torsion, but remains relatively stiff to lateral bending. This design provides a dynamical response to forces along, and moments-of-force about, each cylindrical axis, thus encompassing a complete dynamical response to nominal loads on the prosthesis. In a further preferred embodiment, each cylinder is a machined helical spring comprising, for example, titanium steel or any of a variety of bio-inert materials, designed to provide the dynamic response required by the spinal disc. Scaling, conjoined with motion limit stops, allows the device to realize any nominal spinal articulation, from the cervical to lumbar regions. A further alternative of this embodiment employs surface contact bearings (lower kinematic pairs) between the sagittal and lateral cylinders and the substrate in which the cylinders locate. In this embodiment, the central axis cylinder does not form a joint with any surface, but fixedly connects the sagittal and lateral cylindrical joints. In a further preferred embodiment, one or more mechanical hard joint-limit stops are employed on one or more joints. In addition to human spinal disc prosthesis application from vertebrae C2-C3 to L5-S1, the device is also suitable for veterinary or even mechanical applications, large or small, where the device constrains the relative position and orientation between two objects to a specific workspace without hindrance in that workspace and bears compression, extension, and torsion loads with passive mechanical components.

In preferred embodiments, a flexible boot surrounds the functional elements of the prosthetic devices. In a further preferred embodiment, the boot is wrapped around the prosthetic devices and clamped, or otherwise connected, to the superior and inferior ends of the devices. In yet a further preferred embodiment, the boot is sealed such that surrounding bodily fluids or other bio-environmental materials cannot contact the functional elements of the prosthetic devices. In a still further preferred embodiment, the sealed boot can contain fluids (liquids and/or gases), viscous fluids, and/or colloidal suspensions of elastomer materials in a viscous fluid to lubricate the functional elements of the prosthetic devices and/or provide compressive resistance and motion dampening to the moving elements within the device.

However, in certain applications of the subject device, the boot and/or lubricating and/or colloidal suspension properties may not be required and are not necessary to the functionality of the prosthetic devices.

In further embodiments, one or more vertebral plates are utilized to connect the prosthetic devices between two vertebrae. Specifically, superior and inferior vertebral plates can be attached to the respective vertebrae within a spine. The prosthetic device of the subject invention can thus be positioned between, and connected to, the vertebral plates.

In even further embodiments, the one or more vertebral plates are threaded in opposite directions. This allows certain prosthetic device embodiments to be positioned between the vertebral plates and turned in one direction to screw the prosthetic device to both vertebral plates at the same time. It can also be preferable to utilize screws to secure the prosthetic device in place after it has been screwed to the vertebral plates.

In alternative embodiments, the prostheses can be affixed to the vertebrae without the use of vertebral plates. In these embodiments, the prosthetic devices are less modular and more permanently affixed to the vertebrae. In preferred embodiments, the devices comprise superior and inferior plates having grooves, holes or other means by which vertebral bone can incorporate into and around the plates. In addition, one or more screws, pins, or similar means can be utilized to secure the devices initially and until the natural vertebral bone incorporates sufficiently to secure the devices in the spine.

Thus, in a preferred embodiment, the present invention provides articulated, modular 6-Degrees-of-Freedom (6-DOF) spatial mechanisms for intervertebral spinal disc prostheses that provide highly advantageous spatial motion between upper and lower vertebrae of an FSU.

The prostheses can be used to assist in maintaining natural spinal flexibility and motion during simultaneous, dynamically changing, curvilinear axial, lateral and sagittal rotations and translations, regardless of the details and wide variations of that motion in humans.

The prostheses can also be used to assist in maintaining proper disc spacing, absorbing compression shocks, sustaining static loads, helping to eliminate spinal cord and nerve root compression, resisting torsion and extension forces and reducing excessive facet joint stress and wear.

The components of the mechanisms, when coupled together, form devices that preserve their mechanical integrity, connectedness (kinematic chain), and motion properties throughout the biologically constrained motion space (workspace) of the FSU. The complete generality of the devices allow for modifying the range of motion parameters and workspace, physical size, material composition, and mechanical strength of the mechanisms to suit ordinary mechanical applications, as well as spinal disc prosthetics.

The complete 6-DOF motion capability of the prosthetic disc linkage mechanisms, are able to allow natural motions dictated by the muscles and ligaments of the spine. For example, in one embodiment, a central compression-extension, machined helical spring with an optional elastomeric or hydrophilic gel partially filling the spring core, automatically rotates to align itself with a normal component of applied force and absorbs and transmits spinal shocks while helping to maintain normal intervertebral spacing. The mechanism can support further shock absorption and automatic bearing lubrication by means of a self-contained internal hydraulic pumping and damping system using a biocompatible, for example, but not limited to, a silicone fluid, or, for thermoplastic bearings and mechanism parts, for example, but not limited to, a biocompatible saline solution. In addition, as mentioned above, certain embodiments provide modular capabilities allowing the device to realize a replaceable independent unit.

Throughout normal motion, the systems of the subject invention stabilize the FSU because of their ability to maintain continuity of mechanical connection between the superior and inferior vertebrae while at the same time providing load bearing and permitting motion only within the nominal disc operating range or workspace. The mechanical continuity is realized by a kinematic chain of jointed elements. In order to stabilize the FSU, embodiments of the subject invention generate nominal forces opposing vertebral motions by means of central, rotating, machined helical springs with an optional elastomer or hydrophilic gel core and by means of the device structure itself. The mechanisms also include hydraulic-damping to absorb and even out energy shocks.

BRIEF DESCRIPTION OF DRAWINGS

The file of this patent contains at least one drawing executed in color. Copies of this patent with color drawings(s) will be provided by the Patent and Trademark Office upon request and payment of the necessary fee.

FIG. 2A illustrates the embodiment with a right-circular cylinder boot and FIG. 2B illustrates the embodiment with a spherical boot.

FIGS. 7A, 7B and 7C illustrate exploded views of the chambered-ball embodiment prosthesis of the subject invention. FIG. 7A illustrates interior elements of this embodiment.

FIG. 7B illustrates a right-circular cylinder boot utilized with clamping rings and FIG. 7C illustrates the embodiment with a spherical boot utilized with clamping rings.

FIGS. 23A and 23B and FIGS. 24A and 24B represent alternative rod-bearings that can be used in the embodiments to replace ball-bearings in the prismatic joints or other interfacing surfaces. In circular form, they can also replace ring bearings. The bearings do not roll but have different contact surfaces, resulting from different choices of cross-sections and lateral surface shapes, and grooves for lubrication flow.

FIG. 25B portrays the sagittal plane projection of the device elements through the polar-axis of the ball. The projection indicates that the plane-bearing guide, cap plate, and superior vertebral plate of this embodiment slide from anterior to posterior positions along the sagittal prismatic joint.

FIG. 26B portrays the sagittal plane projection of the device elements, through the polar-axis of the ball. The projection indicates that the plane-bearing guide, cap-plate and superior vertebral plate of this embodiment slide from posterior to anterior positions along the sagittal prismatic joint.

FIG. 27B is a cross-sectional view of the frontal plane projection through the polar-axis of the ball which indicates that in pure right-lateral bending, the cap-plate and superior vertebral plate slide from left-to-right along the lateral prismatic joint.

FIG. 48 illustrates a cutaway view of the sagittal cylindrical-joint platform.

FIG. 49 illustrates the lateral cylindrical-joint platform structure for this modular embodiment that slides into bone-fixed vertebral plates. The platform consists of a main body and an endplate. The endplate bonds to the main body, after the central mechanism has been inserted. Interlocking surface elements between the two parts (not shown) and other assembly techniques can be employed to strengthen this join. The grooved sides provide a tongue-and-groove insertion into of the upper vertebral cap. The clamping bar has a tongue that meshes with the front groove of the platform.

FIG. 50 shows the various surfaces that mesh with the rocker-slider. The sides also have an indent for securing a boot with a clamping ring. The various interface surfaces between the platform and the rocker-slider are the same as those of the sagittal cylindrical platform.

DETAILED DISCLOSURE

Figure 1A:
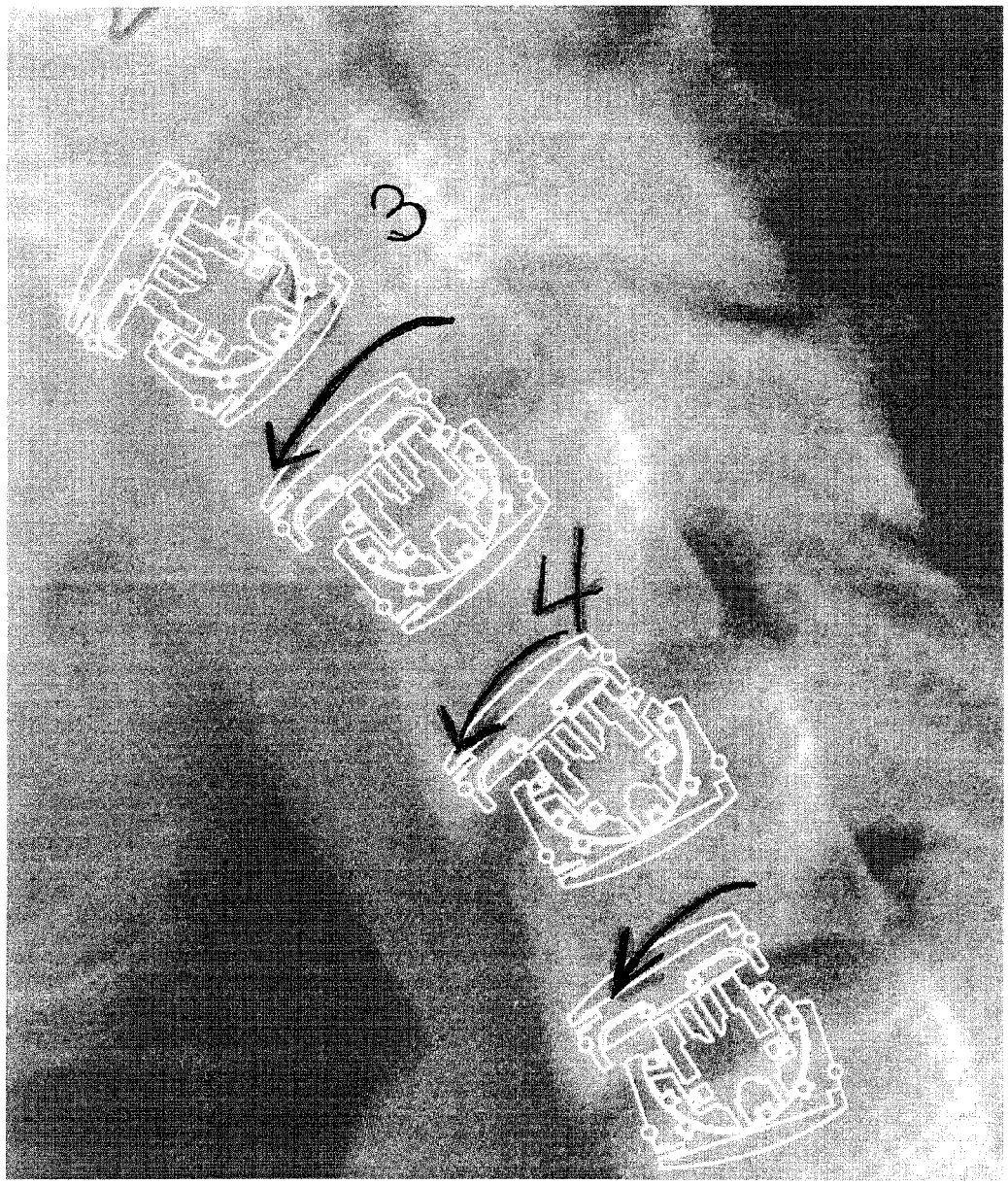
FIGS. 1A-1C (photographs) are photographs of superimposed sagittal plane projections, through the central axis of the chambered-ball spinal disc prosthesis embodiment of the subject invention, onto sagittal view radiograms of the cervical spine, from left to right, in flexion, neutral, and extension. The modular 6-degrees-of-freedom (DOF) spatial mechanism is shown as prostheses for C2-C3, C3-C4, C4-C5, and C5-C6 since the workspace of the embodiments of the invention are able to correspond to the workspace of each of these functional spinal units.

With reference to the attached figures, which show certain embodiments of the subject invention, it can be seen that the subject invention pertains to spinal disc prostheses that are capable of up to 6 independent degrees of freedom. Certain embodiments of these prostheses permit the engineering of spring parameters to enable a dynamical response for each of those degrees of freedom to approximate the mechanical response of a human spinal disc undergoing motion. The modular prosthetic discs of the subject invention contain the mechanisms responsible for their general motion and dynamical response capability. The embodiments of the subject invention differ from existing designs by providing up to six-degrees-of-freedom throughout the functional spinal unit (FSU) workspace while bearing loads and maintaining the integrity of intervertebral spacing.

The embodiments of the spatial mechanisms for human spinal disc prosthesis described here overcome problems inherent in prior devices and can offer a number of other novel features, for example, modularity, scalability, static and dynamic loading, shock absorption, lubrication pumping, hydraulic damping, and wide applicability throughout the spinal column.

I. Chambered-Ball Spinal Disc Prosthesis:

This embodiment of the subject invention provides a spinal disc prosthesis that enables spatial movement with up to 6 independent degrees of freedom. In this embodiment, the mechanisms comprise orthogonal prismatic joints for general positioning in three-dimensional space and, in one embodiment, a spherical joint for three-dimensional orienting.

A preferred chambered-ball embodiment possesses at least three orthogonal linear (prismatic) joints and a three-independent rotational degrees-of-freedom orienting ball-and-socket joint that, when assembled for insertion into a spine, form a kinematic chain. When appropriately scaled, the device can track arbitrary three-dimensional translational and three-dimensional rotational motions of the superior vertebra with respect to the inferior vertebra of an FSU from C2-C3 down to L5-S1.

The embodiments of the spinal disc prosthesis of the subject invention are operated by the muscles and ligaments of the spine. These muscles and ligaments work against the various joints and spring-damping systems of the prostheses and dictate the motion of the FSU vertebra rigidly attached to the prostheses.

The 3-DOF spherical joint provided by the ball-and-socket elements, of the chambered-ball embodiment, tracks the spatial orientation of the superior vertebral plane fixed in the superior vertebral plate which, in turn, is fixed in the superior vertebra of the FSU. The instantaneous axis of rotation changes during the motion of the superior vertebra of the FSU and, therefore, in general, differs from the fixed rotation center of the ball-and socket joint. Ball-and-socket action alone, therefore, does not produce all the required translations of the superior vertebra, but does produce the correct and final orientation. It requires the polar-axis (piston-and-ball) prismatic joint, along with the lateral and sagittal prismatic joints to fix the three coordinate position of a point in the superior vertebral plane. Together the ball-and-socket and the three prismatic joints form the kinematic chain that determines the location and orientation of the vertebral plane, completely fixing it in space. In this manner the prosthetic spinal disc tracks and constrains the motion of the superior vertebra to its natural locus of motion. Advantageously, the chambered-ball embodiment can provide 1) effective static load bearing through the axial spring, 2) hydraulic damping and shock absorption by means of hydraulic pumping action conjoined with spring and, optionally, elastomer (or hydrophilic gel) reaction in the spring core, 3) automatic hydraulic lubrication of all joints, 4) intervertebral stability, 5) 6-DOF motion tracking throughout the prosthesis workspace, 6) and a mechanically programmable prosthesis workspace.

The motion elements of the prosthetic device of the subject invention can be fabricated of, for example, titanium steel, titanium-carbide-coated stainless steel, polyurethane, polyurethane thermoplastic, cobalt-chromium-molybdenum alloy, plastic, or other materials or combinations thereof. In a preferred embodiment, the motion elements of the prosthetic devices of the subject invention are fabricated from titanium and, in certain embodiments, use hardened ball-bearings on moving interfaces. In a further preferred embodiment, a mix of polyurethane thermoplastic bearings and polyurethane, titanium, cobalt-chromium-molybdenum alloy and titanium-carbide-coated hardened stainless steel components are utilized in certain embodiments of the subject invention.

In preferred embodiments, the modular spatial mechanisms for spinal disc prosthesis of the subject invention utilize one or more superior and inferior vertebral plates, as well as a flexible, boot-protected, modular and replaceable 6-DOF prosthetic disc mechanism (linkage). The vertebral plates can be formed from a biocompatible material such as, for example, titanium, cobalt-chromium-molybdenum alloy, or titanium-carbide-coated stainless steel with a bone fusion matrix on the side of the plate shaped as a spherical surface to enhance surface area contact between vertebra and the vertebral plate.

The current invention allows installation of the vertebral plates followed by the modular prosthetic disc mechanism, or an entire prosthetic device at once, depending on indicated surgical procedures and efficiencies.

Any number of existing techniques known to those with skill in the art can be used to embed the superior vertebral plate into the bone of the superior vertebra and the inferior vertebral plate into the bone of the inferior vertebra of an FSU.

In preferred embodiments, a boot surrounds the prosthetic devices of the subject invention and provides a biocompatible barrier between fluids, colloidal suspensions, etc. that can be sealed within the prosthetic devices and fluids within surrounding tissues. The boot can also help to maintain intervertebral spatial integrity and stability of the functional spinal unit (FSU) by providing mechanical resistance to torsion and extension forces, thus, reducing prosthetic disc related spondylolisthesis. The boot can comprise a sturdy, flexible or elastic material, such as, for example, corrugated materials, woven fiber materials, and elastic materials, or other non-homogeneous materials. In a further preferred embodiment, the boot comprises woven, flexible fibers embedded in a strong, flexible silicon elastomer. The embedded fiber weave, in the embodiment mentioned above, can assist in torsion loading on the prosthesis as well as loading during flexion and extension. In an additional preferred embodiment, the weave direction of the embedded fibers is diagonal relative to the central axis of a preferred, spherical or right-circular cylinder embodiment of the boot structure.

In contrast to the skirt in the Bryan et al. design (U.S. Pat. Nos. 5,674,296; 5,865,846; 6,001,130; and 6,156,067), the boot of the subject invention can serve multiple purposes, other than sealing fluids. In a preferred embodiment, the corrugated boot, consisting of a rugged fiber elastomer designed for flexibility and toughness, can assist in torsion loading and opposes extension under nominal conditions, thus, reducing nominal spinal muscle stress in the neutral position. The boot can also help maintain the integrity of the prosthesis, and can share, with the interlinking mechanisms the force loads that are placed on the subject prosthetic device. In this sense, the boot performs, for example, as a prosthetic ligament.

In a preferred embodiment, the corrugated boot has asymmetric thickness, using more reinforcing fiber in the posterior portion and less in the anterior portion, making the anterior portion more flexible and the posterior portion less flexible, but stronger and more durable. This construction allows the boot to collapse and expand with the FSU motion without kinking or warping. This can reduce interaction with the spinal column or nerve ganglia when the boot is expanding and/or contracting. As the FSU flexes, the boot contracts, primarily the highly flexible thinner sections. In a neutral position, the boot is under about 20% stretching in the anterior part and about 10% or less in the posterior. At maximum extension the boot stretches another 20% in the anterior portion and again, about 10% or less in the posterior.

In preferred embodiments, the modular prosthetic disc mechanisms of the subject invention connect with the superior and inferior vertebral plates at each end. In certain embodiments, the modular prosthetic disc mechanisms of the subject invention connect with the superior and inferior vertebral plates by twisting or screwing into the superior and inferior vertebral plates connected to the respective vertebra. Thus, in yet another preferred embodiment the superior and inferior vertebral plates possess an opposite screw sense, such that twisting or turning in a single direction connects the modular prosthetic disc mechanism to both vertebral plates simultaneously. This enables easier installation and replacement of the prosthetic device if necessary.

In a preferred embodiment, a threaded projection on the cap-plate of certain modular prosthetic disc mechanisms of the invention screw into the superior vertebral plate and a threaded projection on the socket-base screws into the inferior vertebral plate. The modular prosthetic disc mechanisms, after being firmly screwed onto the vertebral plates, lock and align to those plates by one or more anterior screws. In a further preferred embodiment, three anterior screws are utilized to secure each vertebral plate.

While the intent of the subject invention is to provide reliable spinal disc prostheses that do not fail over the patient's lifetime, special stress or operational conditions might require replacement. The modular features of certain embodiments of the subject invention provide a means for surgical removal or replacement of a prosthetic disc linkage, as long as there is minimal or no damage to the interface between the prosthetic disc linkage and the vertebrae. This modularization of certain embodiments of the prosthetic device provides aspects of performance, serviceability, safety and security heretofore unavailable in this field, and at a considerably reduced risk to the patient.

Figure 1B:
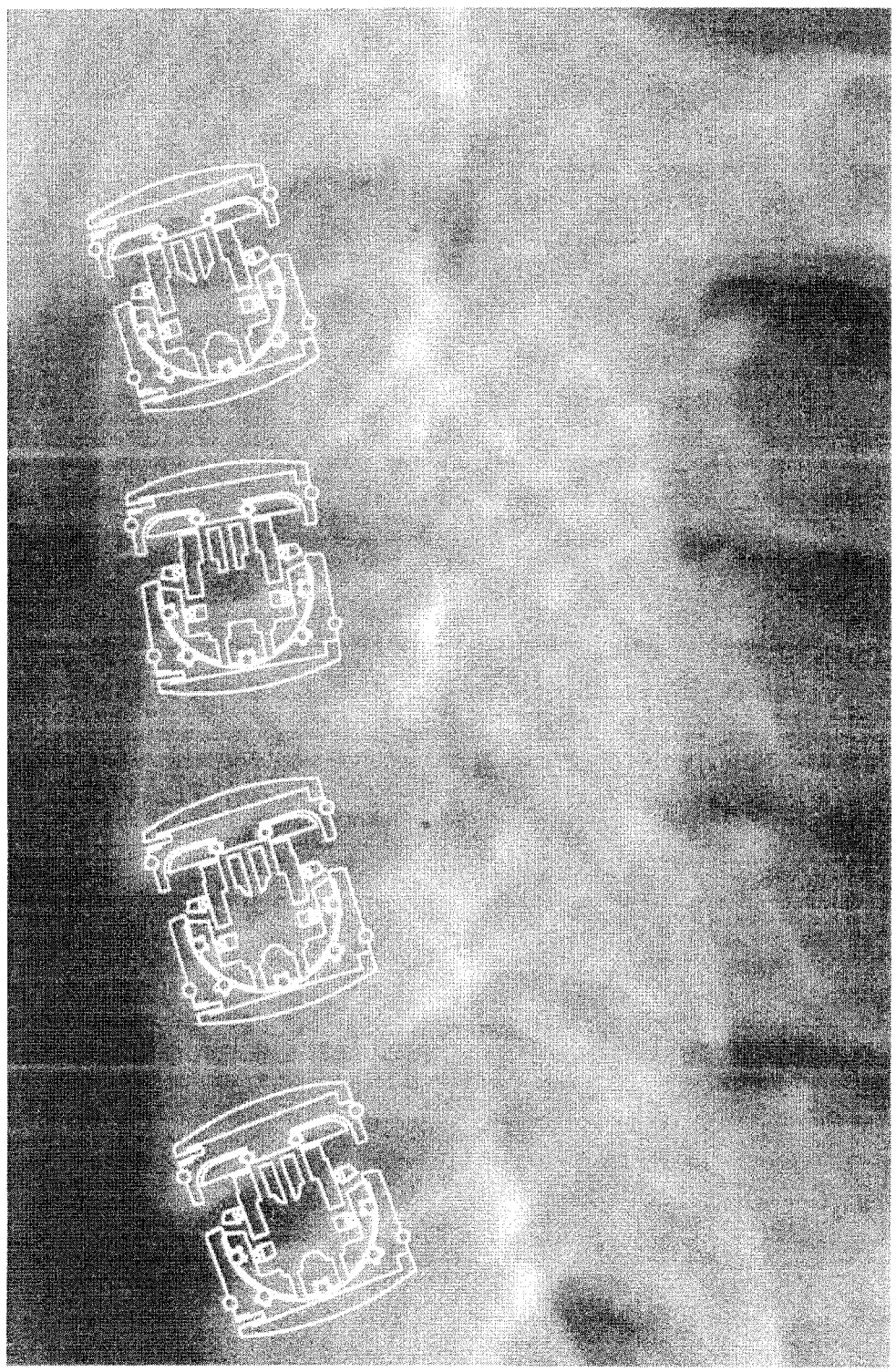
Figure 1C:
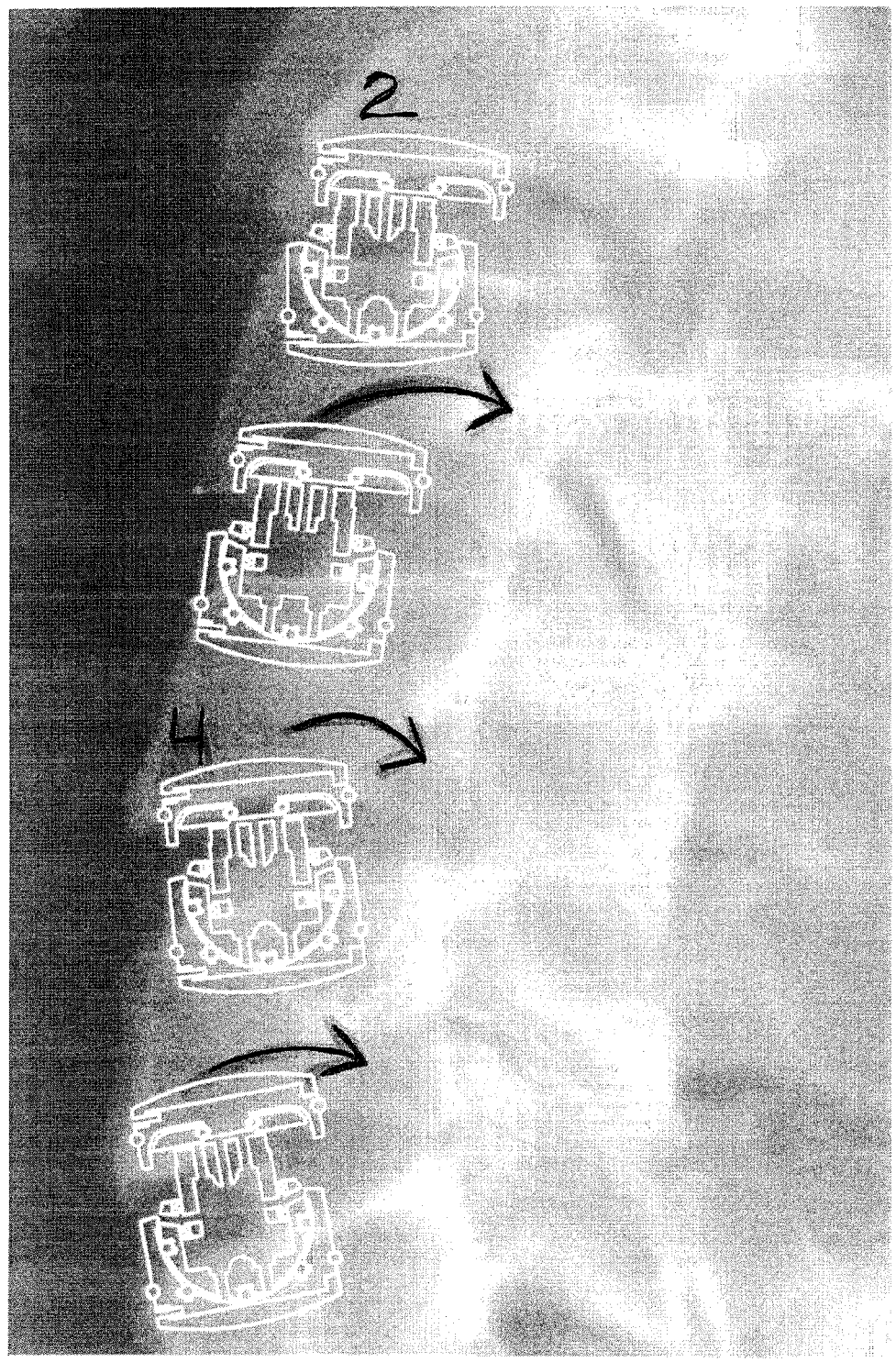

FIGS. 1A-1C illustrate possible installations of a modular embodiment of the invention into four locations (FSUs) in the cervical spine: C2-C3, C3-C4, C4-C5, C5-C6. The dimensional freedom of the device tolerates some misalignment. The degree of tolerance depends upon the FSU and its motion requirements. Those FSUs with less demanding motion requirements (smaller workspaces) are more likely to accommodate greater misalignment errors.

In alternative embodiments, the superior vertebral plate and the inferior vertebral plate can be formed as part of the superior and inferior elements, for example, the cap-plate and socket-base of the chambered-ball embodiment, such that each previous pair of elements forms a single element. These alternate embodiments require no threading or lock screws and eliminate the modularity of the prosthesis. However, all the other features of the subject invention as discussed above can still be applicable to this alternate embodiment.

As noted above, the chambered-ball embodiment provides a modular prosthetic disc mechanism with up to six-degrees-of-freedom (6-DOF) throughout the FSU workspace. In a preferred embodiment, the modular prosthetic disc mechanism base element, the socket-base or socket element, consists of a right-circular cylinder with a spherical cavity with a radius of curvature r that depends on the overall size of the socket-base. In a preferred embodiment, a ring-bearing circles the lower interior spherical surface of the socket cavity to support a chambered-ball. The line from the ball-bearing centers on the socket ring-bearing to the ball center intersects the spherical surface of the ball at the bearing point of contact. Together, the socket and chambered-ball form a ball-and-socket joint that realizes the necessary three-dimensional orientation of the superior vertebra by the prosthesis. Alternate embodiments can utilize different external geometries for the socket-base, such as, but not limited to, elliptical, square, rectangular, and combinations thereof. However, the cavity that contains the chambered-ball or the area that supports or confines the chambered-ball must be able to produce three independent rotational degrees-of-freedom in the ball-and-socket joint formed with this element and a chambered-ball. Thus, in a preferred embodiment, the socket-base cavity is spherical.

The chambered-ball embodiment of the subject invention comprises a partially-spherical chambered-ball, which can be slightly larger than a hemisphere, which locks into a spherical cavity in the socket-base, that itself is also slightly larger than a hemisphere.

In a preferred embodiment, the chambered-ball also has one or more hydraulic portals for transferring, for example, lubricants, biocompatible saline solutions, combinations thereof, or other materials throughout the mechanism.

In a further embodiment, a girdle ring-bearing on the exterior surface of the chambered-ball, just below the chambered-ball's equator, rotates with the ball and provides a second ring-bearing for transferring loads from the chambered-ball to the socket-base. The girdle ring-bearing does not rotate out of the socket cavity, being blocked by a chambered-ball ring-bearing fastened inside the ball's cavity opening.

In one embodiment, the socket joint can be manufactured as two halves within which the chambered-ball is positioned before the two halves are sealed around the chambered-ball. In a further embodiment, the socket's spherical cavity and spherical ball share the same axis or center, but the socket has a slightly larger radius of curvature than the ball in order to allow for bearing gaps between the chambered-ball's spherical surface and the surface of the socket's spherical cavity.

In another embodiment, the ball and socket form a lower kinematic pair wherein the interfacing spherical surfaces form the joint bearings.

The chambered-ball embodiment of the subject invention can also utilize a piston 12 comprising a right-circular cylinder 66 (FIG. 11, FIG. 22) located within the cavity of the chambered-ball. Also, in a preferred embodiment, the chambered-ball possesses a right-circular cylindrical cavity for holding a piston of the same cross section, but of slightly smaller radius, to allow gaps for the piston and chambered-ball ring-bearings. The piston and chambered-ball form a cylindrical joint, in which the piston with a right-circular cylinder cross-section can rotate about its center axis within the ball. In a further preferred embodiment, the piston has the ability to telescope in and out of the chambered-ball cavity 35 (FIG. 9) to match the required intervertebral gap required by the position of the FSU. In an alternate embodiment, a piston with a non-circular cross section can be utilized with a chambered-ball cavity having matching cross sections. The chambered-ball and telescoping piston together create the polar-axis prismatic joint 115 (FIG. 12).

The piston itself preferably possesses a right-circular cylindrical cavity for mounting a machined helical spring for load management. The piston ring-bearing attaches to the end of the piston. At maximal flexion, the piston recesses into the ball cavity. At maximal extension the piston extends out of the ball cavity until the ring bearings interfere and prevent/oppose further extension. In other FSU configurations that include lateral bending and axial rotation, the piston can be at positions between these extremes.

The piston is comprised of a rigid material that can be, for example, titanium steel, titanium-carbide-coated stainless steel or cobalt-chromium-molybdenum alloy or from rigid, ultra-high-molecular-weight polyethylene, or combinations or alloys thereof.

Figure 11:
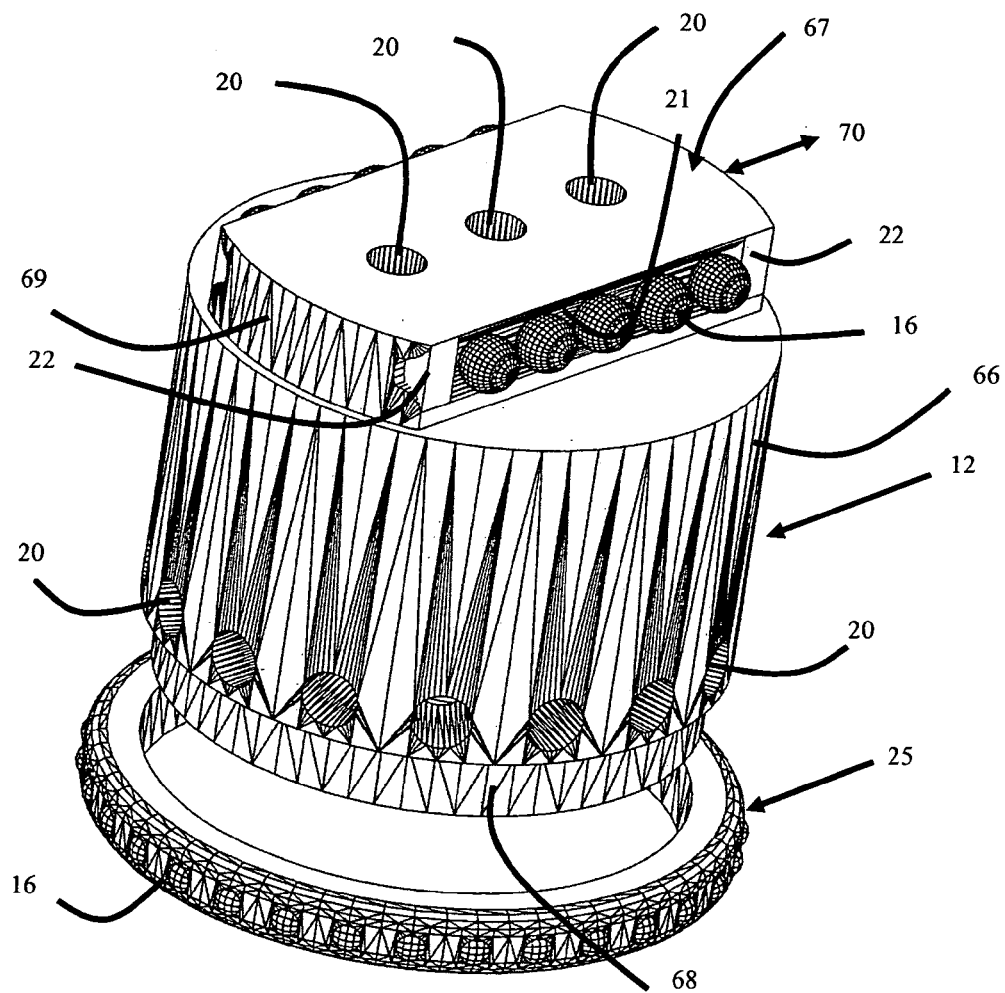
FIG. 11 shows an embodiment of the piston as a right-circular cylinder with ring-bearing and hydraulic portals. The hydraulic portals allow passage of fluid in and out of the piston cavity. The hydraulic portals at the top of the piston allow lubricating fluid to pass over the prismatic joints.
Figure 12:
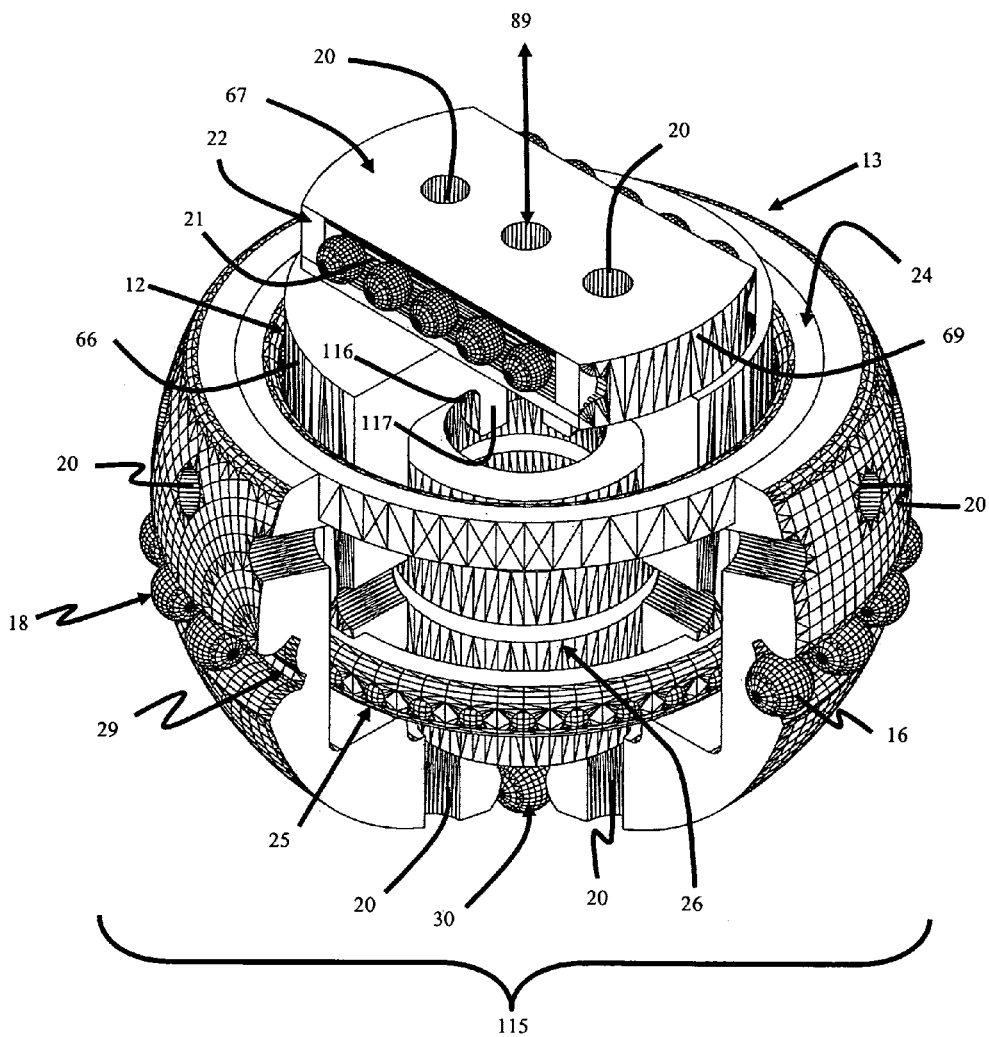
FIG. 12 illustrates the piston positioned within the chambered-ball to create the polar-axis prismatic joint.
Figure 13:
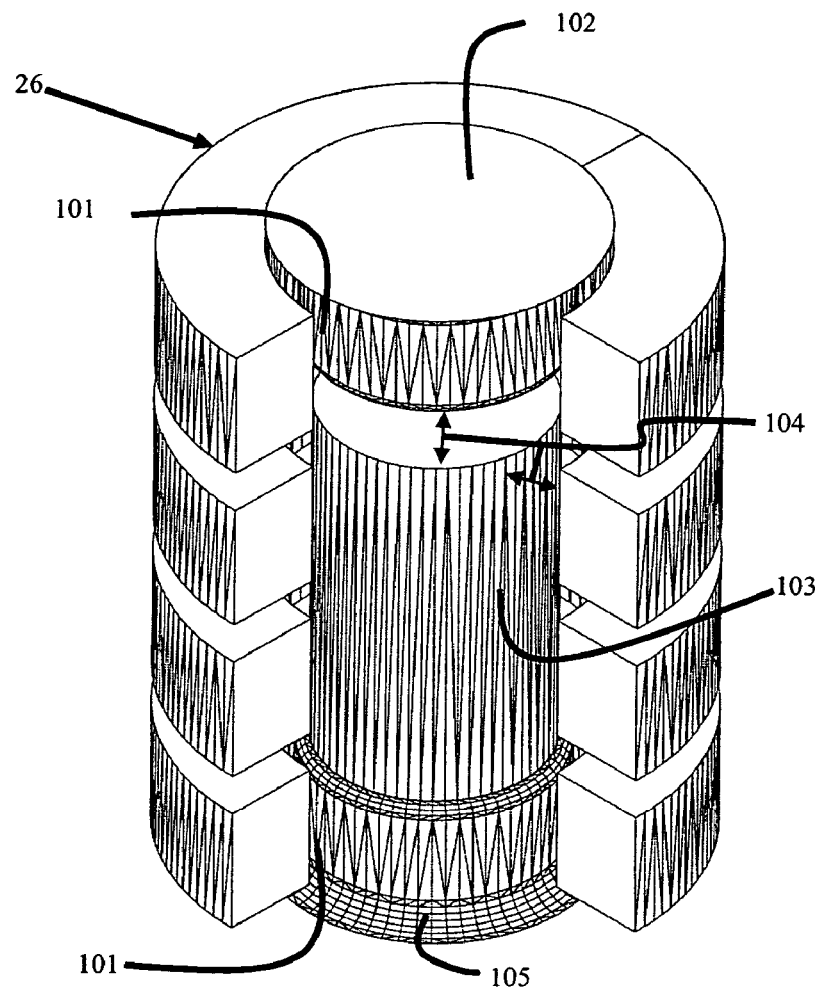
FIG. 13 stylistically depicts an embodiment of a threaded, helical spring. For certain embodiments of the subject invention, a fraction of the spring cavity can be filled with a compressible elastomer and/or hydrophilic gel to assist in shock absorption and compressive load bearing near the maximal compression configuration of the prosthetic devices.

In yet a further embodiment, the piston has a cylindrical cavity 83 (FIG. 22) to contain, for example, a spring, elastomeric device, or other shock absorbing material 26 (FIGS. 12 and 13). The lower element of the sagittal prismatic joint 67 (FIG. 11) with lateral bearing raceways 21, which can be machined, sits on top of the piston.

Hydraulic portals 20 (FIG. 11) surround the piston, in one embodiment, just above the piston ring-bearing, and one or more, preferably three, pierce the piston top. During movement of the FSU, the piston can pump lubricating fluid out of the piston cavity as the piston telescopes into the chambered-ball and can take or "pull" lubricating fluid into the piston cavity as it creates a negative pressure gradient in the piston core when it telescopes out from the chambered-ball. The number, size, and placement of hydraulic portals on the piston can affect fluid flow distribution, hydraulic damping, and shock absorption.

Combining the polar-axis prismatic joint with the ball-and-socket orienting joint produces a 4-DOF spherical joint 115 (FIG. 12) that orients the piston that then telescopes in or out as FSU motion requires. From spherical symmetry, this portion of the prosthesis is capable of orienting the piston at any sagittal, frontal, and axial angles and positioning the piston at any radius within the piston stroke distance.

A further preferred chambered-ball embodiment, utilizes two dual-track, orthogonal linear bearings to produce two further, orthogonal, independent translational degrees-of-freedom, referred to as the lateral prismatic joint and the sagittal prismatic joint. These two prismatic joints define an imaginary plane of motion called the superior vertebral plane, which is fixed in the superior vertebral plate and always orthogonal to the polar axis. In a preferred embodiment, three elements with dual-track linear raceways assemble to form the sagittal and prismatic joints: the cap-plate is fixedly attached onto the plane-bearing guide that is fixedly attached onto the piston sagittal bearing support. For all motions the prosthesis maintains the bottom surface of the plane-bearing guide parallel to the moving superior vertebral plane whose motion the FSU generally dictates.

In a preferred embodiment, the prismatic joint dual tracks resist moments of force to provide smoother operation and joint stability. In the presence of external forces, the chambered ball-and-socket joint and polar-axis prismatic joint orient and position this imaginary superior vertebral plane to keep it fixed relative to the superior vertebra. The combined action of the sagittal and lateral prismatic joints allows a fixed point in the superior vertebral plane to slide into any position in that plane dictated by natural FSU motion.

In yet a further embodiment, ball- or rod-bearings can be utilized with the prismatic joint raceways to couple the two raceway elements: the cap-plate and the plane-bearing guide for the lateral prismatic joint, and the plane-bearing guide and the piston for the sagittal prismatic joint; thus, integrating and linking all three elements together.

To clarify by way of example, the plane-bearing guide essentially hangs from the cap-plate and the piston essentially hangs from the plane-bearing guide with bearings locking the elements together.

The raceway bearing can utilize, for example, spherical, cylindrical, or rod bearings and comprise, for example, titanium steel, titanium-carbide-coated stainless steel, thermoplastic, various plastics, glass, or other durable, rigid material or combinations or alloys thereof. In addition, rod-bearings can utilize different cross-sectional shapes to effect lubrication flow and bearing contacts. The raceway can also utilize materials that maximize interface with the bearings. Linear bearing stops and separators can assist with maintaining proper ball-bearing position, but rod-bearings usually do not require separators.

Alternative styles of rod-bearings (Fig. A, B, C, D) can be used to replace ball-bearings in the prismatic joints. For example, linear bearings that do not roll but have different contact surfaces, resulting from different choices of cross-sections and lateral surface shapes can be utilized. Such linear bearings can also have grooves for lubrication flow along the length of the bearing. In circular form, they can also be used to replace the ring bearings in the subject invention.

Additional embodiments utilize bearing stops that extend a sliding member of a prismatic joint to reduce the amount of translation motion from the maximum since the extended bearing-stop can impact the skirt of the cap-plate of the prosthetic disc linkage before the sliding member does. In a preferred embodiment, the cap-plate skirt limits the maximum range of motion of both the sagittal and lateral prismatic joint. However, if the maximum permissible workspace must be reduced for clinical or other reasons, oversized linear bearing stops can be utilized. For example, if a patient must restrict lateral bending of the spine at the site of the prosthesis, the lateral prismatic joint bearing stops can be made large enough to limit translation in the left or right lateral direction by independent amounts. In like manner, oversized bearing stops on the sagittal prismatic joint limit flexion and extension by independent amounts. Bearing stops, therefore, can provide a means to control the amount of workspace volume realized by the prosthesis.

For flexion and extension, the sagittal prismatic joint and the polar-axis prismatic joint together allow translation of the superior vertebral plate in the sagittal plane while rotating it about the sagittal axis. The lateral prismatic joint does not enter into pure flexion and rotation movements. For pure lateral bending, the polar-axis and lateral prismatic joints provide the joint motion components while rotating about the lateral axis with the piston. Natural lateral motion of the cervical spinal generally includes some axial rotation, motion to which the device automatically accommodates. In each case, the spherical joint automatically rotates and extends or retracts the piston according to the forces exerted on the prosthesis.

The lubricating fluid and/or colloidal suspension contained within the prosthetic device of the subject invention by the boot seal, can be pumped or otherwise moved around the elements of the device by the piston during spinal motion, which tends to separate all the interacting bearing surfaces in a manner similar to the action of synovial fluid in a diarthrodial joint; this can increase the efficiency of the bearing surface, reduce wear, and/or provide compressive resistance and motion dampening to the moving elements within the device.

A yet further chambered-ball embodiment includes a rotating, helical central-spring with, for example, an undersized elastomer or hydrophilic-gel core (Bao and Higham's hydrogel, U.S. Pat. No. 5,192,326, provides shock absorption under impulsive loads, acting much like the nucleus pulposus of a natural disc) for controlling or managing static and dynamic loads near maximum flexion. These load-bearing elements, in a preferred embodiment, fit into the right-circular cylinder cavity of the piston to control maximal compression. Inside threading on the top and bottom of the helical spring provides a means of screwing the spring to threaded mounting posts on the ceiling of the piston cavity and the floor of the chambered-ball cavity. However, those with skill in the art will recognize that other means of securing the spring can be utilized. Thus, the spring, a flexible load bearing mechanism, is the element that links the piston to the chambered-ball.

In an alternative embodiment, the piston itself can be modified so as to mimic the helical spring with threads at its base that protrude much like the piston-ring bearing. This protrusion can create a bearing gap between the piston and the chambered-ball lateral surface. A matching threading at the bottom of the chambered-ball cavity allows the piston to screw into the chambered-ball cavity. In a further alternative embodiment, the outer/exterior, lateral, helical surface of a piston configured as a helical spring can also be configured with rounded, protruding edges to provide bearing surfaces that slide over the smooth, chambered-ball cavity lateral surface. This embodiment eliminates the need for piston and chambered-ball ring-bearings, because the helical piston-spring can maintain joint connection integrity because the piston base is able to screw into the bottom of the chambered-ball cavity.

In a preferred embodiment, the rotating, helical central-spring, as described above, is able to provide a balancing force to nominal gravitational loading in the neutral position of the FSU. Somewhere between neutral and maximum extension, for example, at approximately halfway, the spring attains an unloaded state. From that point to maximum extension, the spring then opposes the extension motion and stretches. The spring reaches greatest compression in maximum flexion and greatest extension in maximum extension of the FSU.

In an even further embodiment, the spring can provide different spring constants in series or even non-linear spring characteristics to match application load requirements. Since the piston constrains the spring to align with the polar-axis of the ball-and-socket, regardless of relative vertebral orientation or position, external forces principally act along the length of the spring or cause joint motion, which can be a desirable feature. Thus, in this embodiment, non-polar external forces acting on the prosthesis can cause the mechanism to orient itself so as to align the piston top surface with the superior vertebral plane as it moves under muscle control. The spring is able to balance central forces in a spherical robot and prevent/oppose the collapse of the mechanism under load. Proper spring design can also accommodate the various intervertebral distances required during FSU motion, which can eliminate excessive forces on the facet joints in the process.

Forces acting on the prosthetic disc linkage move the various prismatic and orienting joints allowing them to follow the natural motion of the superior vertebra with respect to the inferior vertebra of an FSU. Generally, forces acting on the superior vertebral plate decompose into a force tangent to the defining sphere of the chambered-ball and a force directed along the polar-axis of the ball. The former force provides rotational motion of the chambered-ball in its socket and the latter force provides a compression or extension load on the load-bearing system, regardless of the complexity of the superior vertebral motion.

A further embodiment of the device of the subject invention exhibits flexion and extension in only the sagittal plane. Thus the socket-base cavity can be devised as a right-circular cylinder with its principal axis aligned with the sagittal axis and with two ring-bearings, one at each end of the cylinder. In this embodiment, the "chambered-ball" becomes a chambered-cylinder with a piston and sagittal prismatic joint, providing a total of 3-DOF, all that is necessary for arbitrary position and orientation in the sagittal plane only. If the chambered-cylinder cavity is a right-circular cylinder as in a preferred embodiment, then there follows a fourth degree of freedom that allows axial rotation. In this embodiment, the plane-bearing guide and cap-plate integrate into a single unit with only bearing supports for the sagittal prismatic joint.

Figure 28:
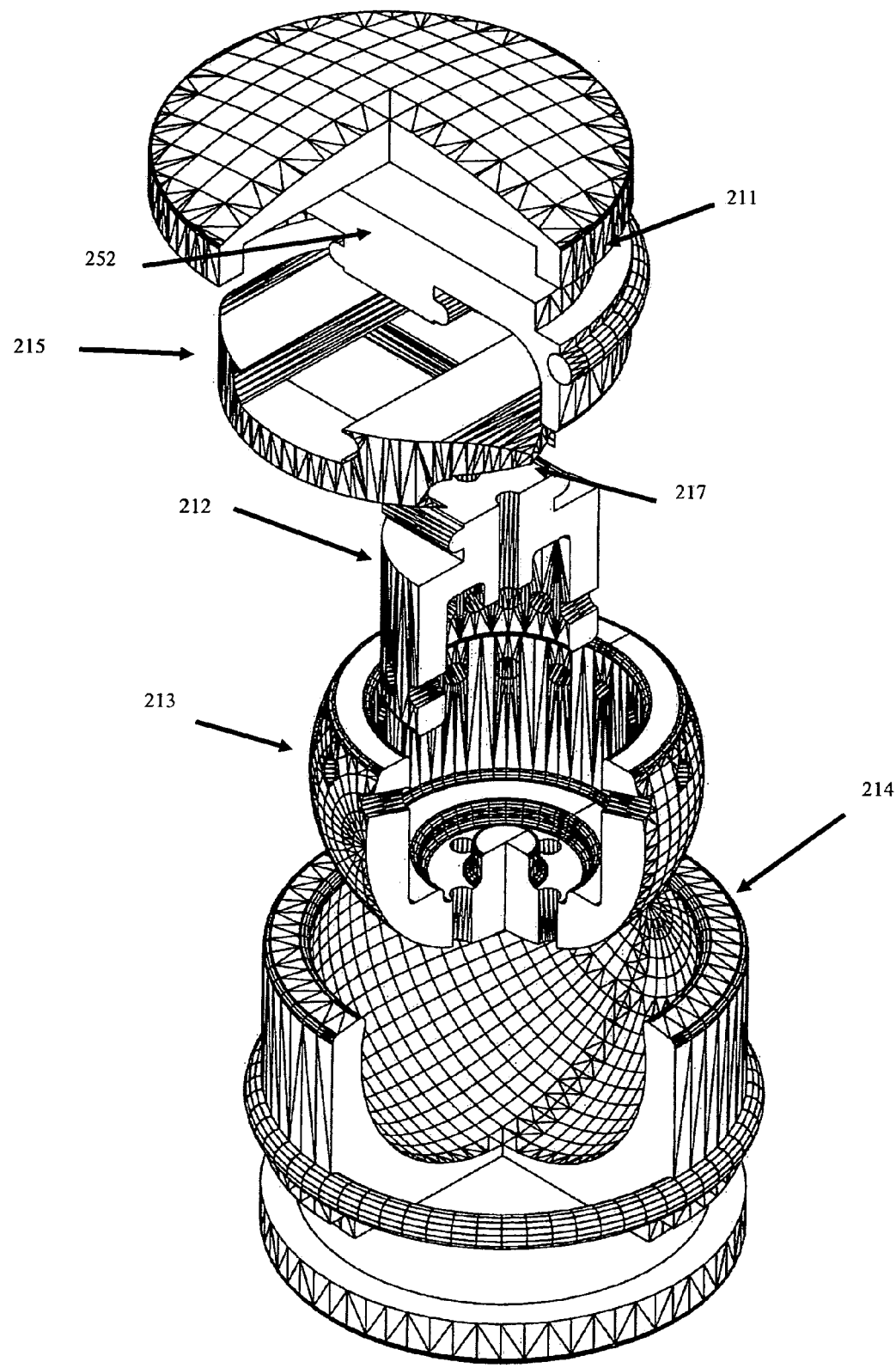
FIG. 28 illustrates the chambered-ball embodiment of the invention using only lower pairs for all joints, making it a true 6-DOF linkage as opposed to 6-DOF mechanism illustrated in alternative multi-point or line contact bearings. This embodiment employs surface contacts for all joints. An alternative of this embodiment can employ a mix of surface, line, and point contact bearings for the motion interfaces.
Figure 29:
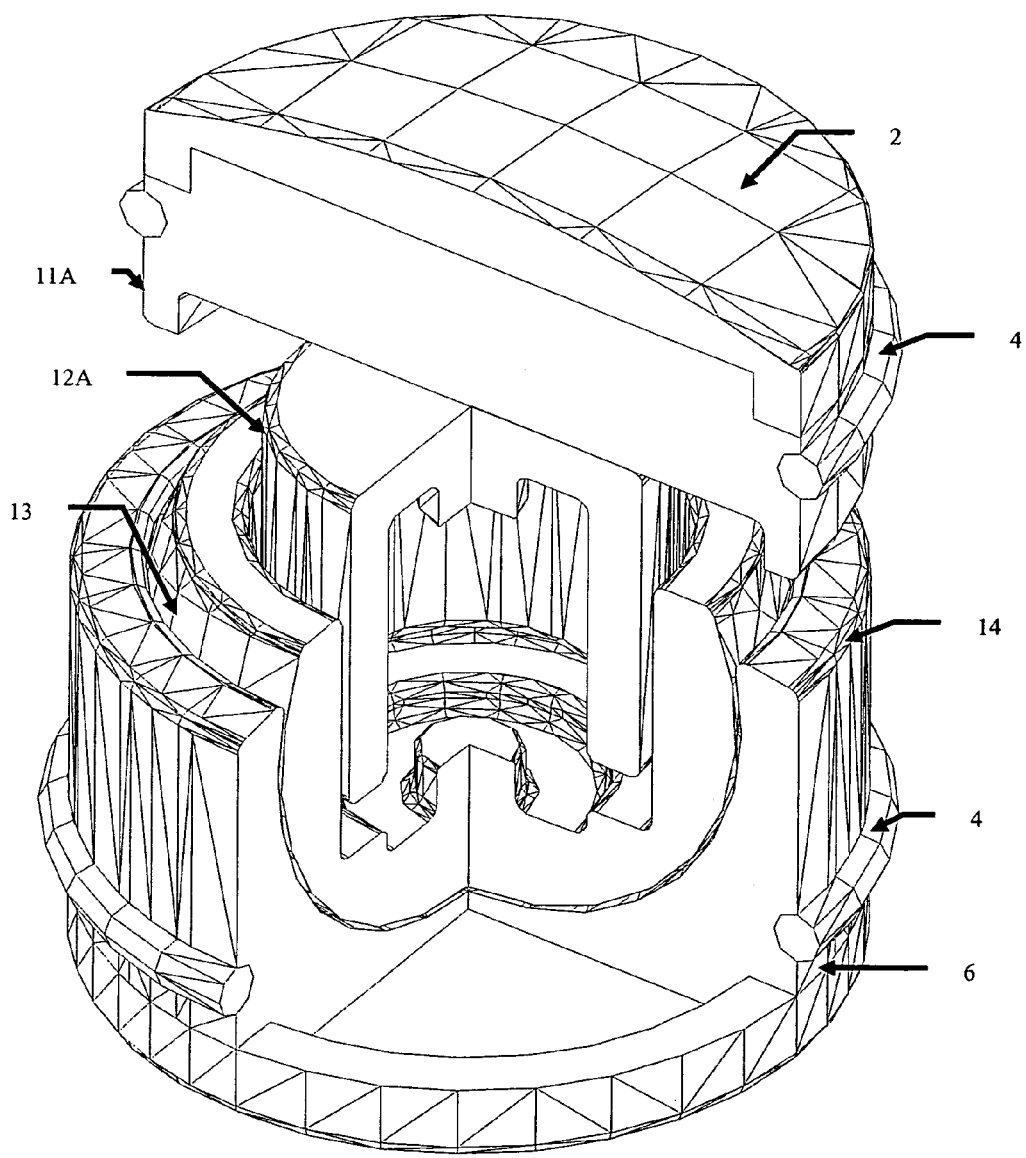
FIG. 29 illustrates a cut-away view of the embodiment shown FIG. 28 with the components assembled.

A further alternative of this embodiment utilizes lower kinematic pairs for all joints (FIG. 28). This alternate embodiment eliminates or reduces the use of ball- and rod-bearings, replacing some or all of them with surface bearings. To facilitate motion, both surfaces of a pair are, for example, but not limited to, tough thermoplastic bearing material or titanium or other hard, low friction biocompatible material or combinations thereof. By way of further example, the cap-plate, piston and socket-base can comprise for example, titanium-carbide-coated stainless steel, and the plane-bearing guide and chambered-ball can further comprise for example, a suitable thermoplastic. Another example is that all elements but the superior and inferior vertebral plates are thermoplastic bearing material. These alternative embodiments can increase friction in the joints that can reduce muscle stress, facilitate easier construction, require fewer parts, and provide a more robust device capable of managing greater loads.

Embodiments of these spatial mechanisms can differ from each other at various levels of the spine, primarily in engineering design choices regarding materials (for example, but not limited to, titanium steel, titanium-carbide-coated stainless steel, cobalt-chromium-molybdenum alloy, polyurethane, high-molecular-density polyethylene, biologically derived materials and alloys or combinations thereof), size, strength, thicknesses, and so forth. The configuration, interaction, geometry, kinematics and shape of the basic structural elements that generate the motion, apply equally along the spine.

The foregoing general discussion of the devices of the chambered-ball embodiment of subject invention can be further illuminated by reference to the detailed drawings provided herein. Therefore, this embodiment of the invention will now be described in more detail, and with reference to parts that are illustrated in the accompanying figures. The general details regarding the mechanisms of the chambered-ball spinal disk prosthesis embodiment can also be applicable to alternative spinal disk prostheses embodiments that will be discussed below.

Figure 10:
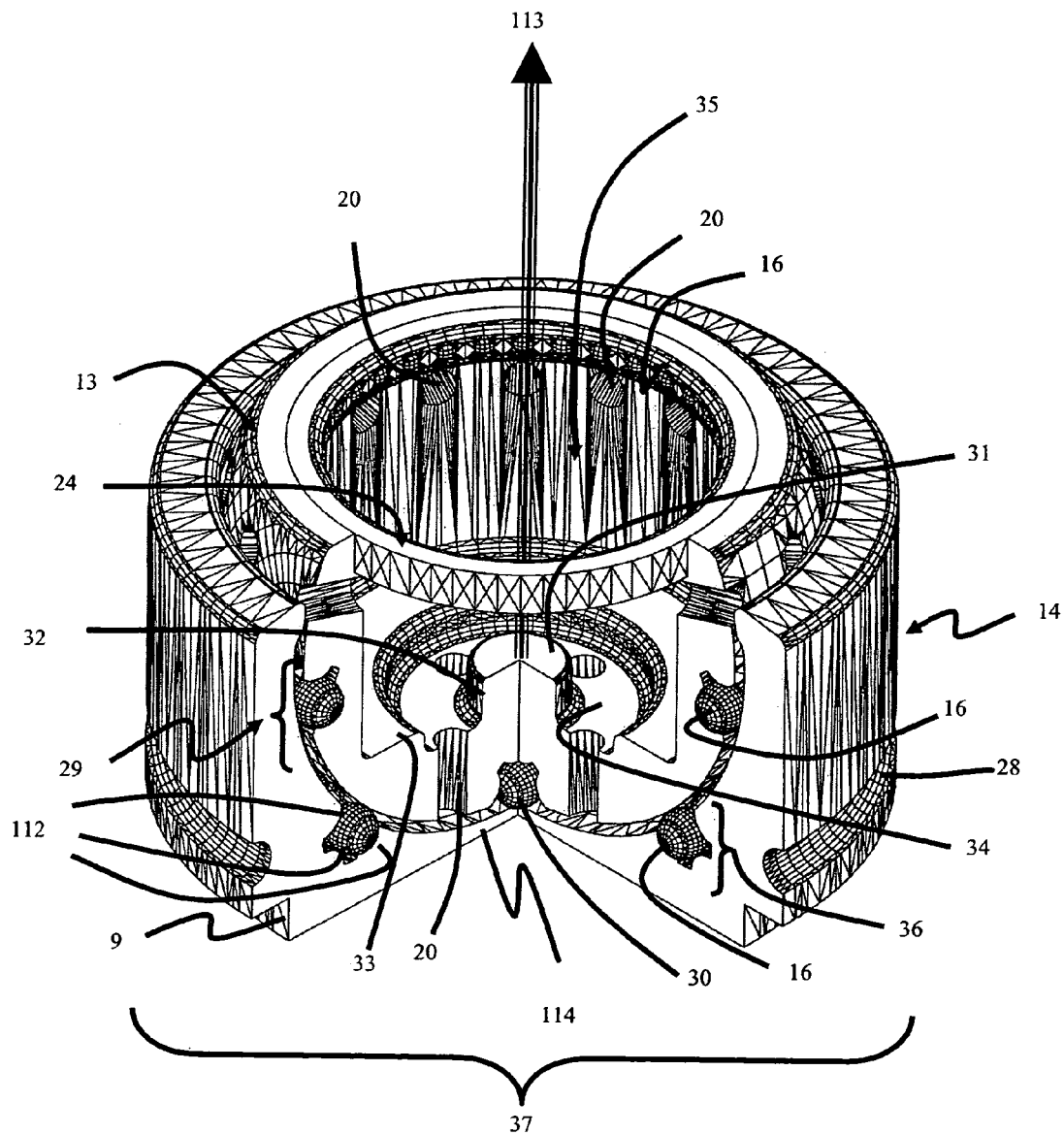
FIG. 10 illustrates a cut-away view of the chambered-ball and the socket-joint and shows the placement of the chambered-ball within the socket cavity and the arrangement of the girdle, socket-base, and chambered-ball ring-bearings. The chambered-ball and the socket-base combined form an essentially spherical joint.
Figure 21:
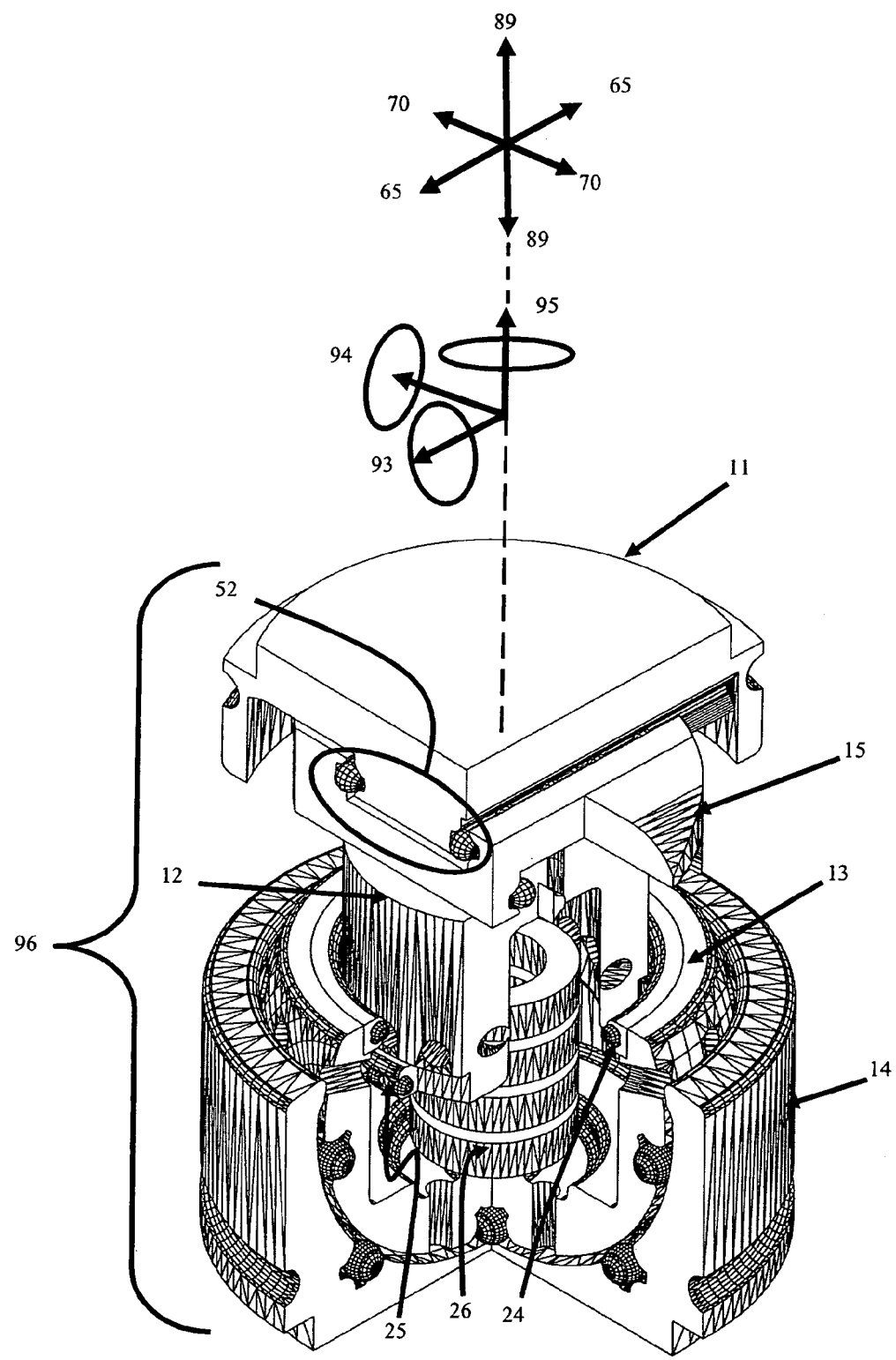
FIG. 21 illustrates the chambered-ball embodiment wherein all the joint mechanisms of the modular 6-DOF spatial mechanism for human disc prosthesis can be seen with a cut-away view.

As noted above, the chambered-ball spatial mechanism for spinal disc prosthesis of the subject invention provides up to six-degrees-of-freedom of motion throughout the natural workspace of a functional spinal unit (FSU). The mechanism comprises at least three orthogonal prismatic joints; sagittal 17 (FIG. 19), lateral 52 (FIG. 19) and polar-axis 115 (FIG. 12); and one ball-and-socket joint 37 (FIG. 10). The ball-and-socket joint 37 provides up to three degrees-of-rotational-freedom equivalent to combined axial 95, sagittal 94, and frontal 93 plane rotations (FIG. 21). The three orthogonal prismatic joints allow arbitrary positioning in the FSU workspace.

Figure 17:
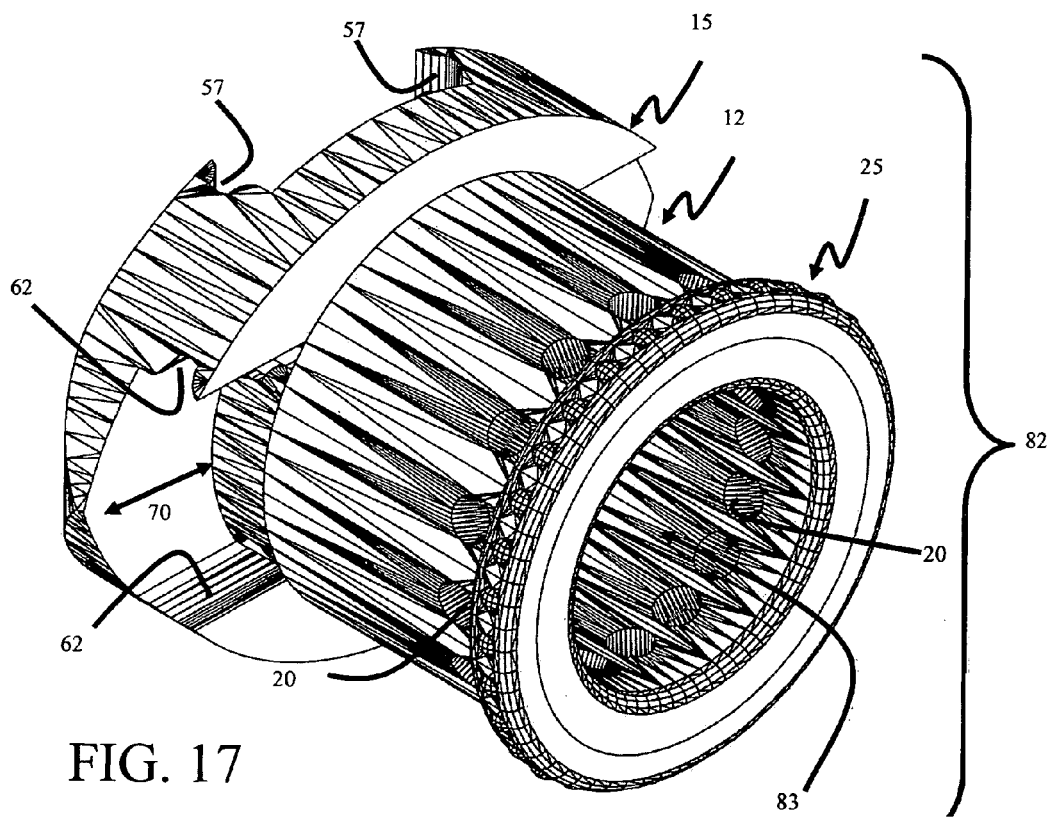
FIG. 17 shows the plane-bearing guide fitted with the piston to form the sagittal prismatic joint.

In a preferred embodiment, the device of the subject invention supports hydraulic lubrication, shock absorption, and damping. In one embodiment, a helical spring 26 (FIGS. 12, 13 and 14) can be used in conjunction with hydraulic damping to provide compression and extension loading and shock absorbing capabilities. In another embodiment, a spring can be installed into the piston cavity 83 (FIG. 17). In still a further embodiment, a boot 5, 107 (FIG. 2, FIG. 3A and FIG. 3B) provides additional torsion and extension loading response. The boot can comprise, for example, a tough, flexible, fiber reinforced elastomer matrix (FIG. 2).

FIG. 2 depicts the anterior view of a completely assembled, modular, six-degrees-of-freedom (6-DOF) spinal mechanism 1, 106 (FIG. 2) in a neutral position. The superior vertebral plate element 2 and the inferior vertebral plate element 6 fuse to the corresponding superior vertebra and inferior vertebra of the FSU in which a surgeon inserts the prosthesis. A tough, flexible corrugated boot, which can be, for example, cylindrical 5 or spherical 107 in shape, attaches to the unit with, for example, clamping rings or bands, various applicable adhesives, pins, screws, elastic means, or combinations thereof.

Figure 2A:
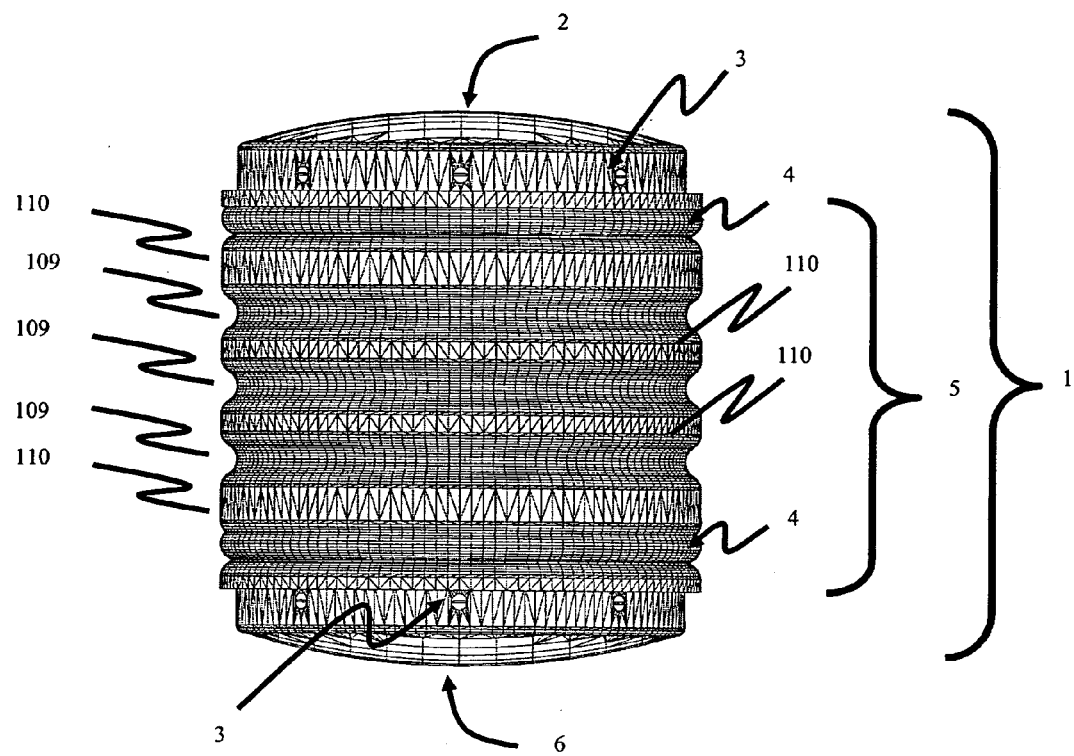
FIGS. 2A and 2B illustrate an anterior view of two embodiments of completely assembled chambered-ball spinal disc prosthesis.
Figure 2B:
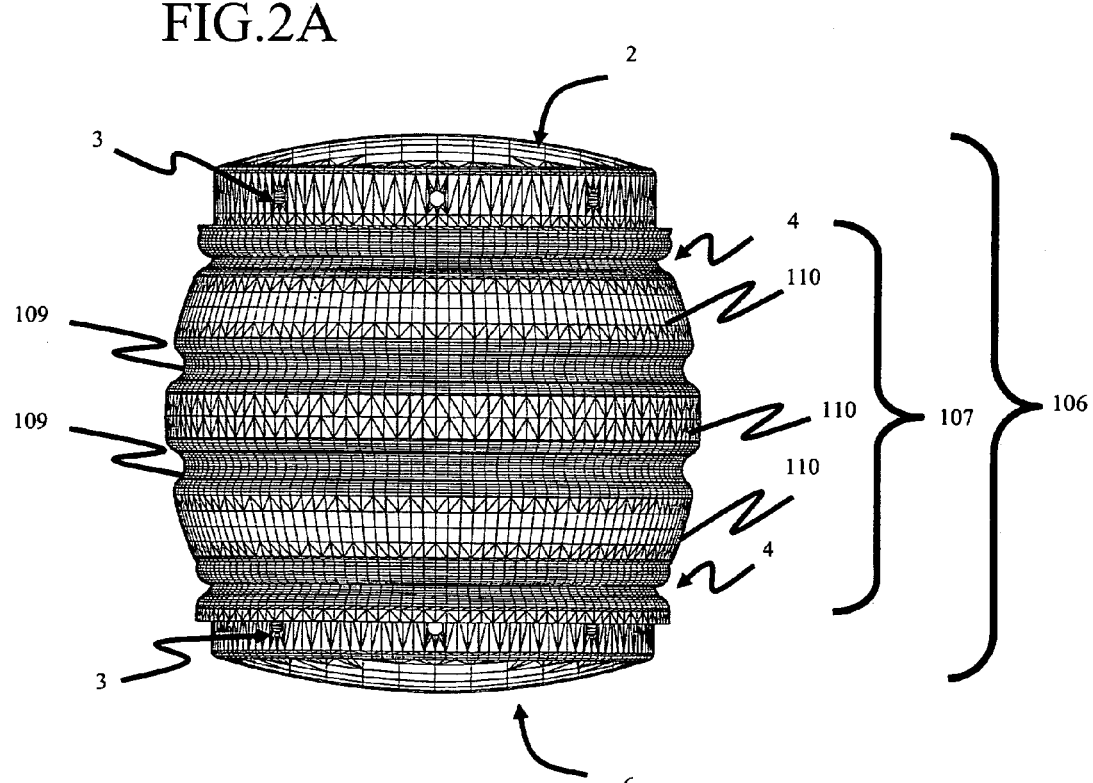

In one embodiment, the boot is fixedly attached to the device by means of clamping rings 4 FIG. 2A. In a further embodiment, the boot structure comprises a fiber reinforced diagonal weave that can be embedded into a low durometer, flexible elastomer matrix with alternating tough, thick segments 110 separated by more elastic, thinner segments 109. Between maximum flexion and maximum extension the anterior surface of the boot varies in length up to about 40% while the posterior surface varies up to about 20%. In a preferred embodiment, the boot has higher density fiber belts in regions 110 to make those regions tougher and less flexible than regions 109 (FIG. 2A, FIG. 2B). With this construction the boot is able to open and close in a billows-like fashion, yielding mobility in all directions while assisting in the maintenance of prosthesis integrity.

Figure 3A:
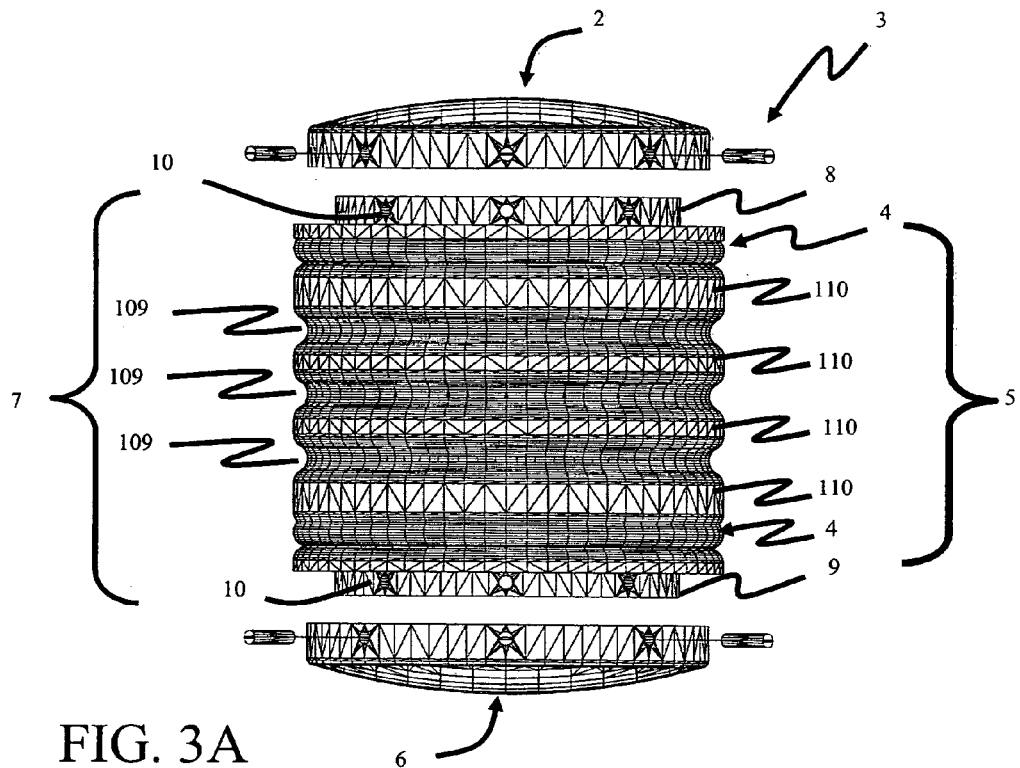
FIGS. 3A and 3B show the chambered-ball embodiment wherein the vertebral plates are disengaged from the modular prosthetic disc linkage to indicate how the latter can form a replaceable, independent unit or module.
Figure 3B:
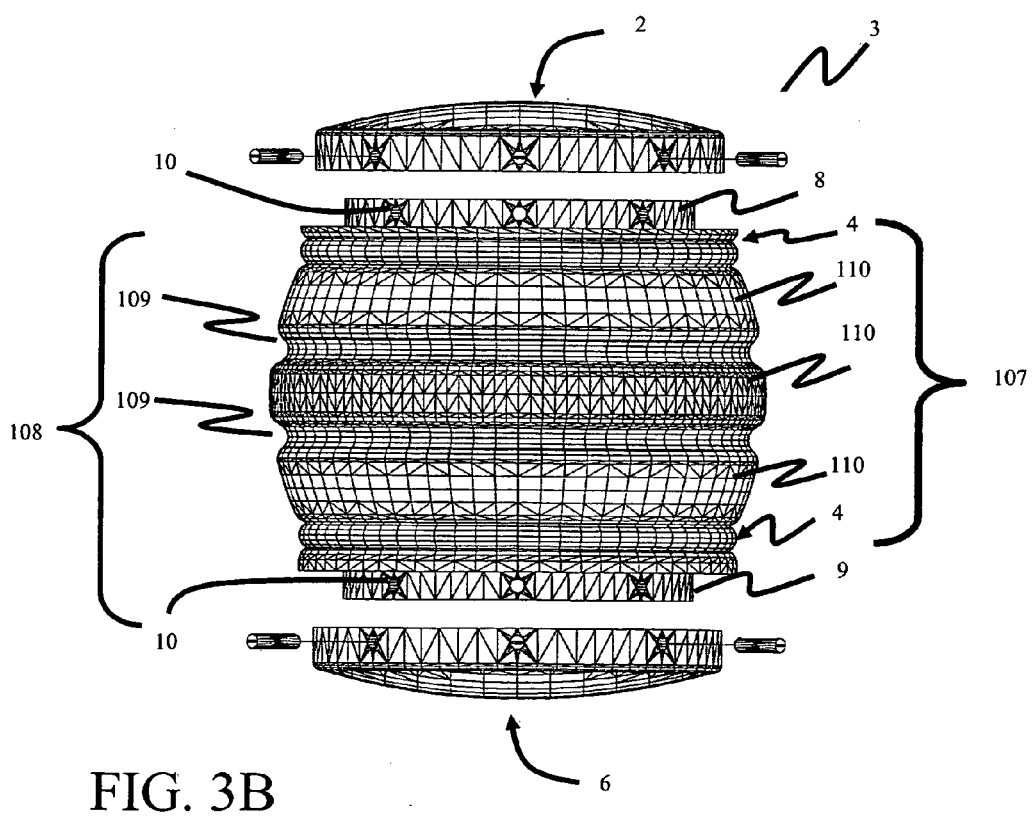
Figure 4:
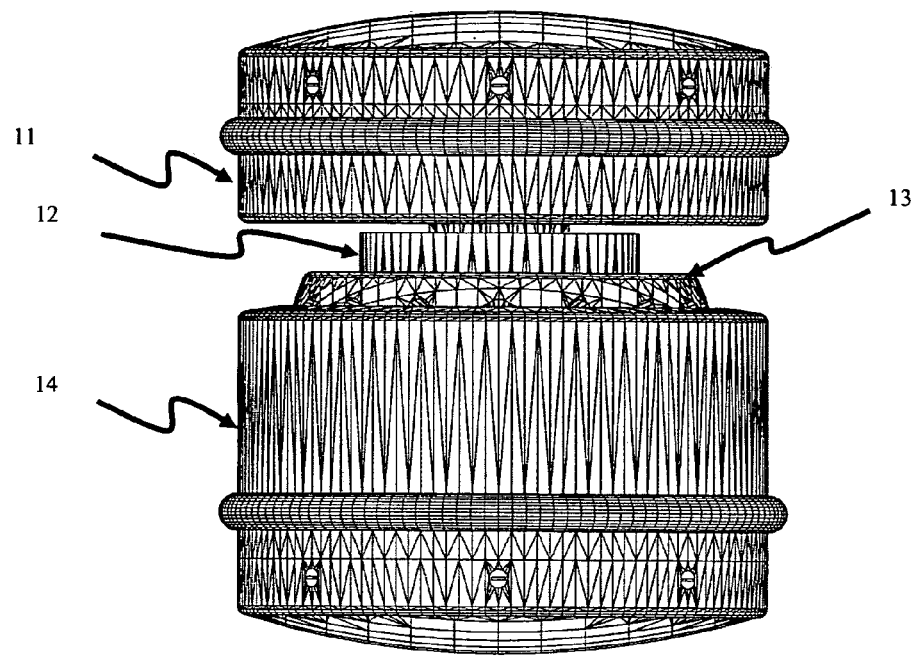
FIG. 4 shows chambered-ball embodiment wherein the boot is removed from the prosthesis to reveal the cap-plate, piston, chambered-ball and socket-base of the embodiment.
Figure 9:
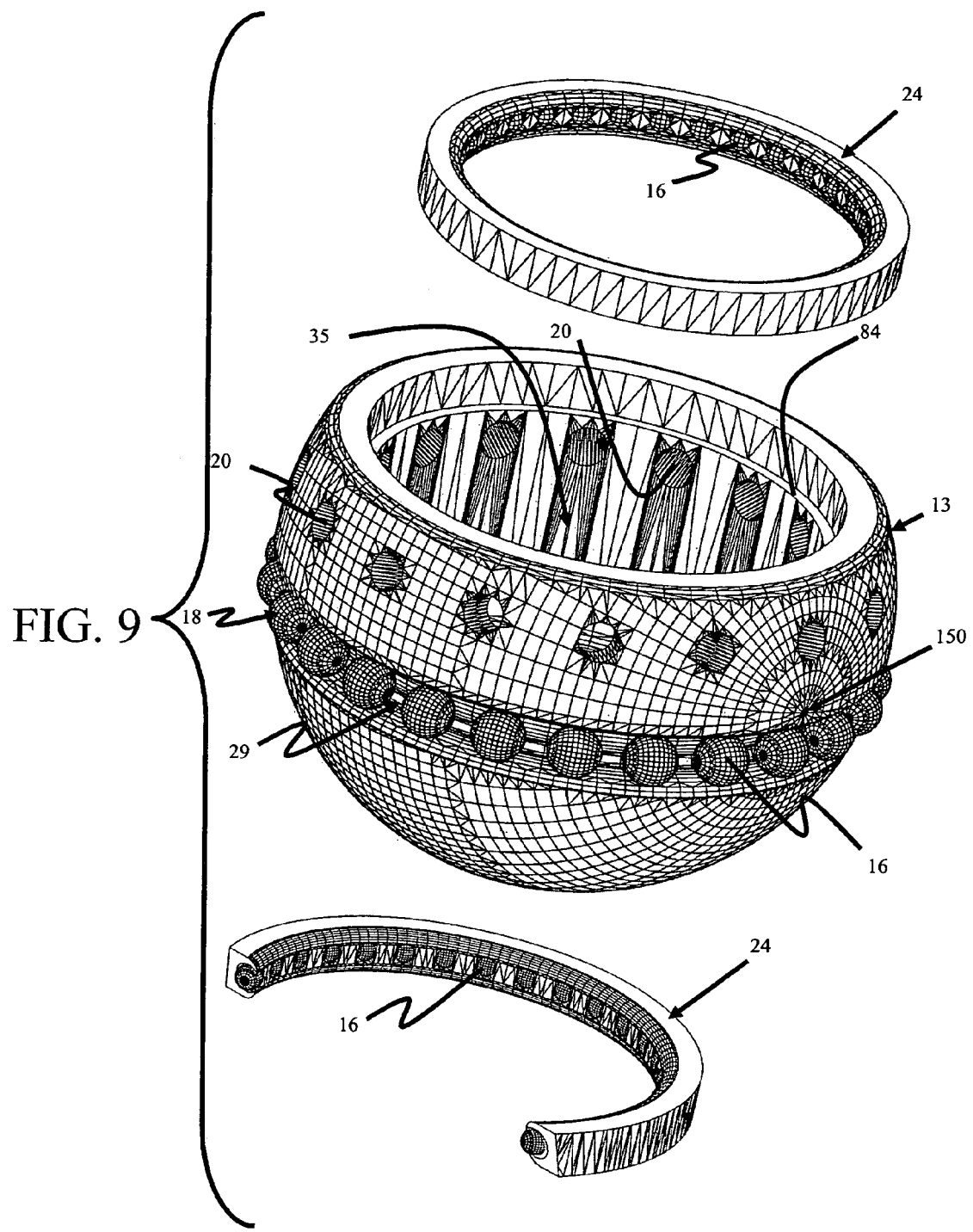
FIG. 9 shows an embodiment of the chambered-ball prosthesis utilizing a spherical chambered-ball, which is slightly larger than a hemisphere with a right-circular cylindrical cavity for containing a piston. Also shown in FIG. 9 are the girdle ring-bearing and the hydraulic portals around the mouth of the chambered-ball.

FIGS. 3A and 3B highlight the modular aspect of one embodiment of the prosthesis of the subject invention: a modular prosthetic disc mechanism 7, 108 screws into, or otherwise firmly, but reversibly, attaches, to the vertebral plates 2, 6. To effect joining the modular prosthetic disc mechanism 7, 108 to the vertebral plates, one embodiment utilizes a threaded projection 8 on the cap-plate 11 (FIG. 7A) that engages with threaded lips 43 within the superior vertebral plate 2 (FIG. 6A) and threaded projection 9 on the socket-base 14 (FIG. 7A) engages with threaded lips within the inferior vertebral plate 6 (FIG. 6B). In a further embodiment, the threading on the cap-plate 11 and superior vertebral plate 2 possess opposite threading sense of the socket-base 14 and inferior vertebral plate 6 to allow screwing the modular prosthetic disc mechanism 7, 108 into both vertebral plates simultaneously with the same turning action FIG. 4, with the boot 5 (or 107) removed, reveals an anterior view of the cap-plate 11, socket-base 14, and partial views of the piston 12 and chambered-ball 13. Removal of the cap-plate 11 and socket-base 14 in FIG. 5 further exposes the spherical chambered-ball 13 and a further element, the plane-bearing guide 15. In one embodiment, the chambered-ball 13 possesses hydraulic portals 20 in a circle of latitude above the equator near the mouth of the chambered-ball cavity 35 (FIG. 9). In a further embodiment, there are four other hydraulic portals 20 at the base of the chambered-ball 13 (FIG. 10). In yet a further embodiment, the four hydraulic portals are distributed 90 degrees apart at the base of the chambered-ball. These hydraulic portals 20 allow the passage of any lubricating fluid and/or colloidal suspensions in and out of the chambered-ball cavity to lubricate the bearing surfaces, contact points and lines as the ball rotates and/or provide compressive resistance and motion dampening to the moving elements within the device.

The superior 2 and inferior 6 vertebral plates (FIG. 6) of the device can be identical in structure and composition. In one embodiment, at least one surface of a vertebral plate is convex 38, further comprising a recessed, flat underside 39 (FIG. 6B) with a rim or lip 40. The cavity 44 of each vertebral plate matches the threaded mounting extensions of the cap-plate 11 and the socket-base 14. Threads on the inside surface of the lip 43 possess a different turning sense on the superior 2 and inferior 6 vertebral plates so that the superior plate 2 screws onto the cap-plate 11 and the inferior plate 6 screws onto the socket-base 14 with the same turning motion. One or more, preferably three, through-holes 41 in the anterior surface of each vertebral plate rim 40 allow for the insertion of, for example, lock-and-align screws 3 through the rim of the plates. These screws fasten into the threaded holes 10 (FIG. 7A) on the cap-plate 11 and socket-base 14.

In a further embodiment, central-anterior through-holes on the superior and inferior vertebral plates define a line that lies in the sagittal midline plane. The angle of that line with its projection onto the horizontal plane facilitates orientation of the prosthesis in the FSU. The x-y coordinates of the chambered-ball center in the sagittal midline plane, is dictated by the geometry of the FSU utilizing the prosthesis. With the lock-and-align screws in place, the modular prosthetic disc mechanism 7, 108 is properly oriented with respect to the vertebral plates 2, 6.

In one embodiment, the vertebral-plate has a roughened spherical surface 38 and consists of titanium alloy with a porous matrix for bone infusion. The spherical center and solid angle subtending the spherical surface are, in a preferred embodiment, alterable design parameters that dictate the size of the vertebral top surface. In a further embodiment, the vertebral plates comprise cobalt-chromium-molybdenum alloy with vertical teeth as well as a porous mesh on the spherical surface to further enhance bone infusion and mechanically securing the plates to bone.

Figure 8:
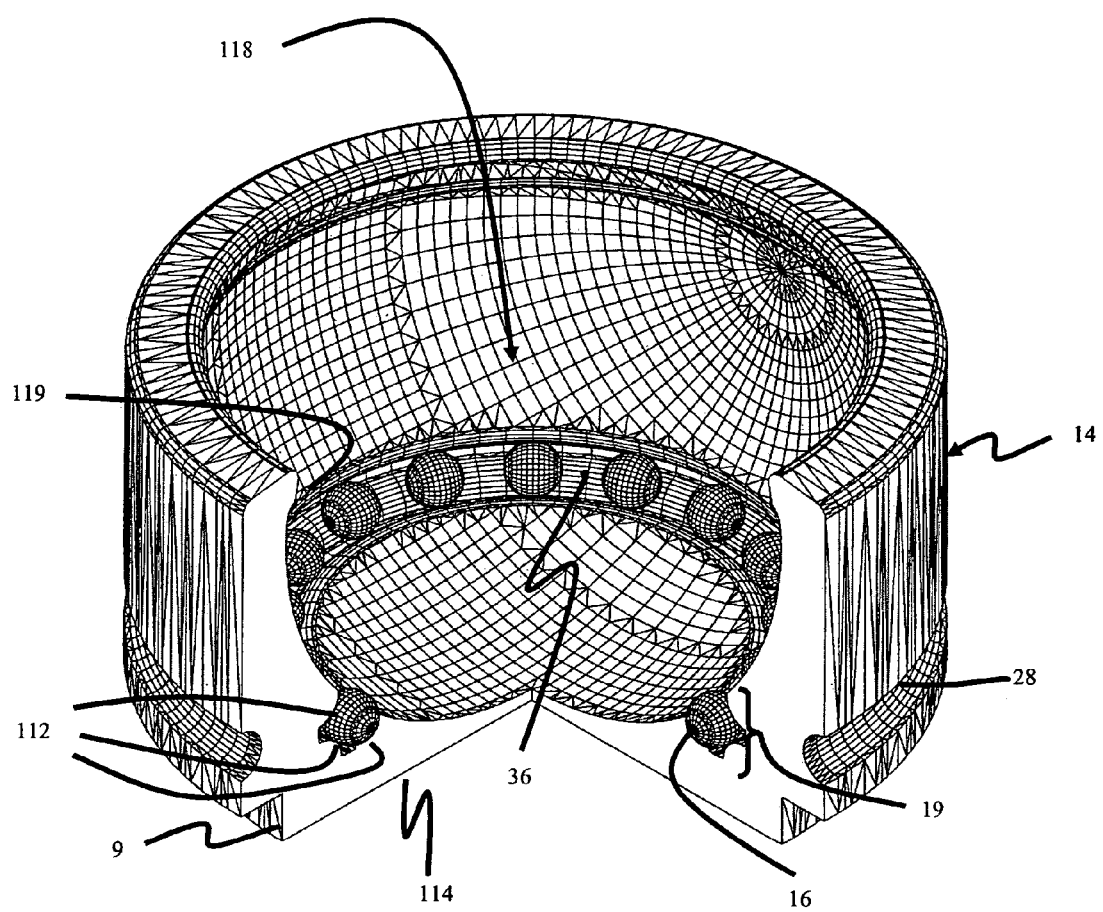
FIG. 8 is a cut-away view of the socket-base of the chambered-ball embodiment of the subject invention, which reveals the spherical cavity that, in a preferred embodiment, contains the chambered-ball. The socket ring-bearing supports the chambered-ball and can reduce friction between the ball and socket.

A non-reactive, biocompatible liquid gasket can also be applied to one or more threaded surfaces, for example surfaces 8, 9, and 10 and other interface surfaces before mating the modular prosthetic disc mechanism 7, 108 with the vertebral plates 2, 6 in order to seal and protect elements of the prosthesis from chemical reaction with the bio-environment. The interface surfaces consist of 1) the recessed, flat section of the superior vertebral plate 39 and the flat surface on top of the cap-plate 51 (FIG. 18B) and 2) the recessed flat portion of the inferior vertebral plate 39 and the flat bottom of the socket-base 114 (FIG. 8). The utilization of gasket seals protects the interfaces and threads from corrosion, degradation, and molecular bonding, making modularity of the modular prosthetic disc mechanism realistic.

Following are specific Examples of the design, construction and/or operation of various components of the system of the subject invention. These examples should not be construed as limiting. Also certain general features described can be applicable to alternative embodiments that will also be discussed below.

EXAMPLE 1

Ball-and-Socket Joint

In one embodiment, the chambered-ball 13 (FIG. 9) fits into the spherical cavity 118 of the socket-base 14 (FIG. 8) to form a ball-and-socket joint 37 (FIG. 10). In a preferred embodiment, the ball is free to rotate about three orthogonal axes 93, 94, and 95 (FIG. 14) within the socket cavity. Thus, in one embodiment, the ball-and-socket joint allows the spatial mechanism to arbitrarily orient or point in three-dimensional space, within the angle limits of the linkage, the more distal elements of the device: the piston 12, plane-bearing guide 15, cap-plate 11, and superior vertebral plate 2. In the lower pair embodiment, FIG. 28, the elements 214, and 213 form a spherical kinematic pair, i.e., the ball-and-socket joint.

Figure 5:
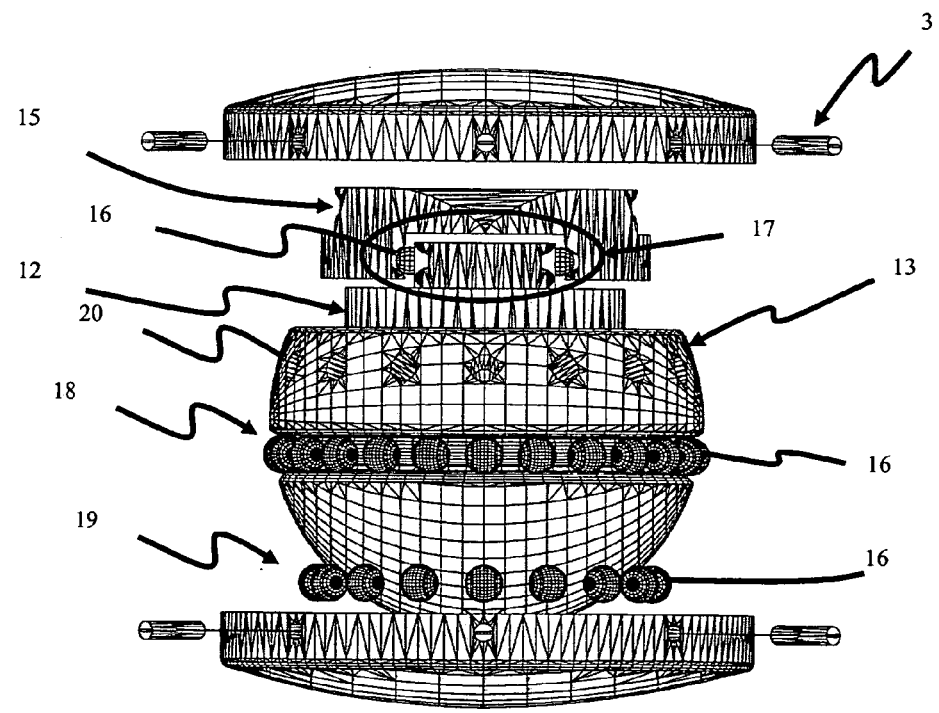
FIG. 5 further illustrates the embodiment shown in FIG. 4 with the cap-plate and socket-base removed to further reveal the spherical shape of the chambered-ball and to expose the plane-bearing guide that can be used to support the lateral and sagittal prismatic joints of the mechanism. The figure also exposes the girdle and socket-base ring-bearings.
Figure 6A:
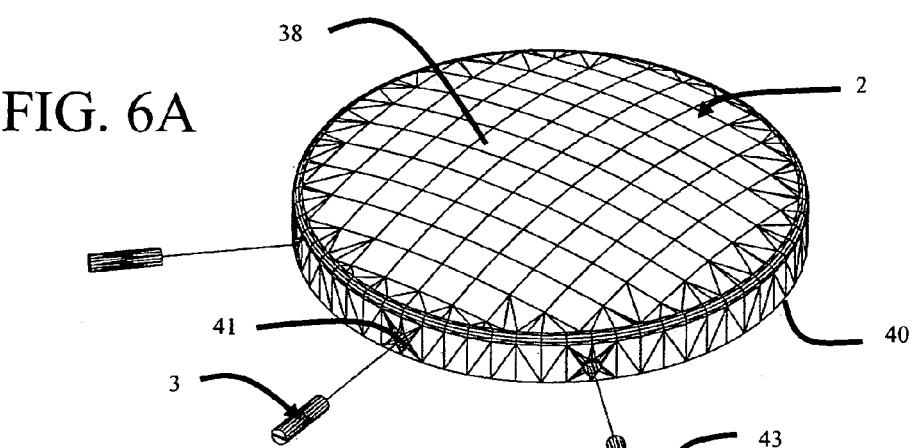
FIGS. 6A and 6B are illustrations of the superior vertebral plates (FIG. 6A) and the inferior vertebral plate (FIG. 6B) of the chambered-ball embodiment of the subject invention. Illustrated is the threading of the elements and the locking screws by which they can be attached to the modular prosthetic disc mechanism.
Figure 6B:
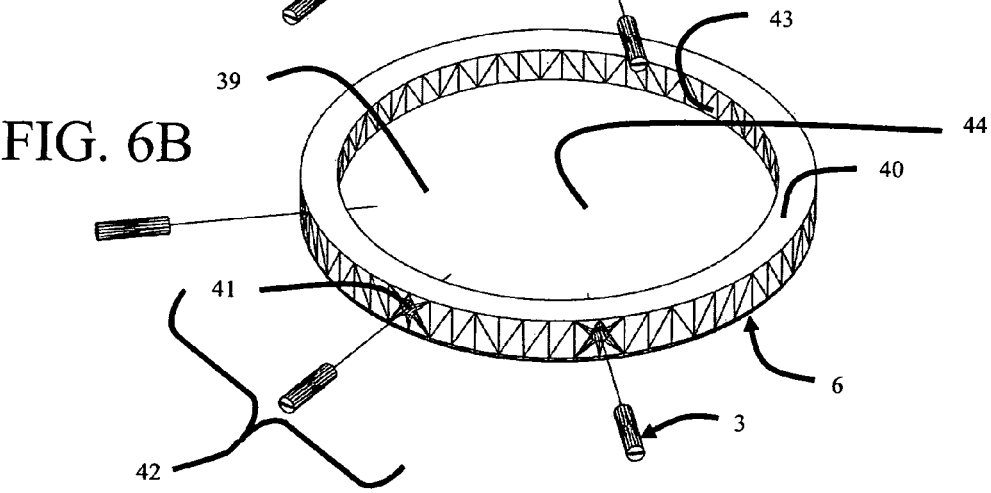

In an alternative embodiment, a girdle ring-bearing 18 and a socket ring-bearing 19, illustrated in FIG. 5, can be utilized with the ball-and-socket joint. FIG. 5 does not illustrate bearing separators and retention matrices that can be utilized in yet a further alternative embodiment, for these particular bearings. In one embodiment, bearing separators and retention matrices are not used, allowing the bearings to move freely within the raceways. In alternative embodiments, interlocking mechanical constraints can prevent the bearings from leaving their raceways.

In one embodiment, the girdle ring-bearing raceway 29 and the socket ring-bearing raceway 36 (FIG. 10) are within the chambered-ball and socket-base respectively. A variety of cross sections can be employed for these raceways. In one embodiment, three bearing contact points 112 (FIG. 10) maintain ball-bearings within the raceways. These ring-bearings, in an alternative embodiment, can comprise separate, complete ring-bearing units that install in seats within the chambered-ball 13 and socket-base 14. These bearings can have a variety of cross-sections, contact points, lubrication tracks and materials, for example, but not limited to, polyurethane, or titanium-hardened-stainless steel alloys. Refer to FIGS. 23A and 23B and FIGS. 24A and 24B for illustrated examples of alternative bearing embodiments.

In an alternative embodiment, the surface bearings in the lower kinematic pair joints of FIG. 28 can comprise for example, high molecular density polyethylene or thermoplastic. In still a further alternative embodiment, the cap-plate 211, piston 212 and the socket-base 214 comprise of, for example, titanium steel.

As illustrated in FIG. 9, the girdle ring-bearing 18 surrounds the chambered-ball 13 in a circle of latitude near, but below the figurative equator 150 (FIG. 9). The socket ring-bearing 19, FIG. 5 (shown as loose bearings suspended in space), and FIG. 8 can be embedded 36 (FIG. 10) into the spherical cavity of the socket-base 14 and in a preferred embodiment, do not move or rotate with the chambered-ball 13 as can the girdle ring-bearing 18. In one embodiment, the ball-bearings 16 in the socket ring-bearing 19 contact the chambered-ball surface at the intersection of that surface and the line between the ball-bearing center and the common center of the chambered-ball 35 and socket cavity 118. In a still further embodiment, each ball-bearing 16 in the girdle ring-bearing 18 (FIG. 9) contacts the socket-base surface at the intersection with that surface of the extended line between the ball-bearing center and the common center of the chambered-ball and socket cavity.

Thus, in one embodiment, the socket ring-bearing 19, 36 provides support (FIG. 10) for the chambered-ball 13, and transmit contact forces to the socket-base 14, and thence to the inferior vertebral plate 6 and inferior vertebra of the FSU into which the inferior vertebral plate 6 fuses. In a further alternative embodiment, the girdle ring-bearing 18, 29 (FIG. 9) supports the chambered-ball, transmits load forces to the socket, and moves with the chambered-ball as it orients the upper elements of the prosthesis during spinal motion.

In summary, the socket 19, 36 and girdle 18, 29 ring-bearings provide separate regions of support for the chambered-ball to prevent jamming and aid in smooth ball-and-socket joint action.

EXAMPLE 2

Polar-Axis Prismatic Joint

The polar-axis prismatic joint can comprise the combination of the spherical chambered-ball 13 (FIG. 9) and the cylindrical piston 12 (FIG. 11) to form a prismatic pair. In one embodiment, the prismatic pair also comprises bearings 24 and 25. In a further embodiment, the cross-section of the chambered-ball cavity 35 is similar or identical to the piston cross-section, but should possess slightly greater radius of curvature to accommodate the piston and allow for bearing clearances. In the lower pair embodiment as illustrated in FIG. 28, the elements 213, and 212 form a cylindrical pair to provide a polar-axis prismatic joint.

Figure 14:
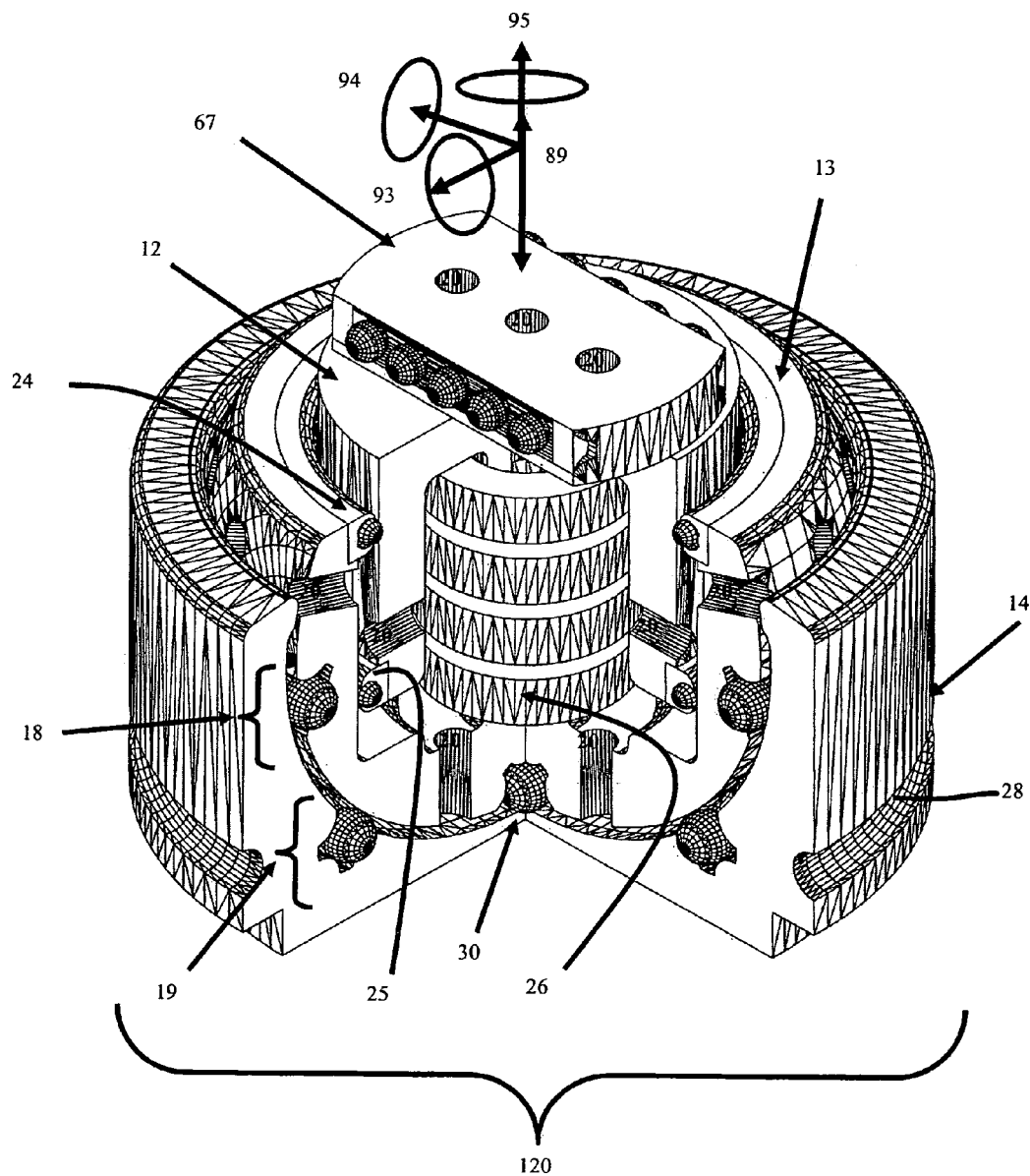
FIG. 14 illustrates the piston, inserted within the chambered-ball, which is positioned within the socket-base. This configuration enables a 4-DOF spherical-polar-axis linkage that orients and projects, or retracts the piston. The installed helical spring opposes compression and extension loads.
Figure 22:
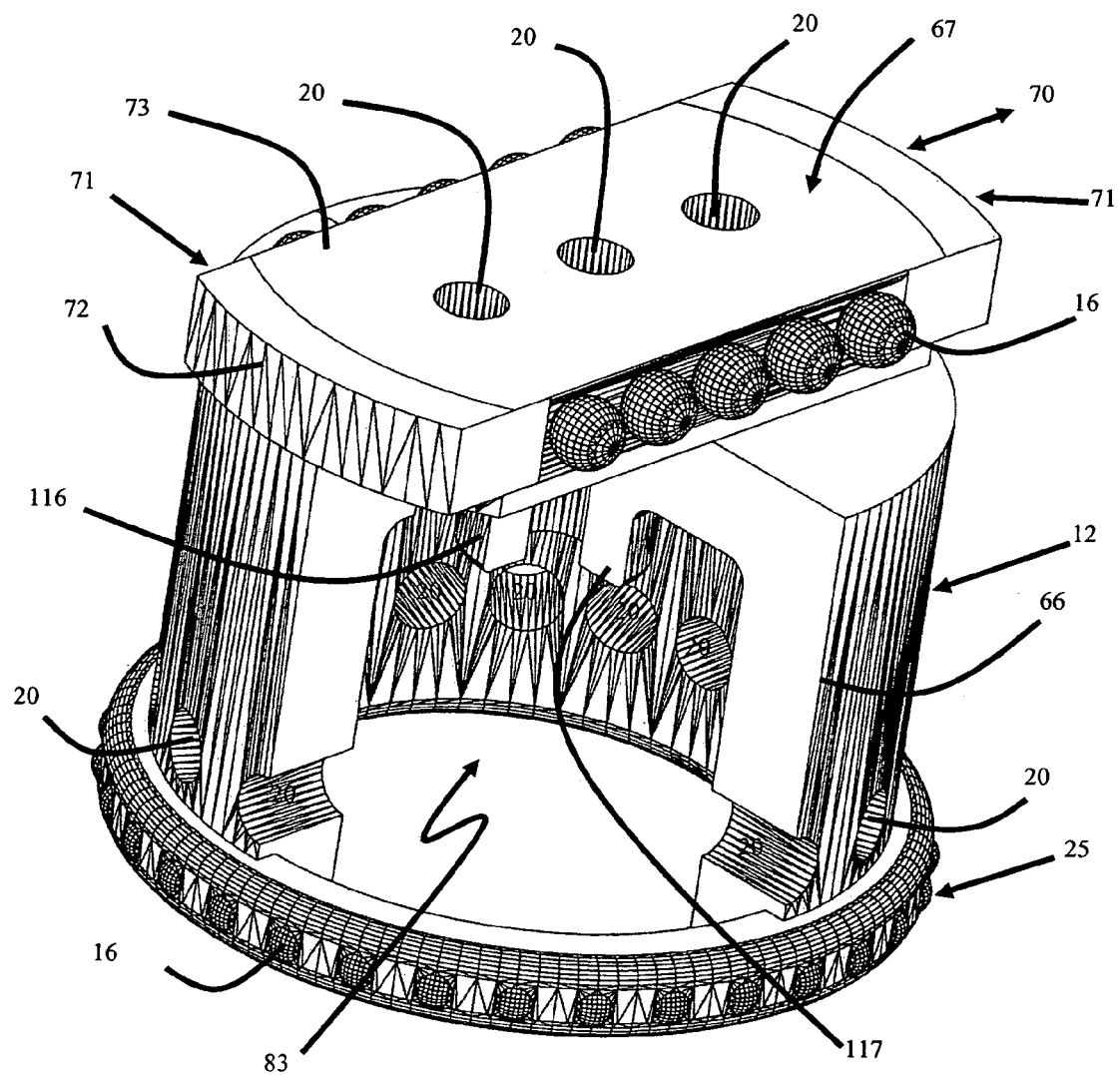
FIG. 22 demonstrates the chambered-ball embodiment utilizing oversized sagittal bearing-stops on the piston, a form of mechanical programming of the sagittal angle limits. The cut-away opens up into the piston cavity and reveals the spring mounting post at the center-top of the cavity.

Hydraulic portals 20 circle the mouth of the chambered-ball 13 to allow lubricating fluid to flow out of the chambered-ball cavity 35 to other moving parts. Four hydraulic portals 20 can pierce the bottom, circling a polar bearing 30 (FIG. 10, FIG. 12) that can be positioned in the base of the chambered ball The piston 12 (FIG. 11, FIG. 22), in one embodiment, comprises a right-circular cylinder 66. In yet a further embodiment, the piston has a cylindrical cavity 83 to contain, for example, a spring, elastomeric device, or other shock absorbing material 26 (FIG. 11). The lower element of the sagittal prismatic joint 67 (FIG. 11) with lateral bearing raceways 21, which can be machined, sits on top of the piston. One or more bearing stops 22 can be placed, for example by welding or pressure fitting into the two raceways 21, preferably one at each end, after bearing insertion. The lower element 67 of the sagittal prismatic joint, in a preferred embodiment, is fixedly attached on the top of the piston (FIG. 11, FIG. 14 and FIG. 22). The lower element of the sagittal prismatic joint 67 can consist of the same material as the piston 12. Alternative embodiments can utilize different materials for these two elements. But, in a preferred embodiment these two elements are rigidly joined.

Figure 16:
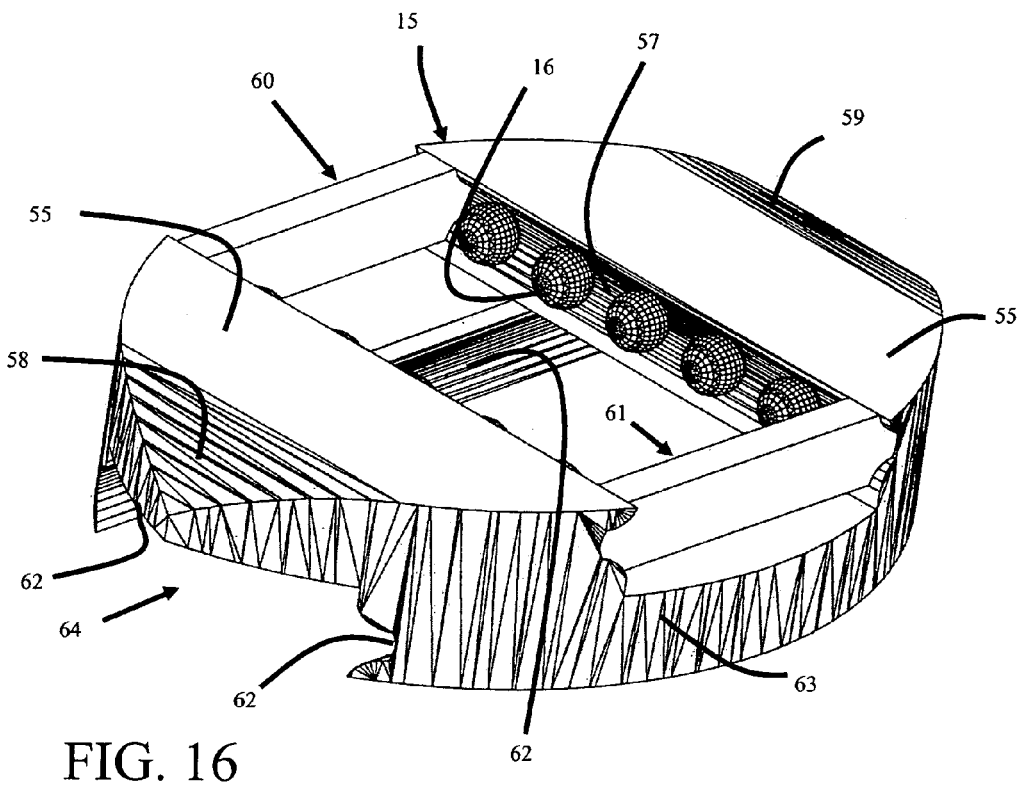
FIG. 16 illustrates the plane-bearing guide of the chambered-ball embodiment and shows the complex surfaces and shapes involved, and reveals bearing and bearing-stop placement. The plane-bearing guide supports two, orthogonal, dual-track raceways that provide the sagittal and lateral prismatic joints of the spatial mechanism.

In an alternative embodiment, one or more bearing stops 22 (FIGS. 11 and 12) are utilized to retain the bearings in the sagittal raceways 21 when the lower half of the sagittal prismatic joint 67 links (as shown in FIG. 17) with the plane-bearing guide 15 (FIG. 16). In one alternative embodiment, bearing stops are utilized at either end of the raceways. In still a further alternative embodiment, the bearing stops are not inhibited by the plane-bearing guide 15 and do not interfere with joint motion. In alternative embodiments, the lateral surface 69 (FIGS. 11 and 12) of sagittal joint element 67 may not extend the full radius of the piston cylinder, but is slightly recessed to provide a seat for oversized bearing stops 71, 72 (FIG. 22). In further alternative embodiments, a recess is not required and the bearing stops, whether oversized or not, can be integrated as part of element 67.

Sagittal bearing stops should contact the cap-plate as a hard joint stop, restricting joint travel in flexion and/or extension. In this manner, flexion and extension limits can be independently controlled.

Figure 19:
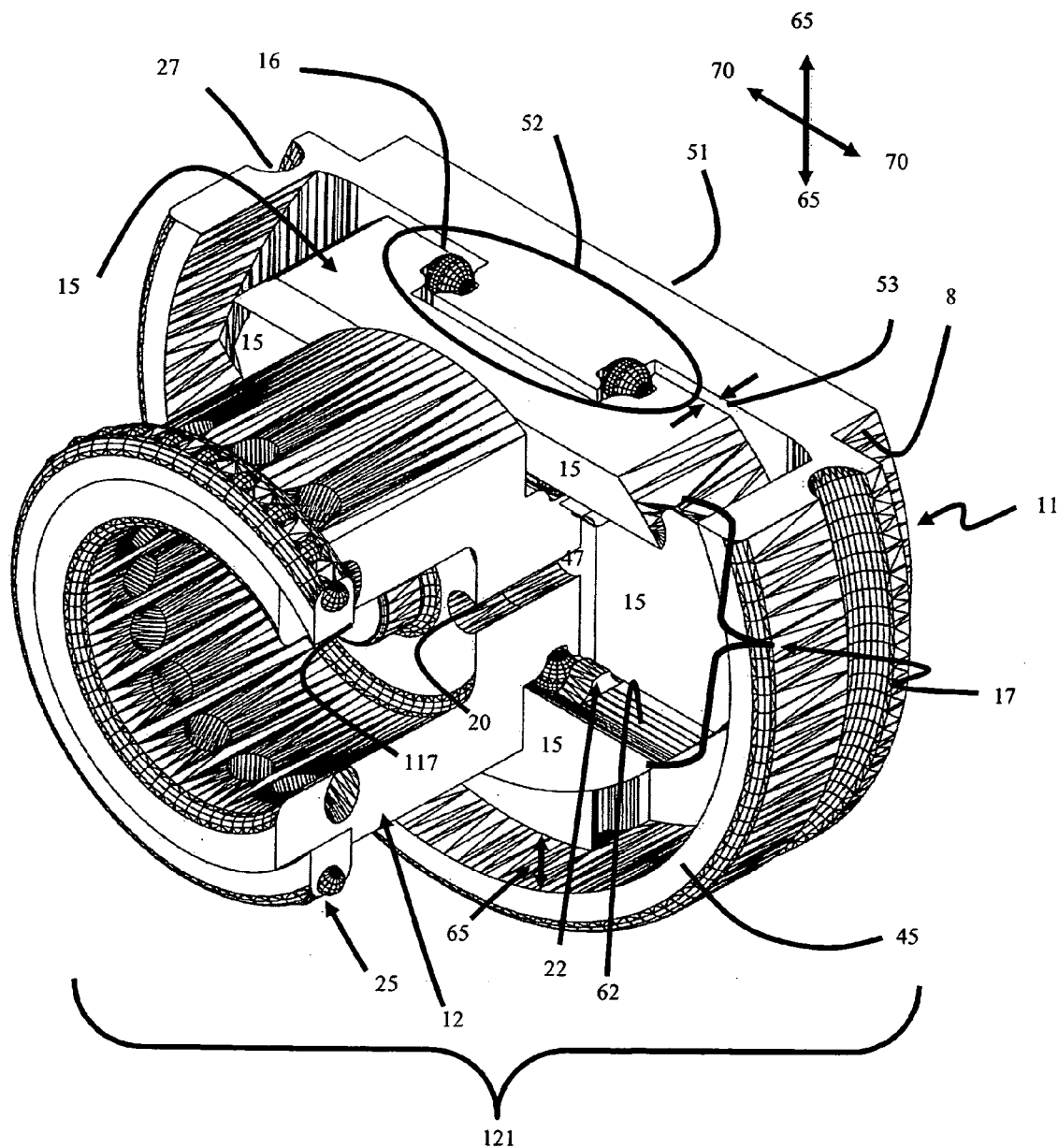
FIG. 19 shows the chambered-ball embodiment with the combined cap-plate, plane-bearing guide and the piston to realize a 2-DOF linkage for motion in the superior vertebral-plane. This cut-away view reveals the lateral and sagittal prismatic joints and their configuration within the plane-bearing guide of this embodiment. The lateral prismatic joint, circled at the top of the figure, allows the piston and plane-bearing guide to move "up and down" ("left to right", i.e., laterally, when installed) with respect to the cap-plate while the sagittal prismatic joint allows the piston to move "left and right" ("fore and aft", i.e., sagittally, when installed) with respect to the plane-bearing guide and the cap-plate. During pure sagittal prismatic joint motion, the plane-bearing guide and cap-plate do not undergo any relative motion with respect to each other.

The piston ring-bearing 25 (FIG. 11) can be press fit or otherwise firmly attached to the seat 68 (FIG. 7A, FIG. 11) at the base of the piston 12 (as shown in FIG. 17). In one embodiment, just above the piston ring bearing seat 68 is a circle of hydraulic portals 20 (FIGS. 7A and 12) within the lateral surface of the piston 12 which lead into the piston cavity 83 (FIGS. 17 and 22). In a further preferred embodiment, three additional hydraulic portals 20 within the top of the piston 12 lead into the piston cavity 83 (FIG. 22). In a preferred embodiment, these hydraulic portals allow lubricants, colloidal suspensions, or other fluids within the boot cavity, to pass to the sagittal prismatic joint 17, 82 (FIG. 5, FIG. 17) and the lateral prismatic joint 52 (FIG. 19).

Figure 7A:
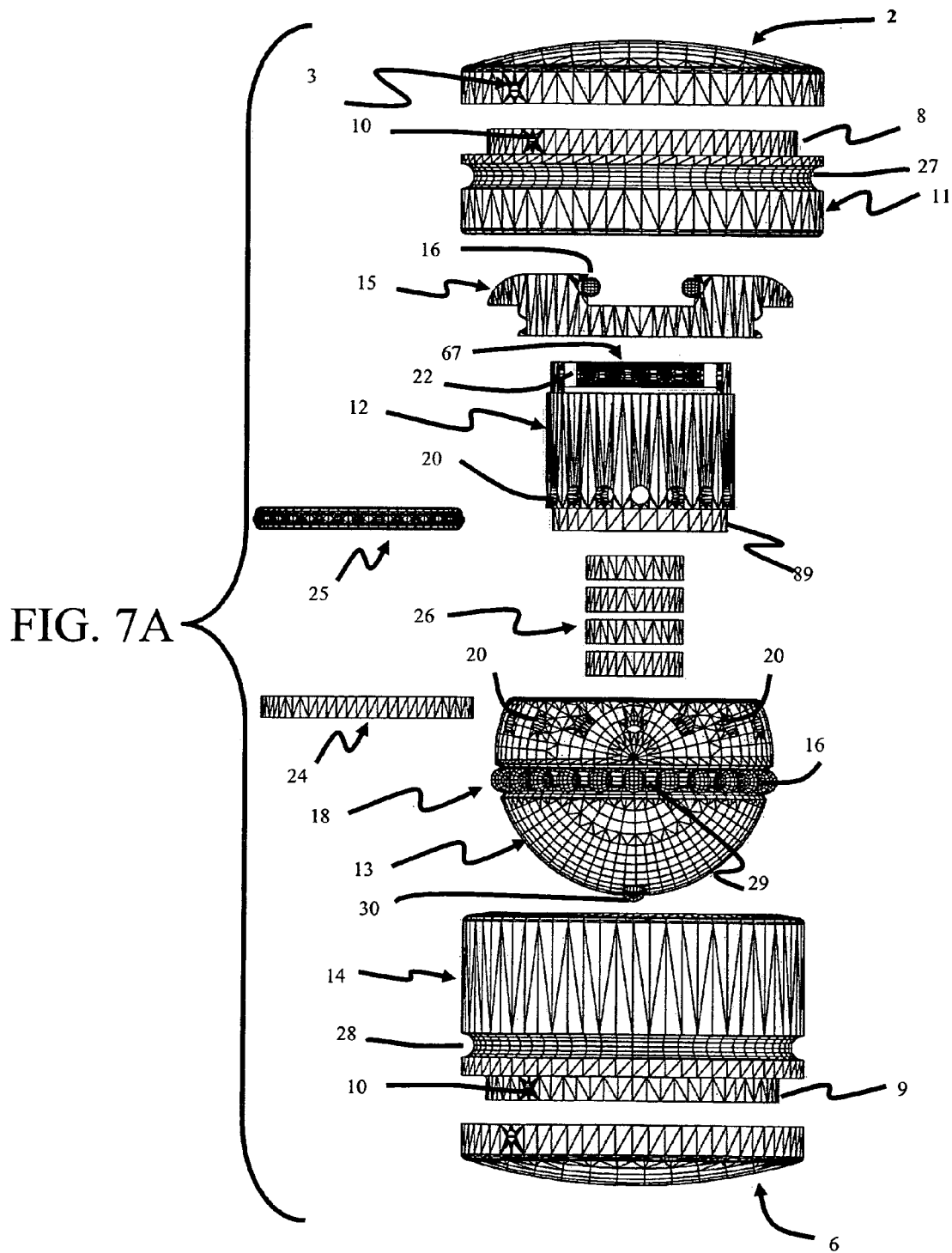

A further embodiment utilizes hydraulic portals 20 on top of the piston 67 and around the base of the piston, just above the piston ring-bearing seat 68, to allow fluid to flow between the inner cavity 83 of the piston and the rest of the prosthetic mechanism encased and sealed by the boot. In a preferred embodiment, as the piston 12 moves in and out of the chambered-ball cavity 35 to match the required intervertebral gap as required by the movement of the FSU, it can also function as a hydraulic pump. The hydraulic portals 20 circling the bottom of the piston 12 above the piston ring-bearing 25 provide an outlet from the piston cavity 83 of hydraulic or other fluids or suspensions sealed inside the prosthetic by the boot, even at maximum flexion and extension of the piston 12. Fluid pumped through hydraulic portals 20 at the base of the piston 12 can pass into a cavity between the piston 12 and the chambered-ball 13 and lubricate the piston and chambered-ball ring-bearings 25, 24. Compression of the piston 12 during FSU movement can also force fluid between the piston and the chambered-ball into the ball-and-socket bearing gap, lubricating the chambered-ball and socket-base ring-bearings 18, 19 and the polar bearing 30 (FIG. 7A, FIG. 10). Fluid flowing out of the bottom of the chambered-ball cavity 35 can also perform this function. Fluid forced out of the hydraulic portals 20 that penetrate the piston top into the piston cavity 83 can automatically lubricate the sagittal and lateral prismatic joints 17, 52 during normal operation of the FSU. In a preferred embodiment, the prosthesis is able to automatically lubricate most or all of the bearing surfaces, points and lines of the spinal disc prosthesis during normal operation.

In other embodiments, the piston 12 can be a variety of, preferably hollow, prismatic shapes, preferable right angled, with arbitrary cross-section shape, preferably, though not limited to, a simple convex curve, with a variety of desired cavities therein. In a preferred embodiment, the piston can slide in and out of the chambered-ball to provide an equivalent of the polar-axis prismatic joint 115 and a piston cavity similar to 83 (FIG. 17) to allow installation of an effective spring, or spring-like, -damping system and to enable hydraulic pumping action.

The piston ring-bearing 25, shown separated from the piston in FIG. 11, can be press fit or welded to the seat 68 and, in one embodiment, forms an integral part of the polar-axis prismatic joint 115 consisting of the piston 12 sliding in and out of the chambered-ball 13 (FIG. 12). The chambered-ball ring-bearing 24 and the piston ring-bearing 25, revealed by the cutaway in FIG. 12, prevent the outside piston surface 66 from engaging the surface of the chambered-ball cavity 35 except through ball-bearings. In a further embodiment, the piston ring-bearing 25 ball-bearings face radially outward and contact the inner surface of the chambered-ball cavity 35 while the chambered-ball ring-bearing 24 ball-bearings 16 face radially inward to contact the outside surface 66 of the piston 12. This provides the bearing mechanism of the polar-axis prismatic joint 115.

The ring-bearing dimensions, can depend upon the application sizing of the mechanism, and place an upper bound on the number and size of the ball bearings. After placement of the piston 12 and spring 26 into the chambered-ball 13 to realize the polar-axis prismatic joint 115 (FIG. 12), the chambered-ball ring-bearing 24 can be press fit or otherwise fixedly attached to the mouth of the ball's cavity. In one embodiment, the ring-bearing 24 is fixedly attached to a seat 84 in the mouth of the ball's cavity 35 (FIG. 9). In a further embodiment, it is the placement of the ring-bearing 24 that secures the piston into the cavity 35 of the chambered-ball. Together, the chambered-ball and piston ring-bearings 24, 25 provide smooth piston motion 89 in and out of the chambered-ball cavity 35 along the polar axis 113 of the ball (FIG. 10, FIG. 12). The central axis 113 of the chambered-ball 13 rotates with the ball as it moves in the socket-base. This rotating axis defines the direction of piston motion 89 of the polar-axis prismatic joint 115 (FIG. 12). In a preferred embodiment, the polar-axis prismatic joint 115, enables telescoping of the piston 12 in and out of the chambered-ball cavity 35 to match the required intervertebral gap currently demanded by the position of the FSU.

EXAMPLE 3

Spherical-Polar-Axis Linkage

In one embodiment, linking the piston 12, with a spring 26, chambered-ball 13, and socket-base 14 provides a 4-DOF spherical-polar-prismatic manipulator with load bearing capacity (FIG. 14). As the more distal elements of the prosthesis, i.e., the plane-bearing guide 15, cap-plate 11, and superior vertebral plate 2, move, the spherical manipulator (ball-and-socket joint) track their orientation 93, 94, 95 and distance traveled 89 along the polar axis 113 (FIG. 10) from the chambered-ball center.

Figures 15A, 15B, 15C:
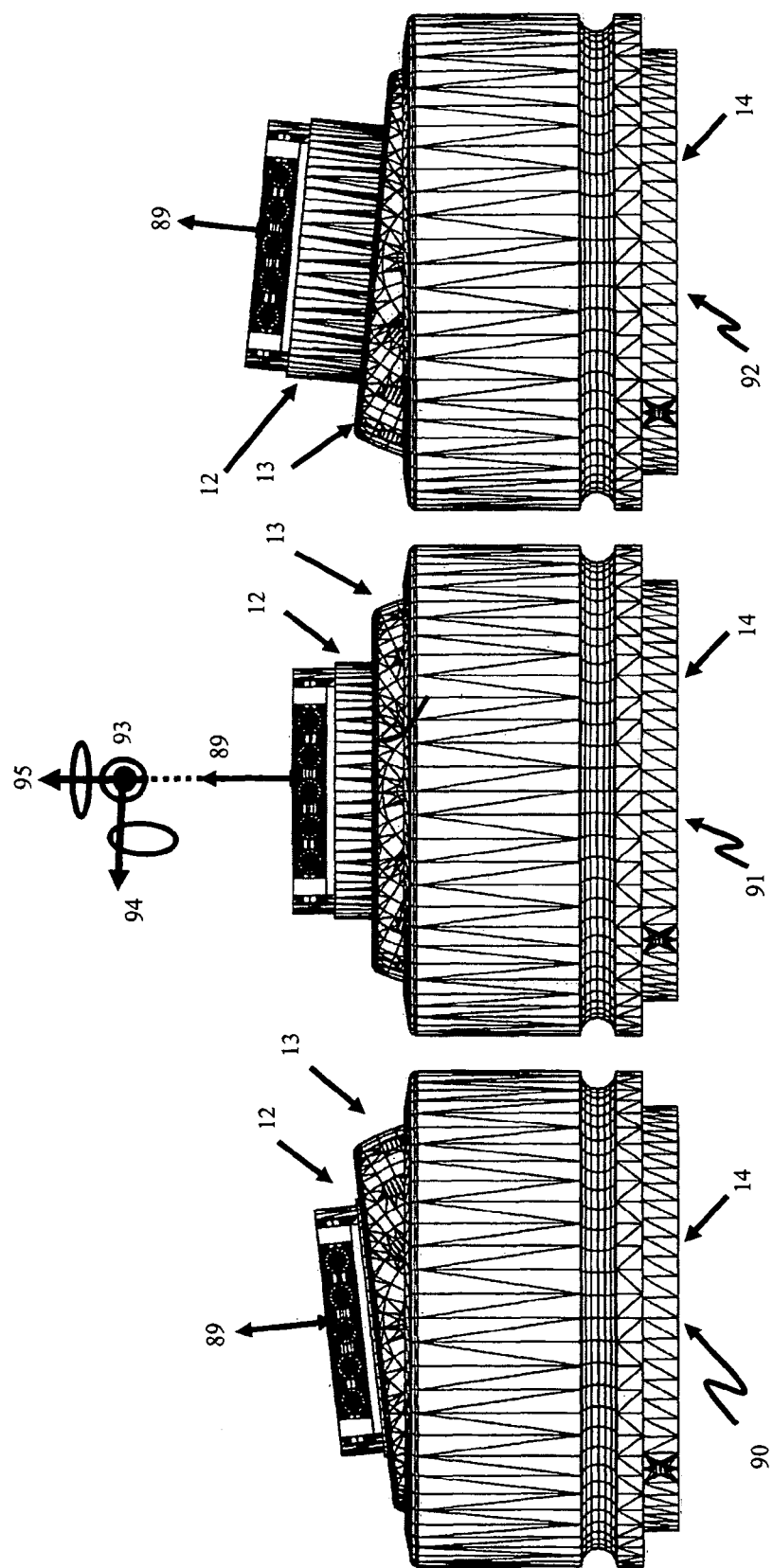
FIGS. 15A, 15B, and 15C illustrate the 4-DOF spherical-polar-axis linkage manipulating the piston to achieve a final position and orientation in flexion (FIG. 15A), neutral (FIG. 15B) and extension (FIG. 15C).

FIGS. 15A, 15B and 15C show the operation of the spherical-polar-axis linkage 115 in flexion 90, neutral 91 and extension 92. As spinal muscles move the superior vertebra of the FSU, loading on the spring or spring-like mechanism or material within the piston changes. In a further embodiment, the principal spring axis coincides and, thus, rotates with, the polar-axis 113, causing the forces acting on the spring to either rotate the spring by means of the ball-and-socket joint or engage the spring along its principal axis. FIGS. 15A, 15B and 15C also indicate the relative, nominal orientations of the chambered-ball for vertebrae C2-C3 in the three configurations.

EXAMPLE 4

Sagittal Prismatic Joint

In one embodiment, the plane-bearing guide 15 (FIG. 16) in conjunction with the piston 12 creates the sagittal prismatic joint 17, 82 (FIG. 5, FIG. 17). FIG. 19 illustrates a cut-away of this joint along with the lateral prismatic joint. In one embodiment, the joint movement 70 tracks along raceways 62 of the plane-bearing guide 15, between the anterior 58 and posterior 59 poles of the plane-bearing guide 15. The plane-bearing guide 15 (FIG. 16) supports two orthogonal, dual-track raceways, one dual-track raceway for lateral bending 57 and one for sagittal flexion-extension 62 of the prosthetic disc linkage. In a further embodiment, the downward, pointed, compound-curved surfaces anterior 58 and posterior 59 to the plane-bearing guide allow more structural material for the guide and the cap-plate. One or more lateral bearing stops 60, 61 can be, for example, pressure fitted or welded into the raceway and prevent the bearings from leaving the raceway of the lateral prismatic joint 52 (FIG. 19).

A frontal view of a preferred embodiment of the sagittal prismatic joint 17 in FIG. 5 illustrates how the bearings 16 interlock the plane-bearing guide 15 to the sagittal bearing support 67 (FIG. 11) that is fixedly attached to, or can be manufactured as an integral part of, the piston 12. In this embodiment, the sagittal prismatic joint facilitates the superior vertebral plate 2, the cap-plate 11 and the plane-bearing guide 15 to slide along the axis of the joint. Since the piston 12 rotates with the chambered-ball 13 as the device accommodates muscle commands, the sagittal prismatic joint line of action rotates in space as dictated by FSU movement.

In one embodiment, the lower tracks of the plane-bearing guide slidably connect with the piston linear bearing guides to form the sagittal prismatic joint 17, 82 (FIG. 5, FIG. 17). In alternative embodiments, ball-bearings of, for example, titanium steel, or, in a further embodiment, rod-bearings of different cross-section and material composition (FIGS. 23A, 23B, and FIGS. 24A and 24B), are positioned in the sagittal bearing raceways and can lock the two pieces together. The rod bearings can also be formed or integrated directly into the contact surfaces of the joint. Thus, in a further alternative embodiment, the surface of the plane-bearing guide 15 does not contact the top surface of element 67 on top of the piston 12. Thus, in this embodiment, the only contact between the two elements should be through the sagittal raceway bearings.

To increase the rigidity of the joint so that it is able to support greater loads, a further embodiment incorporates bearings distributed on the top surface of element 67 of the piston. For example, two bearing raceways can be provided on the top surface of 67, parallel to raceways 62. In a preferred embodiment, the piston 12 and plane-bearing guide 15 typically move 70 with respect to each other only along the sagittal prismatic joint 17, 82 (FIG. 5, FIG. 17). At extremes of the sagittal prismatic joint movement 70, the piston should not, in a preferred embodiment, contact the rim 45 of the cap-plate 11. In one embodiment, as illustrated in FIG. 28, the elements (212, 215) form a prismatic pair for the sagittal prismatic joint and uses only surface bearings. This arrangement provides the greatest load-bearing and greatly simplifies the joint, eliminating all roller and rod bearings.

EXAMPLE 5

Lateral Prismatic Joint

The lateral prismatic joint 52 (FIG. 19) comprises the linking of the bearing raceways 49 of the lateral bearing support 47 of the cap-plate 11 (FIGS. 18A and 18B) with the upper bearing raceways 57 of the plane-bearing guide 15 (FIG. 16). In one embodiment, the guide 15 moves laterally 65 (FIG. 19) along the raceways with respect to the cap-plate. Thus, in a preferred embodiment, it is the lateral prismatic joint 52 that facilitates lateral translations. In the lower pair embodiment, FIG. 28, the elements (215, 211) form a prismatic pair for the lateral prismatic joint, providing greater strength and load carrying capacity, as well as bearing simplification.

Figure 18A:
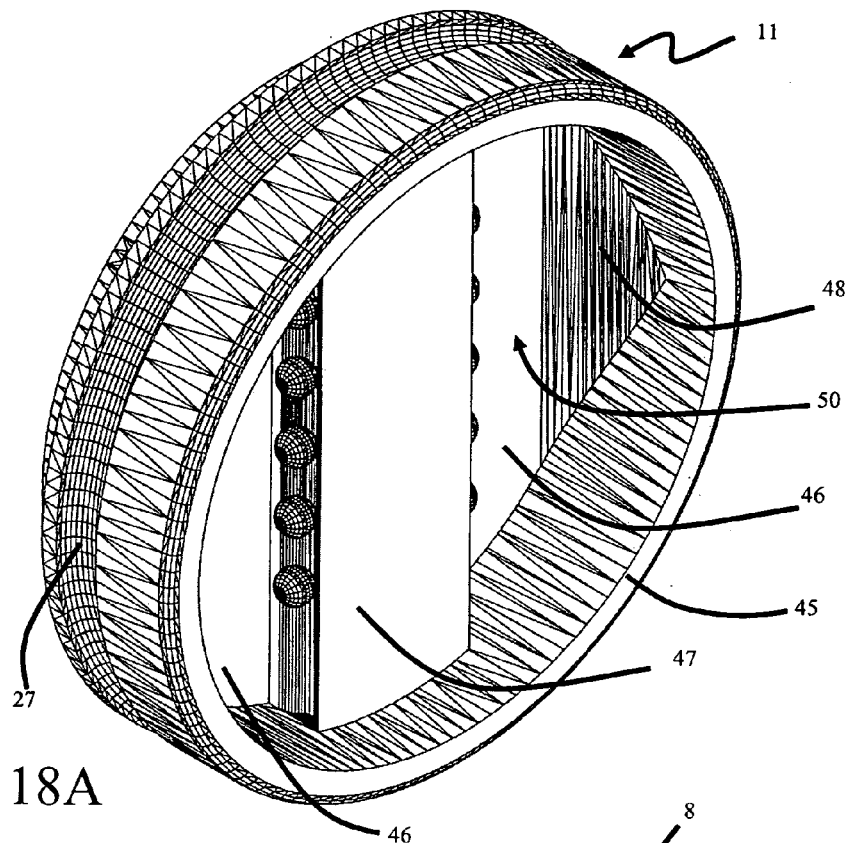
FIGS. 18A and 18B show the underside of the cap-plate (FIG. 18A) of the chambered-ball embodiment of the subject invention, exposing the upper half of the dual-track bearing raceways for the lateral prismatic joint. The cutaway view of the cap-plate (FIG. 18B) shows the cavity structure of the cap-plate and the cap-plate rim as well as the lateral prismatic joint bearings and bearing raceways of this embodiment.
Figure 18B:
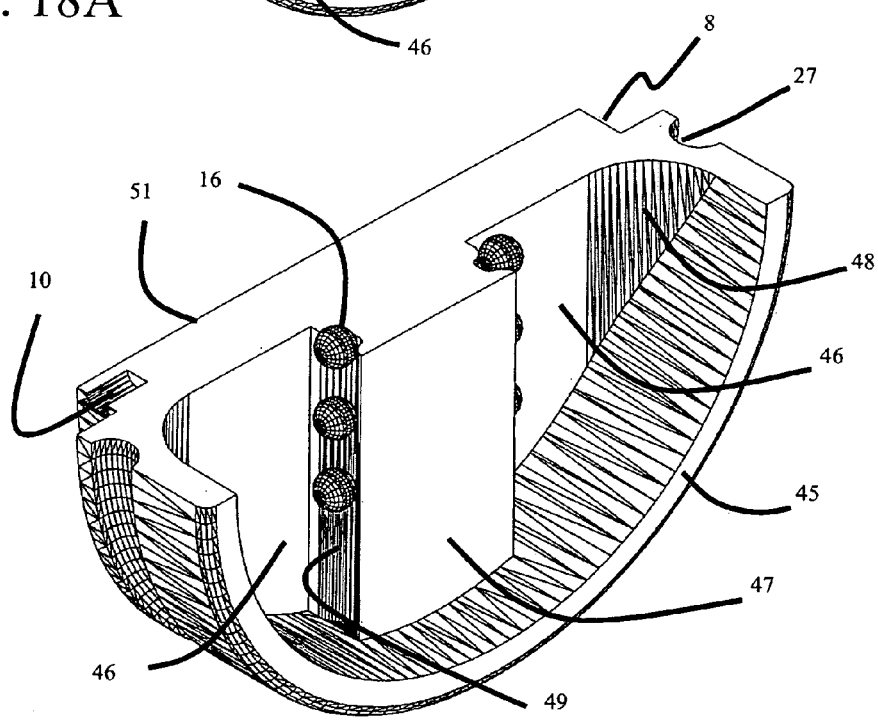

FIG. 18A illustrates the cap-plate 11 and the position of the lateral linear bearing support structure 47 and cap-plate's projecting rim 45. As seen in FIG. 18B, the lateral linear bearing raceways 49 are positioned on each side of the support structure 47. The cap-plate 11 and bearing support structure 47 can be integrated as a single part or manufactured as separate units that are fixedly attached. In one embodiment, additional surface curvature 48 (FIGS. 18A and 18B) at the anterior and posterior sections of the cap-plate can increase strength of the cap-plate. In this embodiment, the convex curvature 58, 59 of the plane-bearing guide 15 (FIG. 16) should be complimentary with the concave curvature 48 of the cap-plate. In a preferred embodiment, the lateral prismatic joint 52 (FIG. 19) maintains a small gap 53 (FIG. 19) between the cap-plate surfaces 46, 47 and plane-bearing guide surfaces 55 (FIG. 16) that reduces interference between those elements during FSU movements with lateral components.

In a further embodiment, this clearance of cap-plate and plane-bearing guide surfaces applies to the entire cap-plate cavity 50 interior surfaces and plane-bearing surfaces 55, 58, and 59. The cap-plate rim 45 and the width of the plane-bearing guide 15, in addition to extensions in width that can be contributed by oversized left or right lateral bearing stops, are able to limit the amount of lateral travel 65 of the plane-bearing guide within the cap-plate 11, and, therefore, in one embodiment the amount of left and right lateral bending. In a preferred embodiment, the center of curvature for the curved lateral surface 63 (FIG. 16) of the plane-bearing guide provides clearance for the guide as it moves laterally underneath the cap-plate. In a further embodiment, the center of curvature for the left and the right lateral surfaces 63 are not the same. In an even further embodiment, the left and right lateral surfaces 63 can be offset rather than centered with the plane-bearing guide to avoid interference with the cap-plate rim 45 during lateral movement. In one embodiment, the plane-bearing guide 15 mated with the cap-plate 11 forms the lateral prismatic joint 52 (FIG. 19). In a further embodiment, titanium steel ball-bearings, or, in an alternative embodiment, for added stiffness, rigid rod-bearings of desired cross sections, lateral surface geometries and material compositions (FIG. 23A, 23B and FIGS. 24A, 24B), are positioned in the lateral bearing raceways 49, 57 to slidably connect the two pieces to form the lateral prismatic joint 52. Thus, in this embodiment, the plane-bearing guide 15 and the cap-plate 11 relate and move relative to each other through the bearing contacts. In a further embodiment, the plane-bearing guide 15 moves laterally 65 along the raceways with respect to the cap-plate 11. In a still further preferred embodiment, at or near the limits of the lateral prismatic 52 joint motion, the plane-bearing guide 15 contacts the rim 45 of the cap-plate 11. Thus, in this embodiment, the cap-plate 11 acts as a hard joint stop, placing a maximum travel limit on the prismatic joint 52 in lateral bending.

To increase the rigidity of the lateral prismatic joint 52 so that it supports greater loads, another alternative embodiment can utilize bearings and bearing raceways distributed on the flat portion 55 of the top surface of the plane-bearing guide 15 (FIG. 16). In a further alternative embodiment, bearing raceways can be utilized on surface 55 (FIG. 16) parallel to raceways 57.

EXAMPLE 6

Spring-Damping System

Preferably the subject invention utilizes a central shock-absorbing material within the core of the piston to reduce the effects of sudden motion on the prosthetic device and to support static loads placed on the prosthetic device. This central shock-absorbing material can comprise a variety of materials, for example, springs, elastomeric materials, or gel inserts.

One embodiment utilizes a central, helical spring 26 (FIG. 13). The spring can comprise a variety of materials, for example, plastics, metals, or a variety of alloys. In a preferred embodiment, the spring comprises machined titanium stainless steel alloy. In an alternative embodiment, the spring further comprises, for example, an elastomer or hydrophilic gel core or other shock-absorbing material structures 103, with sufficient spring constant to sustain the required intervertebral spacing of the FSU in the neutral position under gravitational load and sufficient compression-extension properties to allow the spring to fit into the piston cavity 83 under maximum compression. This spring based system for dealing with static and dynamic loads is referred to as the spring-damping system.

In the neutral position the machined helical spring 26 should be loaded so as to oppose the normal compressive force produced by anatomical structures under gravity.

In one embodiment, the shock absorbing elastomer or hydrophilic gel core does not fill the spring cavity 104, thus allowing for expansion under compression. The spring core materials utilized in the subject invention experience primarily axial forces, and are designed to take advantage of that fact.

In one embodiment, the machined helical spring screws onto the threaded 116 mounting post 117 on the roof of the piston cavity 83 (FIG. 22) and the threaded 32 mounting post 31 on the floor of the chambered-ball cavity 35 (FIG. 10). In a further embodiment, the threading sense of the two spring mounting posts 31 and 117 can be the same and are compatible with the threads 101 of the spring 26 (FIG. 13).

Forces acting on the prosthesis of the subject invention resolve into a force along the polar-axis 113 of the prosthesis and a force orthogonal to the axis. The polar-axis component of the force compresses or stretches the spring and the other force component moves the linkages. However, if the resultant force on the polar-axis 113 is not sufficient to compress or stretch the spring as required, there is no motion and the joint structure bears the force load without linkage motion. In one embodiment, the piston, excluding the sagittal bearing support structure, can act as the machined helical spring itself. In a further embodiment, hydraulic portals would not be utilized other than the separations of the spring rungs, and the top of the sagittal bearing support structure 67 can comprise a large threaded mounting post for the piston-spring to screw onto. In this embodiment, the piston-spring does not slide, but can be anchored into the chambered-ball at the piston seat and under nominal load in the neutral position of the FSU. The increased size of the piston-spring can enhance spring constant design options, but the piston-spring compresses and extends appropriately to match the previous polar-axis prismatic joint motion requirements. In these embodiments, the lateral stiffness of the spring should be greater than the axial stiffness of the spring.

In yet another embodiment, a second, smaller machined helical spring can be mounted on the threaded posts inside the much larger machined piston-spring and chambered-ball cavities. The second machined helical spring parallels the machined piston-spring and may not have to be particularly stiff except as the device nears maximum extension so as to provide additional extension loading capability.

The modular prosthetic disc mechanism is filled with biocompatible lubricating and/or viscous fluids or colloidal suspensions in its minimal volume configuration, typically at maximum flexion. The fluid volume surrounding the piston and the bulging of the boot is sufficient to fill the piston cavity 83 and chambered-ball cavity 35 when the FSU is in the neutral position.

During flexion, the hydraulic system increases fluid pressure in the gap between the chambered-ball and socket base surfaces to reduce friction during motion of the ball-and-socket joint. This effect is similar to the operation of a synovial joint. A similar synovial action takes place at the piston and chambered-ball gap during piston motion along the polar-axis.

To increase the synovial effect between the chambered-ball 13 and socket-base 14, another embodiment eliminates the hydraulic portals 20 around the mouth of the chambered-ball cavity 35 and adds a bearing pressure seal at the mouth of the socket-base cavity 118. This seal prevents, or greatly reduces, the escape of fluid being pumped, during compression, into the bearing gap between the chambered-ball 13 and socket-base 14 through the hydraulic portals 20 at the base of the chambered-ball 13. During extension, the synovial effect is minimal, but then so is the loading on the joint surfaces.

To increase the synovial effect in the polar-axis prismatic joint 115 during compression, another embodiment eliminates the hydraulic portals 20 around the mouth of the chambered-ball cavity 35 and adds pressure seals to the chambered-ball and piston ring-bearings. All cavities in the device fill completely at minimum volume. As the piston extends the fluid in the gap, now under negative pressure, flows into the piston cavity. As the piston compresses, the fluid in the cavity flows into the polar-axis prismatic bearing gap under pressure since bearings seal both ends of the gap. This alternative embodiment preserves the hydraulic damping and shock absorbing characteristics for the polar-axis prismatic joint 115 and its characteristics can be engineered by the number, size and distribution of the hydraulic portals 20 on the top surface of the piston. During compression the hydraulic pressure in the gap between the piston 12 and the chambered-ball 13 also adds stiffness of the joint to lateral forces. This embodiment is compatible with the previous one that increases the synovial effect on the ball-and-socket joint 37. The piston 12 cannot be the helical spring for embodiments that enhance synovial operation.

EXAMPLE 7

Bearings

The subject invention can incorporate one or more bearing types and sizes. In one embodiment, the largest ball-bearings comprise the polar bearing 30 and the bearings utilized in the girdle and socket-base ring-bearing raceways 29, 36; the next largest ball-bearings are utilized in the plane-bearing guide raceways 57, 62; and the smallest ball-bearings comprise the chambered-ball and piston ring-bearings. In a preferred embodiment, the ball-bearings consist of titanium-carbide-covered hardened stainless steel. The size of the ball-bearings depends upon the raceways cross-sections and the number of ball-bearings in each raceway depends upon the scale of the prosthesis.

Other embodiments can vary the number, size, placement and material construction of the bearings and the bearing types. For example, a further embodiment replaces the ball-and-socket ring-bearings 18, 29, 19, 36 with ultra-high-molecular-weight polyethylene or similar thermoplastic bearing material on the exterior surfaces of the chambered-ball 13 and socket's spherical cavity 118. This embodiment can include one of the two polymer surfaces smooth and the other micro-rough, i.e., covered with enough randomly placed micro-bumps that can decrease friction between the surfaces, but not so many as to cause abrasion. The sizes of the micro-bumps can be dictated by desired wear, friction and stiction characteristics.

Another embodiment of the subject invention comprises coating the outer spherical surface of the chambered-ball 13 with, for example, relatively large, fixed, polar spherical sections of polymer material and coating the socket-cavity with a smooth layer of, for example, bearing thermoplastic. The polar spherical sections on the chambered-ball are then able to act as sliding point contact bearings and are arranged to uniformly distribute forces on the socket-base cavity 118. The latter embodiment eliminates the girdle and socket-base ring-bearings 18, 19 and polar bearing 30. Since the spherical sections of thermoplastic can be rigidly attached to the chambered-ball, and/or constitute surface features of a totally thermoplastic chambered-ball, they can avoid blocking the orifice of any distribution of hydraulic portals 20 elsewhere on the chambered-ball's surface.

Another alternative embodiment realizes the lateral and sagittal linear bearings with a tongue-and-groove arrangement comprising, for example, a mix of ultra-high-molecular-weight polyethylene or similar thermoplastic bearing material and biocompatible metal alloys. The tongue cross-sectional shape allows a variety of embodiments, for example, but not limited to: half a right-circular cylinder or half the more exotic cross-sections 76 in FIGS. 23B and 81 in FIG. 24B. In the latter case, the spherical surfaces 79 can offer point contacts between the sliding surfaces of the joint and reduce friction over the line contact of 75 or the surface contact of a tongue with a semicircle cross-section. While creating more friction than roller bearings, the tongue-and-groove arrangement can make the joint stiffer, especially when the tongue embodiment comprises a metal alloy, by eliminating bearing separators and bearing stops. The additional friction and stiction can provide an advantage by increasing FSU stability.

In yet another embodiment of the sagittal and lateral bearings, a bearing-thermoplastic can be utilized to coat portions of the raceway, in addition, titanium-carbide-coated hardened stainless steel cylindrical rod-bearings with various cross-sections 76, 81, can be utilized, with or without lubricant grooves 74, 80, that run the length of the raceway to the bearing stops. FIG. 23A shows a rod bearing 76 with four lubricating grooves 74 and four lines of contact 75, one per quadrant. This arrangement can provide stiffness and support.

Still other embodiments of prismatic joints can employ, for example, rigid rods with different surface geometries and characteristics. In a further embodiment, the rod-bearing geometry in FIG. 24A can contact the raceway surfaces in multiple points 79 on the spherical sections, reducing friction over the length of the cylindrical rod bearing. Rod-bearing 78 can not require lubricant grooves, even though shown, since the gaps between the slightly overlapping spheres can allow lubricant to feed into the raceways.

Further alternative embodiments for the piston and chambered-ball ring-bearings 25, 24 can entertain many of the options mentioned for the other bearings such as for example, comprising a single piece of material, for example, but not limited to, thermoplastic or titanium-covered stainless steel, with a variety of one or more cross-sections for different contact surfaces, lines or points. As mentioned previously, the embodiment illustrated in FIG. 28 utilizes surface bearings that can vary in material composition.

EXAMPLE 8

Corrugated Boot

In this an the alternative embodiments, the corrugated boot 5, 107 (FIGS. 3A and 3B) consists of a strong, flexible-fiber, for example, but not limited to nylon, polyethylene, polyurethane, or spandex-like fiber (with 100% or greater elongation at break) woven screen mesh embedded into a biocompatible elastomer, for example, but not limited to silicones, isotactic polypropylenes with durometer of about 30 to about 40 and a tensile strength of about 5 MPA to about 10 MPA that makes a strong, flexible covering impervious to fluids. The boot thickness, depending upon spinal or other application, can vary from about 0.1 mm to about 1.0 mm or larger. In a preferred embodiment, the boot can be corrugated, much like a billows, with thicker, relatively stiff, fiber-belted annular sections 110 between thinner, non-belted, more flexible annular sections 109. In general, the boot corrugated thickness scales to the application requirements.

The weave and structure of the fiber within the elastomeric matrix can vary in the construction of the boot. In one embodiment, tough fiber belts can be embedded into sections 110 of the corrugated boot that can enable sections 110 to hold their shape better under compression and extension. Flexible fiber with a coarse weave, preferably diagonal to the central-axis of the boot, can be embedded in the entire boot elastomer matrix or encase a gas/liquid impermeable membrane, similar to the construction of tubeless tires known in the art (Thomasberg, U.S. Pat. No. 6,237,662). The diagonal weave can provide more torsion resistance and the flexibility of the fibers can allow the boot to stretch up to about 50% without appreciable degradation in performance. Kevlar, and most commercial polyurethane fibers, can possess an elongation at break percentage that is too low for this application. The fiber size, from about 0.1 mm to about 0.5 mm, cross-section, for example, but not limited to, rectangular, circular, oval, or other polygonal shape, material, for example, but not limited to, nylon, polyurethane, spandex-like fiber, etc., and tightness of the fiber weave, for example, from about 0.05 to about 1 threads per millimeter, constitute boot design parameters, as well as the choice of elastomer substrate, for example, but not limited to, silicon rubbers. To increase boot strength in some applications, such as the larger FSUs, other embodiments can utilize stacked woven layers of boot fabric in conjunction with, or embedded in, a flexible elastomer substrate.

The posterior section of the boot typically stretches very little from a minimum at flexion to a maximum at extension of the FSU. The anterior section of the boot, in some cases, stretches up to about 7 times as much as the posterior portion. Therefore, the fiber density can comprise non-uniform materials throughout the elastomeric matrix.

In yet a further embodiment, the boot can comprise two or more sections, which can be joined to form the boot. In this alternative embodiment, a fluid-impervious, flexible (to about 100% elongation to break) membrane, can be utilized to cover the entire prosthesis. This membrane may not have fiber reinforcement, or very little, and does not utilize the corrugated structure discussed above.

In a further embodiment, two or more sections of thicker, tougher corrugated boot material can be used over the anterior surface of the membrane and one or more over the posterior surface of the membrane, for example extending from the cap-plate 11 to the socket-base 14. The corrugated strips can function somewhat like separate anterior and posterior ligaments, providing stability and strength to the joint. Both the strips and the membrane can be clamped together into the cap-plate grooves 27 and socket-base 28 by means of clamping rings.

In a preferred embodiment, the boot wraps around the modular prosthetic disc mechanism 7, 108 (FIGS. 3A and 3B) and clamps securely to the cap-plate and socket-base to prevent fluid seepage into or out of the modular prosthetic disc mechanism that it encases. In a further preferred embodiment, the boot is open at each end with an internal diameter that can be slightly less than the outer diameter of the cap-plate and socket-base at the openings. The boot stretches some and slips snuggly over the cap-plate and socket base.

EXAMPLE 9

Vertebral-Plane Linkage and Operation

Figure 20:
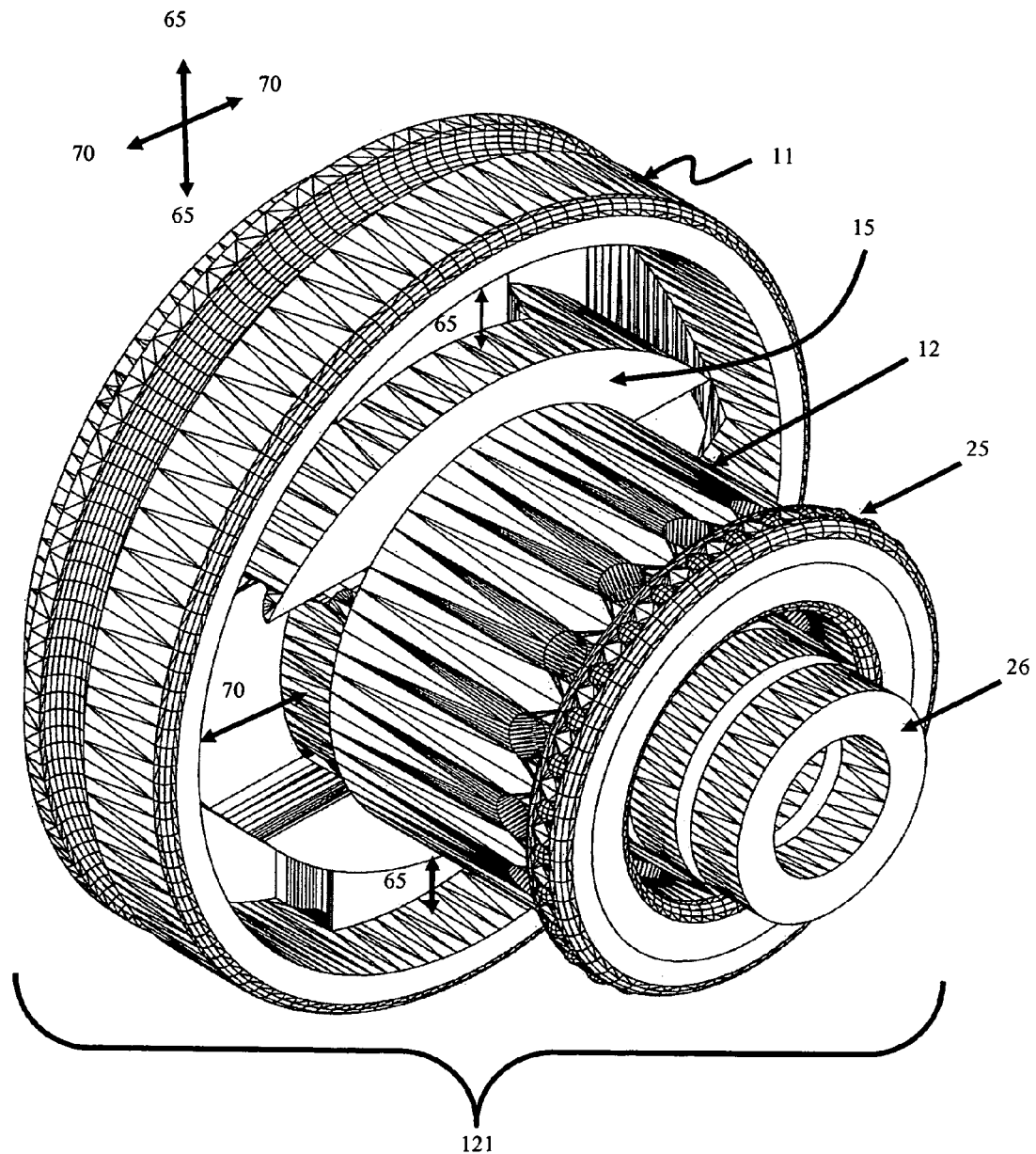
FIG. 20 presents a full, underneath view of the 2-DOF linkage, which can be referred to as the superior vertebral-plane linkage, realized by the cap-plate, plane-bearing guide, and the piston. A stylized spring is shown mounted onto the piston. The open end of the spring connects to the mounting post at the floor of the chambered-ball cavity of this embodiment.

In one embodiment, the cap-plate 11, plane-bearing guide 15, and the piston 12 are joined to provide a 2-DOF linkage called the vertebral-plane linkage 121 (FIG. 19, FIG. 20). In an alternative embodiment, interlocking bearings are utilized as the points of connection between these elements of the spinal disc prosthesis. In one embodiment, two orthogonal lines of movement 65 and 70 (FIG. 19) are able to adjust the position of the vertebral plane. Further, in one embodiment, the vertebral plane is oriented to be perpendicular to the polar axis 113. The vertebral-plane linkage 121 can position any vertebral-plane frame that is fixed to the superior vertebra of the FSU in which the prosthesis is installed to any position in the vertebral-plane contained in the FSU workspace. The 2-DOF vertebral-plane linkage 121 coupled with the 4-DOF spherical-polar-axis linkage 120 can provide a general purpose, 6-DOF linkage 96 (FIG. 21) between the superior and inferior vertebral plates, hence, superior and inferior vertebrae into which the plates are fused.

The vectors, 65, 70, and 89, in FIG. 21 indicate the three orthogonal translational degrees of freedom that can be obtained with the 6-DOF linkage 96 of the subject invention. The three translational motions 65, 70, and 89 correspond to the movements that can be generated by the lateral, sagittal, and polar-axis prismatic joints 52, 17, and 115, respectively. The ball-and socket joint 37, of the subject invention, can generate the three independent angular orientations 93, 94, and 95.

Figure 25A:
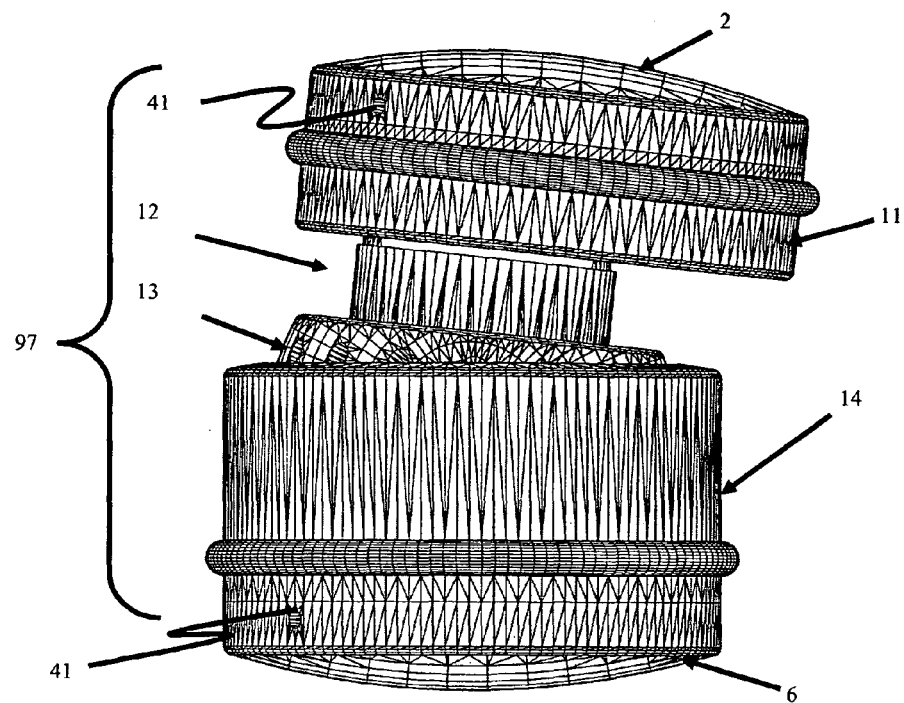
FIGS. 25A and 25B show the spatial mechanism in extension as seen from the left-lateral side of the chambered-ball embodiment of the prosthetic device.
Figure 25B:
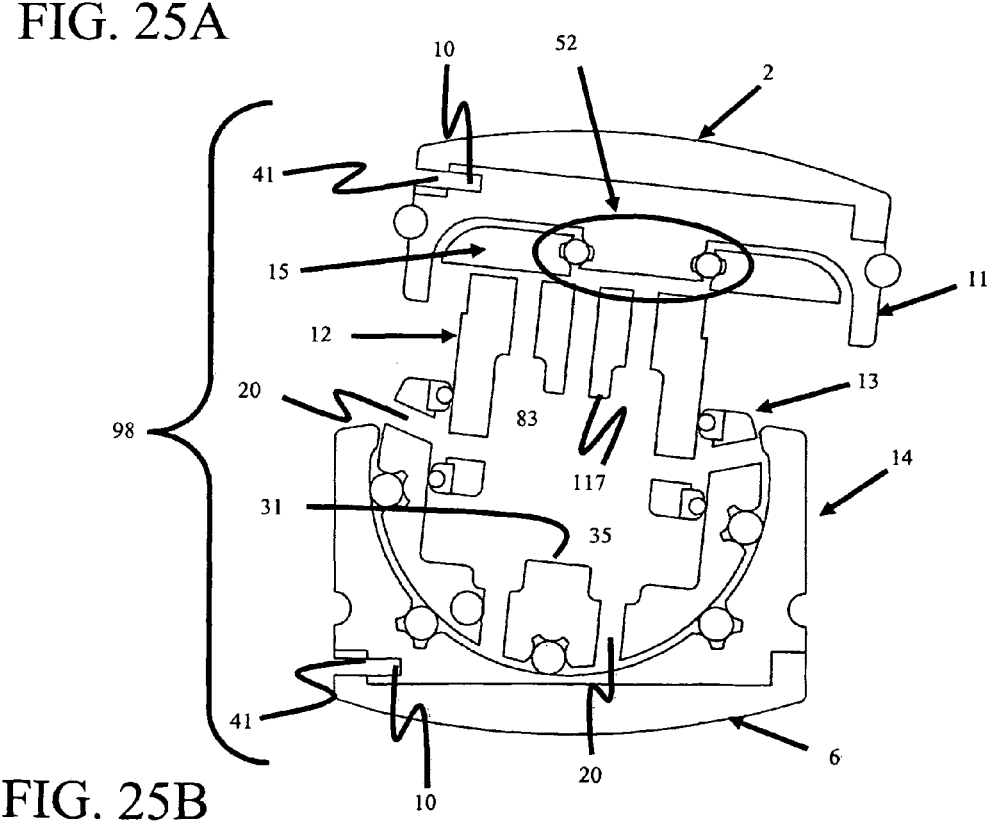

In a preferred embodiment, when the FSU moves to extension, the prosthesis moves into the configuration illustrated in FIG. 25A. FIG. 25A illustrates the prosthesis as seen from a left-lateral 3-D viewpoint while FIG. 25B is a mid-line sagittal plane cross-section of the device in the same configuration. In this preferred embodiment, there should be an equal tilt of the superior vertebral plate 2, the cap-plate 11, the plane-bearing-guide 15, piston 12 and chambered-ball 13 towards the posterior, but the cap-plate 11 and plane-bearing guide 15 can be more posterior than the piston 12. This indicates that the former translates posteriorly with respect to the piston 12 along the sagittal prismatic joint 17. The extension of the piston 12 along the polar axis 113 and out of the chambered-ball 13 is near maximum in this configuration. Although, as seen in the projection, there is yet more room for the piston 12 to extend since the piston ring-bearing 25 has not yet come up against the chambered-ball ring-bearing 24. As the piston 12 moves into extension, fluid in the upper cavities of the prosthesis drains into the chambered-ball and piston cavities 35, 83.

Figure 26A:
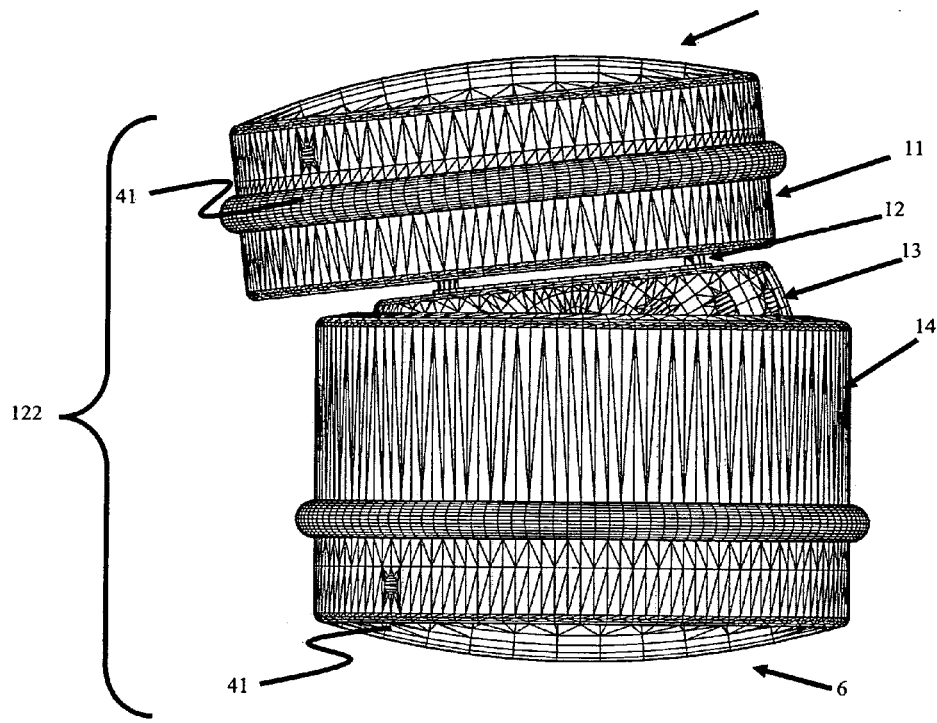
FIGS. 26 and 26B illustrate the spatial mechanism in flexion as seen from the left-lateral side of the chambered-ball device.
Figure 26B:
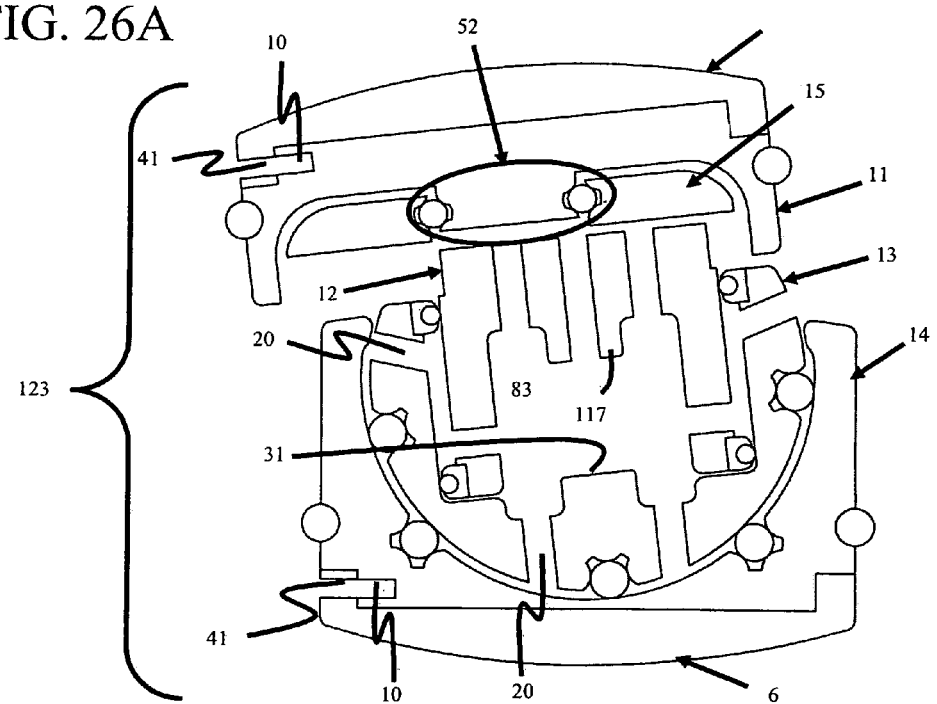

In a further embodiment, during flexion of the FSU, the prosthesis is able to move into the configuration drawn in FIG. 26A. FIG. 26A illustrates the prosthesis as seen from a left-lateral 3-D viewpoint while FIG. 26B is a mid-line sagittal plane cross-section of the device in the same configuration. In this embodiment, there is an equal tilt of the superior vertebral plate 2, the cap-plate 11, the plane-bearing-guide 15, piston 12 and chambered-ball 13 towards the anterior, but the cap-plate 11 and plane-bearing guide 15 are more anterior than the piston 12. This indicates that the former translates anteriorly with respect to the piston 12 along the sagittal prismatic joint 17. The piston 12 maximally slides into the chambered-ball 13 along the polar axis 113 in this configuration. In this embodiment, the piston-ring bearing 25 sits on the piston seat 33 within the chambered-ball cavity 35. The prosthetic should not be able to flex further when the piston sits on the piston seat 33 (FIG. 10) of the chambered-ball cavity 35. In this preferred embodiment, the shock absorbing material, for example a spring 26, elastomer, or various hydrophilic gel materials, inserted into the spring core reach maximal compression.

The extension and flexion configurations in FIGS. 25A and 25B and FIGS. 26A and 26B make apparent the relative angle of chambered-ball rotation from flexion to extension, with neutral as the zero reference. In a preferred embodiment, the swing angle of the polar axis 113 of the chambered-ball between maximum flexion and maximum extension is from about 5° to about 10°. In an even more preferred embodiment, the swing angle of the polar axis 113 of the chambered-ball between maximum flexion and maximum extension is from about 10° to about 20°. Additionally, in a preferred embodiment, the lateral bending swing angle of the polar-axis 113 between maximum left-lateral bending and maximum right-lateral bending is from about 3° to about 8°. In an even more preferred embodiment, the lateral bending swing angle of the polar-axis 113 between maximum left-lateral bending and maximum right-lateral bending is from about 8° to about 14°. In an alternative embodiment, the lateral bending angle limits can be increased by about 1° by narrowing the width of the plane-bearing guide. Axial rotation of the piston and chambered-ball can also be partially constrained by the boot and by the natural limits of the FSU muscles and ligaments.

Figure 27A:
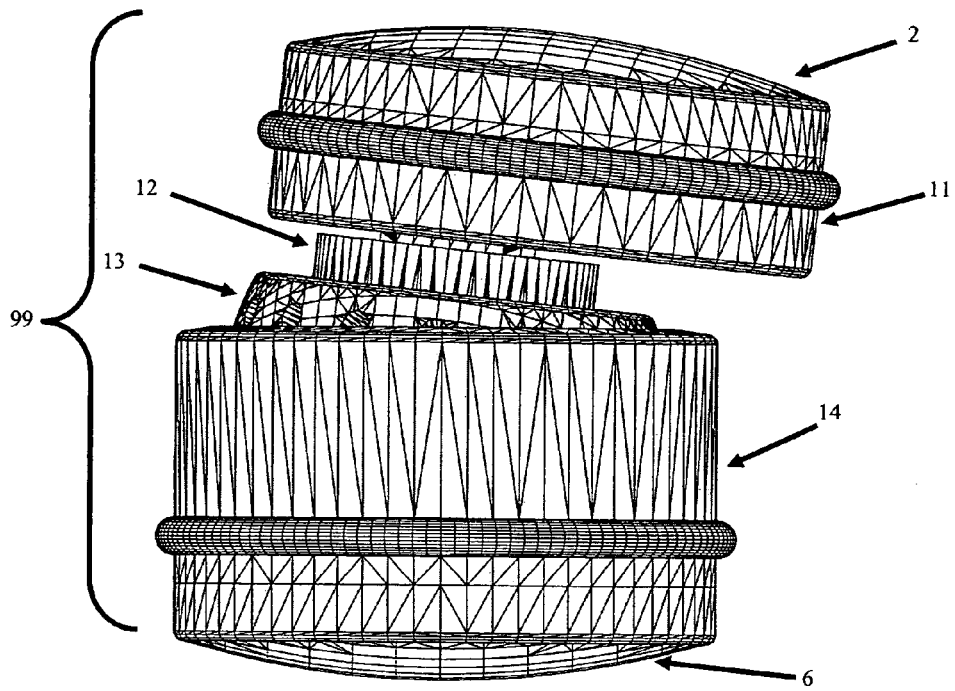
FIGS. 27A and 27B are views of the chambered-ball spatial mechanism from the posterior side executing pure right-lateral bending.
Figure 27B:
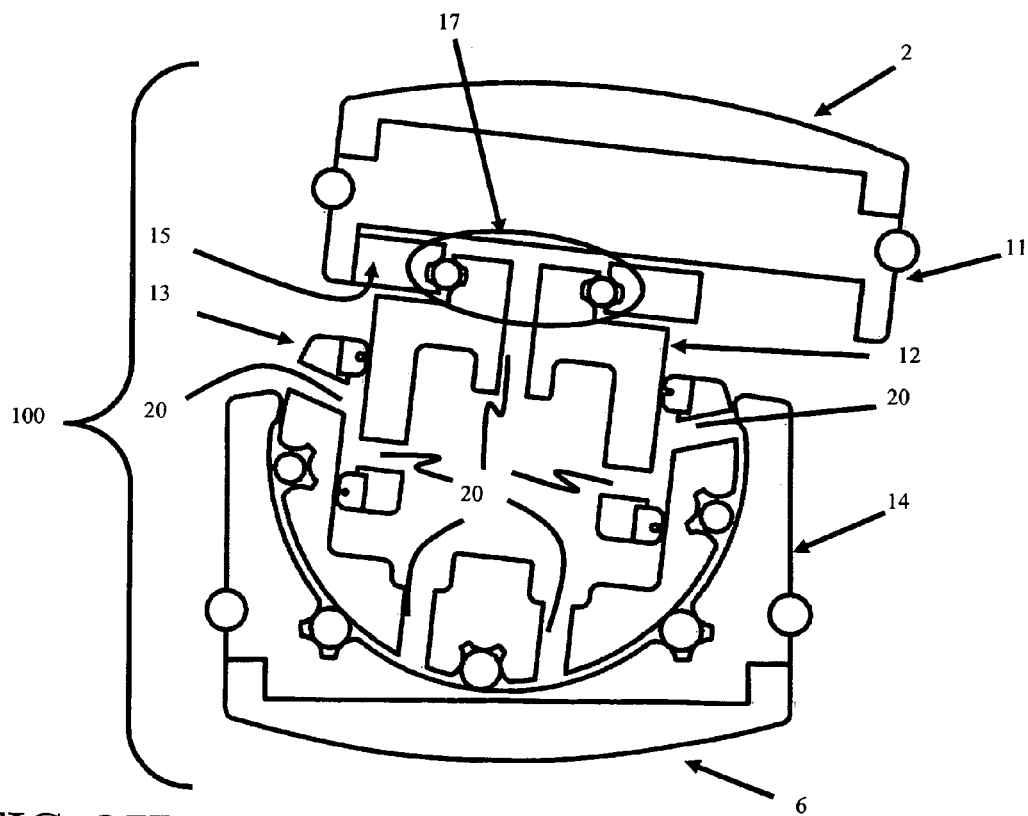

Pure right-lateral bending of the prosthesis, shown from a 3-D posterior viewpoint in FIG. 27A, differs in several respects from extension in FIG. 25A. The ball-and-socket joint 37 rotates more distal elements of the device about the frontal axis instead of the sagittal axis, but in all other respects the function performed by the orienting joint is essentially the same. From the midline frontal plane projection of the prosthesis in pure right-lateral bending, however, the plane-bearing guide 15 moves with respect to the cap-plate 11 and contacts the cap-plate rim 45, which can function as an effective, mechanical stop for the lateral prismatic joint. Finally, the piston may not extend as far at maximum lateral motion as it does at maximum extension due to the motion allowed by the facet joints of a typical spine.

In a preferred embodiment, the ball-and-socket joint 37 orients the more distal elements, the piston 12 extends or retracts, and the plane-bearing guide 15 can slide into place with respect to the cap-plate and the piston simultaneously. In a further preferred embodiment, within the workspace of the linkage, forces can cause either movement along prismatic joint axes, rotate the chambered-ball 13 in its socket-base 14, or compress or stretch the spring 26. The modular 6-DOF prosthetic device structure itself bears torsion loads about the frontal and sagittal axis, but the corrugated boot in the subject invention can offer the only resistance to axial torsion loads.

In a further embodiment the assembled, kinematically-linked, 6-DOF linkage of the device is approximately 50 millimeters or less from end to end. In an even more preferred embodiment, the assembled, kinematically-linked, 6-DOF linkage of the device is approximately 20 millimeters or less from end to end.

The 6-DOF linkage 96 (FIG. 21) can achieve most combinations of sagittal, lateral, and axial rotations within the above angle limits while performing the necessary translations along the polar-axis, sagittal, and lateral prismatic joints 115, 17, 52 induced by the displacement of the superior vertebra with respect to the inferior vertebra of an FSU. This range of motion is suitable for any disc replacement along the spine.

EXAMPLE 10

Alternative Chambered-Ball Embodiments for Use with Non-General FSU

Mechanical programming of the prosthesis can utilize oversized joint stops on the lateral and sagittal prismatic joints to create a prosthetic workspace that 1) can more nearly match a patient's nominal FSU workspace and flexibility or 2) can accommodate clinical conditions that indicate movement restrictions or workspace reductions of the modular 6-DOF spinal disc prosthesis.

Essentially the spatial mechanism can be tailored to meet individual client specifications through mechanical programming with oversized joint stops. Lateral bearing stops 60, 61, if oversized, limit the travel of the lateral prismatic joint 52 to less than the maximum by extending beyond the edge of the plane-bearing guide's lateral surface 63 with the same surface curvature as the guide. As the unit performs lateral bending, the oversized stops can contact the cap-plate rim 45 for smaller lateral angular displacements. These stops need not be identical in size. Equal extension of the oversized bearing stops yield the same movement reduction in the left-lateral or right-lateral direction of the lateral prismatic joint 52, which translates into reduced lateral angles. Unequal sized bearing stops yield different limits in opposing traversals along the lateral prismatic joint 52, which translates into different limits for left and right lateral bending. Similarly, oversized sagittal bearing stops 71, 72 make the effective diameter of the piston 12 just that much larger, causing the piston 12 to jam against the cap-plate rim 45 as a hard stop for smaller angles of flexion and extension. These stops need not be identical in size. Equal extension of the oversized bearing stops yield the same movement reduction anteriorly or posteriorly of the sagittal prismatic joint, which translates into reduced angles of flexion or extension of the unit. Unequal sized bearing stops yield different limits in opposing traversals along the sagittal prismatic joint 17, which translates into different limits for flexion and extension Some workspace and movement restrictions, while mechanically programmable with oversized joint stops, lead to modifications of the invention that reduce the degrees-of-freedom, hence, complexity and number of kinematic pairs. For example, if clinical conditions indicate that axial rotations must be eliminated, an alternative embodiment replaces the ball-and-socket joint 37 (FIG. 10) by a universal joint (Hooke joint) to eliminate axial rotation in the modular prosthetic disc mechanism 7, 108 (FIGS. 3A and 3B) and make it stiff to torsion. For even more severe restrictions that require the elimination of lateral bending, another embodiment replaces the ball-and-socket joint 37 by a simple rotating joint about the sagittal axis. A non-circular piston 12 cross-section eliminates axial rotation in this latter embodiment.

EXAMPLE 11

Spinal Disc Prosthesis Utilizing Lower Pair Elements

All joint elements of the modular prosthetic disc mechanism 7, 108 can be replaced by lower pairs, a choice that eliminates all ball-bearings and rod-bearings and, technically, makes the modular prosthetic disc mechanism into a prosthetic disc linkage (FIG. 28). The ball-and-socket joint 37 becomes a spherical pair (213, 214) and the polar-axis, sagittal, and lateral prismatic joints 115, 17, 52 (FIG. 12, FIG. 19) become true prismatic pairs (212, 213), (215, 217) and (215, 252) respectively, with only surface contact for all joints, no multi-point or line bearings.

In this alternative linkage embodiment, the bearings become the surface contact of the various pairs as follows. The spherical surface of the socket-base 214 and the chambered-ball 213 contact each other directly, with a small clearance to form the ball-and-socket joint. The cylindrical pair (212, 213) forms the polar-axis prismatic joint. The plane-bearing guide 215 raceways are grooves for sliding tongues 252 mounted on the cap-plate 211 and tongues 217 mounted on the piston 212. The sliding surfaces for both lateral and sagittal prismatic pairs on the cap-plate 211 and the upper flat surface 55 on the plane-bearing guide 215 become part of the load bearing surfaces of the lateral prismatic joint, yielding greater strength and load capacity. The surface 73 (FIG. 22) on top of the piston 212 FIG. 28) and the lower flat surface on the plane-bearing guide 215 next to the piston become part of the load bearing surfaces of the sagittal prismatic joint, yielding greater strength and load capacity. Finally, this alternative embodiment eliminates the piston and chambered-ball ring-bearings and increases the thickness of the chambered-ball so that the piston's lateral surface 66 slides against the cylindrical surface of the chambered-ball cavity 35. To reduce friction in the sagittal and lateral prismatic joints, the plane-bearing guide can be, for example, machined or cast out of high molecular density polyethylene or other rugged thermoplastic to reduce friction between it and titanium-carbide-coated stainless steel embodiments of the cap-plate 211 and piston 212. The chambered-ball too is made from tough, durable thermoplastic to reduce friction in the ball-and-socket joint while the socket-base 214 is titanium-carbide-coated stainless steel.

Even though this embodiment increases friction in the joints, it is simpler to build, has fewer parts, and is more robust and able to handle greater loads. These considerations might favor the lower-pair embodiment over the ball-bearing version. In another embodiment of FIG. 28, the superior and inferior plates are a titanium alloy and the remaining elements are high molecular density polyethylene or similar thermoplastic.

EXAMPLE 12

Assembly of the Chambered-Ball Prosthetic Disc Linkage Embodiment

An exploded view of the modular 6-DOF spatial mechanism spinal disc prosthesis (FIG. 7A) identifies the principle elements of the prosthesis in a preferred embodiment. In this view of a preferred embodiment of the disc prosthesis (FIG. 7A), the socket ring-bearing 19 is hidden in the socket-base 14 and the upper part of the lateral prismatic joint is hidden within the cap-plate 11.

An example of the modular prosthetic disc mechanism 7, 108 (FIG. 3) assembly sequence of a preferred embodiment helps to visualize the linkage and interaction between the various components of the module.

The opening of the socket-base spherical cavity 118 (FIG. 8) is less than the circumference of the spherical chambered-ball 13 (FIG. 9), which itself exceeds a hemisphere in size. Additionally, a protruding lip 119 (FIG. 8) along the socket cavity opening narrows the opening further (FIG. 8) and blocks the girdle ring-bearing 18 (FIG. 5) from exiting the socket cavity 118. In a preferred embodiment, this lip has a smaller radius of curvature than the socket cavity, but larger than the chambered-ball 13 and shares the same center with the ball and socket cavity. To join the ball and socket and form a spherical joint 37 (FIG. 10) the socket-base can comprises two or more sections. In one embodiment, the socket-base comprises two halves. In a further embodiment, the chambered-ball and the ball-bearings for the girdle 18 and socket 19 ring bearings are placed into the raceways 29 (FIG. 9) and 36 (FIG. 10) respectively, the socket-base sections, preferably halves, are placed over the ball, and fixedly attached by, for example, welding, or otherwise fastened, joining the socket sections or halves, to enclose the chambered-ball and lock it and the ball-bearings into the socket cavity 118. Under normal operation, it is preferable that the chambered-ball 13 not pull out of the socket-base 14. In an alternative embodiment, the socket-base 14 and chambered-ball 13 form an essentially spherical pair (213, 214). In a further preferred embodiment, the socket-base and chambered ball utilize spherical surface bearings (FIG. 28).

To continue assembly of a preferred embodiment of the subject invention, the spring 26 (FIG. 13) is screwed onto the threaded 32 mounting post 31 (FIG. 10) at the floor of the chambered-ball cylindrical cavity 35 (FIG. 9). Further, the piston is inserted with piston ring-bearing 25 (FIG. 11) mounted onto the bearings seat 89 (FIG. 11), into the cylindrical chambered-ball cavity. The piston and ball are locked together by mounting the chambered-ball ring-bearing 24 into the seat 84 on the chambered-ball 13 (FIG. 9). Continuing with a preferred embodiment the piston's threaded 116 mounting post 117 (FIG. 12) is connected to the spring 26. The piston 12 and chambered-ball 13 form the polar-axis prismatic joint 115 that slides along the central axis of the piston (FIG. 12), which also defines the polar-axis 113 (FIG. 10) of the chambered-ball 13. The spring 26, provides a spring-damping system for the prosthesis and enables the prosthesis to accommodate compression and extension loads. In one embodiment, the spring also comprises an undersized elastomer 104 or hydrophilic gel core 103 (FIG. 13). As the piston moves in and out 89 of the chambered-ball cavity, the spring 26 compresses or extends. Increased compression on the spring causes the top of the piston to come into contact with the elastomer or gel core material 103 and provide additional load bearing and shock absorbing capacity.

Thus, in one embodiment, this subassembly 120 (FIG. 14) constitutes a 4-DOF Spherical-polar-prismatic linkage that is able to orient, or point, the piston 12 in any direction and extend or retract it radially along the chambered-ball's polar-axis 113. Actuation of the spherical-polar-axis linkage 120 facilitates the movement of, for example, lubricating fluid through hydraulic portals 20 located on the piston 12 and chambered-ball 13 to bearing surfaces, points and lines. In a further preferred embodiment, the number, size and distribution of the hydraulic portals 20 on these elements determine the amount of hydraulic damping, shock absorption, and lubrication distribution and flow.

In one embodiment, the anterior to posterior raceways 62, the sagittal raceway, (FIG. 19) of the plane-bearing guide 15 (FIG. 16) are slidably connected within with the sagittal prismatic joint raceways 21 located at the distal end of the piston 12 (FIG. 11). In an alternative embodiment, ball-bearings 16 are utilized with joint stops 22 to slidably connect the plane-bearing guide 15 (FIG. 19) and the piston to form the sagittal prismatic joint 17 (FIG. 5, FIG. 19), 82 (FIG. 17).

In a further embodiment, an additional prismatic joint in the kinematic chain is created by a cap-plate 11 that is slidably connected to the plane-bearing guide 15 (FIG. 20) while aligning the two lateral raceways 57 (FIG. 17) of the plane-bearing guide 15 with the two raceways 49 on the lateral prismatic joint support 47 (FIG. 18A). In an alternative embodiment, ball-bearings 16 can be utilized with joint stops 60 and 61 (FIG. 17) to slidably connect the plane-bearing guide 15 and the cap-plate 11 to form the lateral prismatic joint 52 (FIG. 19). The plane-bearing guide 15, which slides laterally within the cap-plate cavity 50, in an alternative embodiment, provides ample clearance for utilizing various point, line and surface bearings. To complete the assembly of the modular prosthetic disc mechanism of a preferred embodiment 7, 108, a boot 5, 107 is utilized over the subassembly, and aligned with a cap-plate groove 27 and a socket-base groove 28 (FIG. 7A) having corresponding depressions 109 (FIG. 2A, FIG. 2B) in the boot. In a further preferred embodiment, the boot position is maintained with the use of clamping rings 4 (FIG. 2A, FIG. 2B) which are positioned over the boot and securely clamp the boot into the grooves, sealing the mechanism from external fluids. In yet a further preferred embodiment, a corrugated boot is utilized comprising sections of alternating thickness around the circumference of the boot as illustrated in FIGS. 2A and 2B. Thus, as the corrugated boot compresses, the more elastic, thin sections 109 collapse and the thicker less-elastic sections 110 resist the hydraulic pressure inside the prosthesis. At maximal extension, a negative pressure develops as the amount of fluid will not fill the prosthesis cavities.

In one embodiment, a fluid, such as, for example, lubricating fluid, a viscous fluid, and/or a colloidal suspension is inserted into the boot cavity filling up to about 95% of the cavity when in a neutral position. In yet a further preferred embodiment, the cavity space not filled with lubricating fluid is filled with air, or other gases, to equalize internal pressure with ambient pressure. The fluid and air inserted into the modular prosthetic disc mechanism can cause bulging of the corrugated boot 5, 107 when the piston 12 assumes maximum compression. Thus, at maximal flexion, the fluid pressure inside the prosthesis is positive. During compression, the air or other gases within the boot can provide additional shock absorption. In yet a further embodiment, a syringe can be used to insert the various fluids or suspensions, for example lubricating fluids, into the device. In a still further embodiment, an opening within the central, threaded screw hole 10 in the cap-plate rim 45 can be used to introduce various fluids within the boot of the subject invention. In yet a further preferred embodiment, a screw 3, in conjunction with, for example, a liquid gasket, can be used to seal this opening from the environment and prevent leakage.

In one embodiment, assembly of the prosthetic disc linkage 7, 108 requires aligning the module properly with respect to the vertebral plates 2, 6 as the module requires a definite orientation with respect to the vertebral plates. When inserting a new prosthetic disc of the subject invention, the vertebral plates can be properly aligned on the modular disc prior to installation. In one embodiment lock-and-align screws 3 (FIG. 5, FIG. 6A and FIG. 6B) can be used to join the superior vertebral plate 2 to the cap-plate 11 and to join the inferior vertebral plate 6 to the socket-base 14. In a further embodiment, lock-and-align screws 3 are inserted through holes 41 in the anterior lip 40 of the vertebral plates (FIG. 6) and screw into threaded holes 10 (FIGS. 3A and 3B) of the cap-plate 11 and socket-base 14 (FIG. 4) of the mechanism. In a still further embodiment, three lock-and-align screws are utilized with the cap-plate 11 and three lock-and-align screws are utilized with the socket-base 14. When utilized, the screws can prevent the modular prosthetic disc mechanism 7, 108 from disengaging or misaligning with the vertebral plates.

In yet a further embodiment, a center-anterior positioned screw-hole can provide the surgeon a fiducial mark for prosthesis insertion. The other matching lock-and-align holes can vary in number and location on the vertebral plates, cap-plate and socket-base, depending on spinal location and surgical convenience for easy insertion and removal.

II. Cylindrical-Joint Spinal Disc Prosthesis:

This alternative embodiment of the subject invention utilizes three mutually orthogonal, spring actuated, interlocking cylindrical joints forming a kinematic chain between two or more vertebral caps. The cylindrical-joint embodiment, like the chambered-ball embodiment, provides for six-degrees-of-freedom throughout the FSU workspace while preserving a linked kinematic chain between the vertebrae of the FSU, but differs with the addition of six-degrees of dynamic response along and about the cylindrical joint axis. This dynamic response is provided by combined torsion and linear springs along each cylindrical axis. More explicitly, the cylindrical-joint embodiment allows for more straightforward design techniques to approximate the mechanical load-bearing features of the human disc by using three machined helical springs arranged to form a configuration of three orthogonal cylindrical joints. Each spring can be designed with a mix of torsion, compression/extension, and lateral bending specifications to best suit a particular patient's requirements. Additionally, as discussed above for the Chambered-ball embodiment, one or more machined helical springs can comprise a variety of suitable biocompatible materials, including, but not limited to, titanium steel titanium-carbide-coated stainless steel, polyurethane, polyurethane thermoplastic or other suitable bio-inert materials, or combinations thereof, with appropriate mechanical properties of compression and extension along its axis, and torsion about its axis along the length of its supporting platform. In a preferred embodiment, the motion elements of the prosthetic devices of the subject invention are fabricated from titanium steel and, in certain embodiments, use hardened ball-bearings on moving interfaces.

Figure 30:
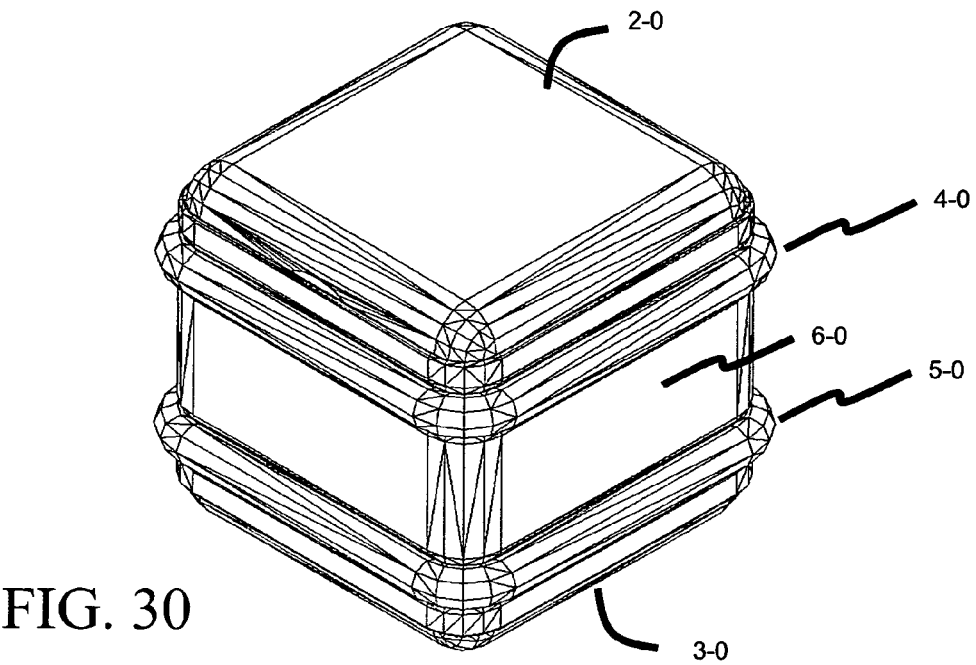
FIG. 30 illustrates a cylindrical-joint embodiment of a cervical spine prosthesis protected by a flexible, protective boot to isolate the internal mechanism from the surrounding environment. Alternative embodiments may not use a boot. The lateral and sagittal cylindrical joint platforms can have upper and lower surfaces that encourage vertebral bone attachment. Alternatively, vertebral caps can be used to make the device modular. Modular versions require modification of the lateral and sagittal joint platforms to allow attachment and detachment of the prosthesis from fixed, bone embedded vertebral caps without disturbing bone structures (Refer to FIGS. 51 and 54). While the embodiments here and in FIGS. 40 and 41 illustrate rectangular structures for simplicity, ovoid structures can also be used, for example as shown in FIGS. 52-56.
Figure 37:
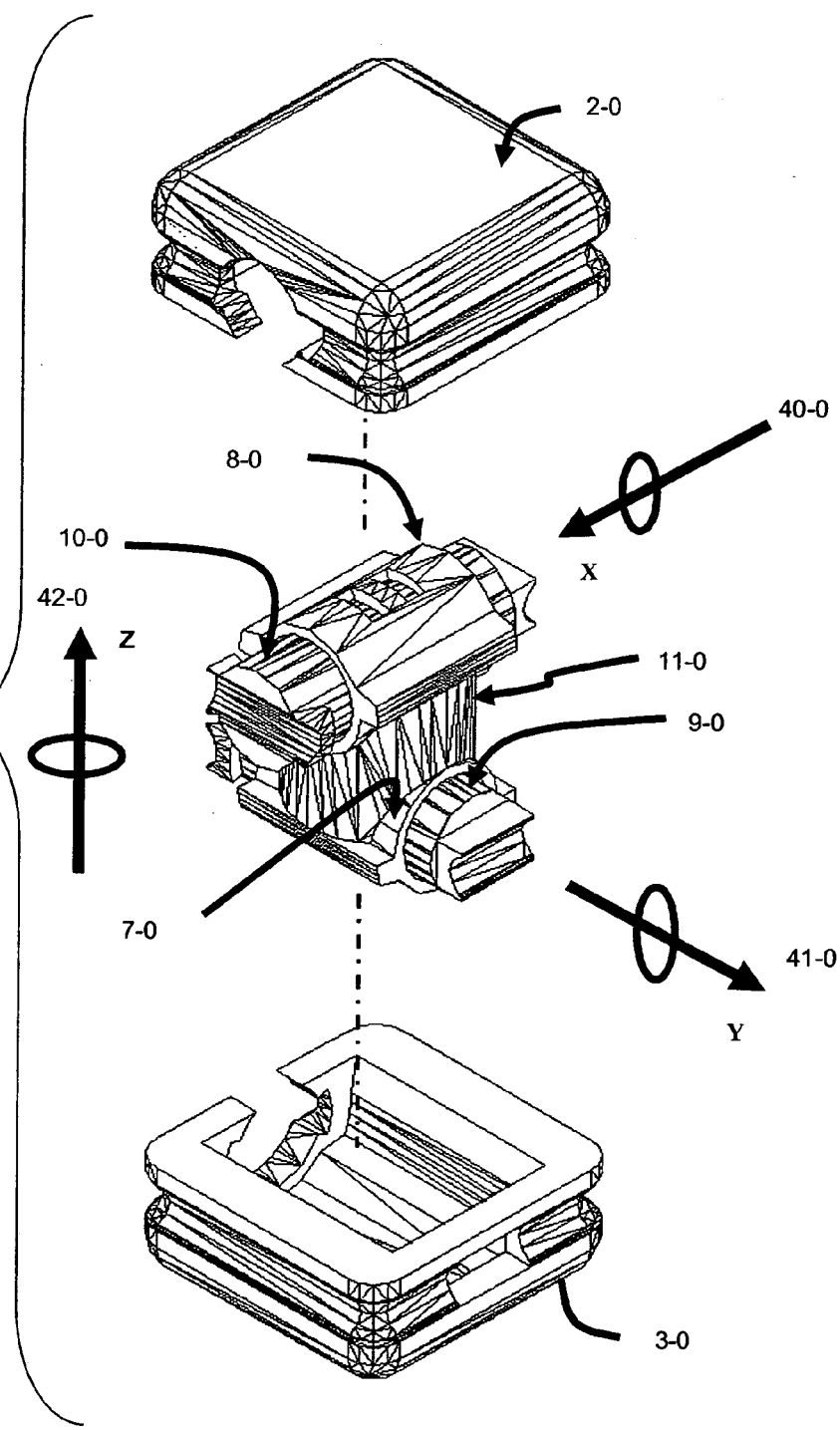
FIG. 37 shows an exploded view of the cylindrical-joint embodiment of the prosthesis, illustrating the top and bottom lateral-cylindrical-joint and sagittal cylindrical-joint platforms and the central, three, orthogonal, and cylindrically jointed mechanism. In this embodiment, the top sleeve houses the lateral spring and constitutes a rocker-slider element of the lateral cylindrical joint that translates along, and rotates about, the lateral spring fixed into its platform. The bottom sleeve houses the sagittal spring and constitutes the rocker-slider element of the sagittal cylindrical joint that translates along, and rotates about, the sagittal spring fixed into its platform. The large, rotating, central-axis spring, or more simply, axial spring, of this embodiment kinematically links the lateral cylindrical joint to the sagittal cylindrical joint. Thus, a complete kinematic chain, with up to 6-DOF, links the lateral cylindrical-joint platform to the sagittal cylindrical-joint platform. The axial spring is able to compress/extend and twist about its central axis, but is maximally rigid to lateral bending, and constitutes the axial cylindrical joint. This spring approximates the compression and extension dynamical response of the human disc along the axis of the spine. A key feature of this embodiment is that, for flexion and extension and axial twisting of the neck, the spring rotates so as to always self-align its axis with the spinal axis. For such motion, the axial spring provides the same dynamic response along the spinal axis regardless of posture.

In preferred cylindrical-joint embodiments, shown for example in FIGS. 30 and 37, the additional features lend greater simplicity, fewer parts, less constraining dimensions, ease of manufacture, and the ability to more closely approximate human disc mechanical response to loading. With regards to loading, the previously described chambered-ball embodiment employs a rotating axial spring inserted into a ball-and-socket joint for load bearing, whereas the current invention supplies two other springs to support lateral and sagittal spinal loads, namely, forces and moments-of-force about the sagittal and lateral axes, while at the same time providing a much larger load-capable (torsional and force) rotating axial spring. The larger size of the axial spring of the additional embodiments makes load-bearing implementation easier.

Figure 41:
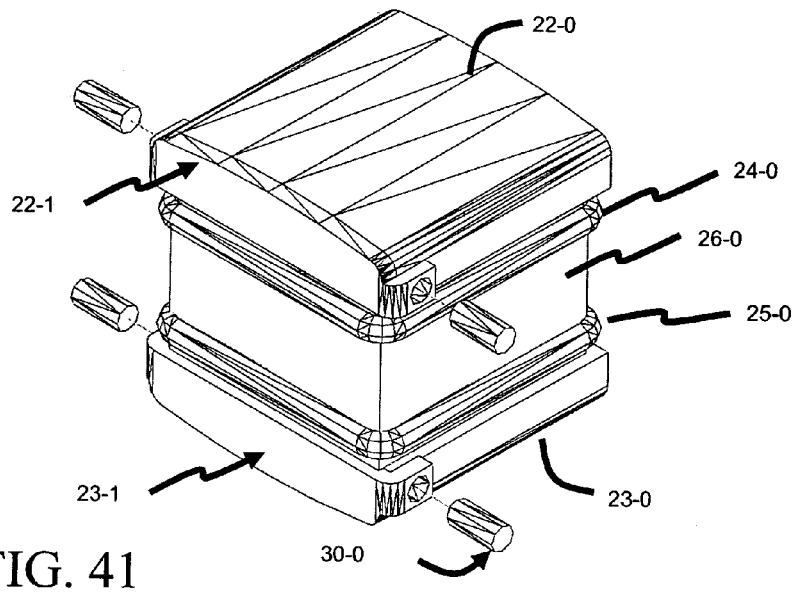
FIG. 41 represents a further embodiment that utilizes a rocker-slider mechanism, wherein only a rotating axial spring provides dynamical properties, as in the embodiment of FIG. 40. In this embodiment the rotating axial and lateral sleeves are combined with the axial and lateral solid shafts, respectively. This embodiment provides a complete 6-DOF kinematic chain between the lateral cylindrical-joint platform and the sagittal cylindrical-joint platform and further provides 6-DOF of motion between the lateral and sagittal joint platforms fixed to their mounting vertebral caps, as all the preferred embodiments do, but only provides dynamical response along the rotating axial spring as in the original preferred embodiment. This dynamical response moves with the axis of the spine during posture changes involving flexion, extension, and axial twisting. Also shown are vertebral plates that allow the embodiments of FIG. 30 and FIG. 40 to be modified to achieve a more modular functionality.
Figure 52:
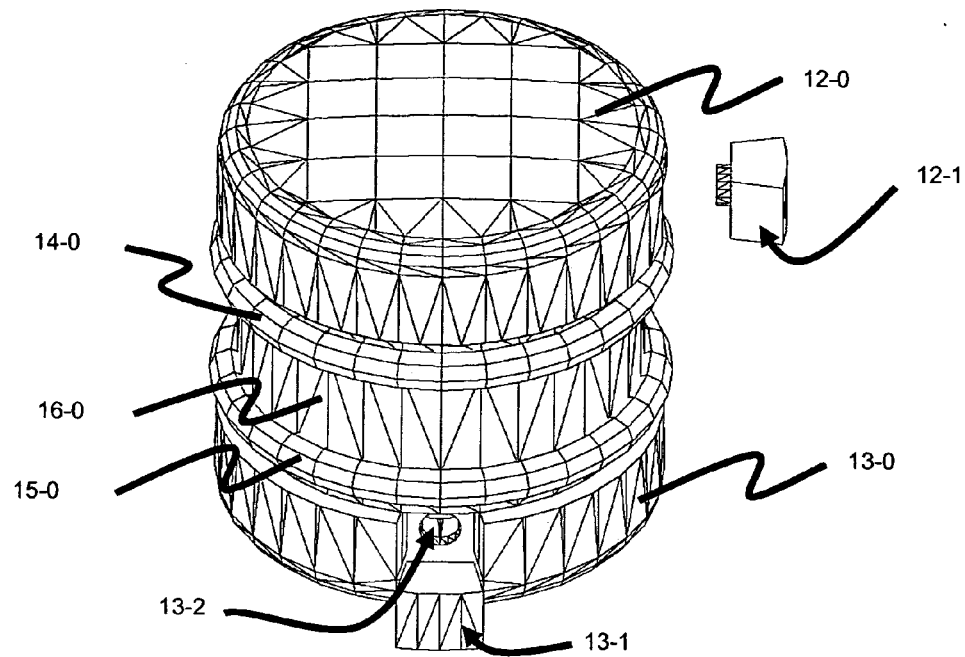
FIG. 52 depicts a cylindrical version of the embodiment of FIG. 41.

The cylindrical-joint embodiments discussed herein and depicted, for example, in FIGS. 30, 41, and 52 allow for booting (boots 6-0, 26-0, and 16-0) to add mechanical strength and to protect the internal mechanisms from the bio-environment, and, for modularity, to attach or detach the prosthesis after initial installation of the bone-fixed vertebral caps. In a preferred embodiment, the sealed boot can contain fluids (liquids and/or gases), viscous fluids, and/or colloidal suspensions of elastomer materials in a viscous fluid to lubricate the functional elements of the prosthetic devices and/or provide compressive resistance and motion dampening to the moving elements within the device. However, in certain applications of the subject device, the boot and/or lubricating properties may not be required and are not necessary to the motion and connective functionality of the prosthetic devices.

In a preferred embodiment, the boot can comprise a gas and/or liquid impermeable membrane. In a further embodiment, the boot can be reinforced with flexible fibers. In a still further embodiment, reinforcing flexible fibers are located on the exterior of the gas and/or liquid impermeable membrane.

Figure 42:
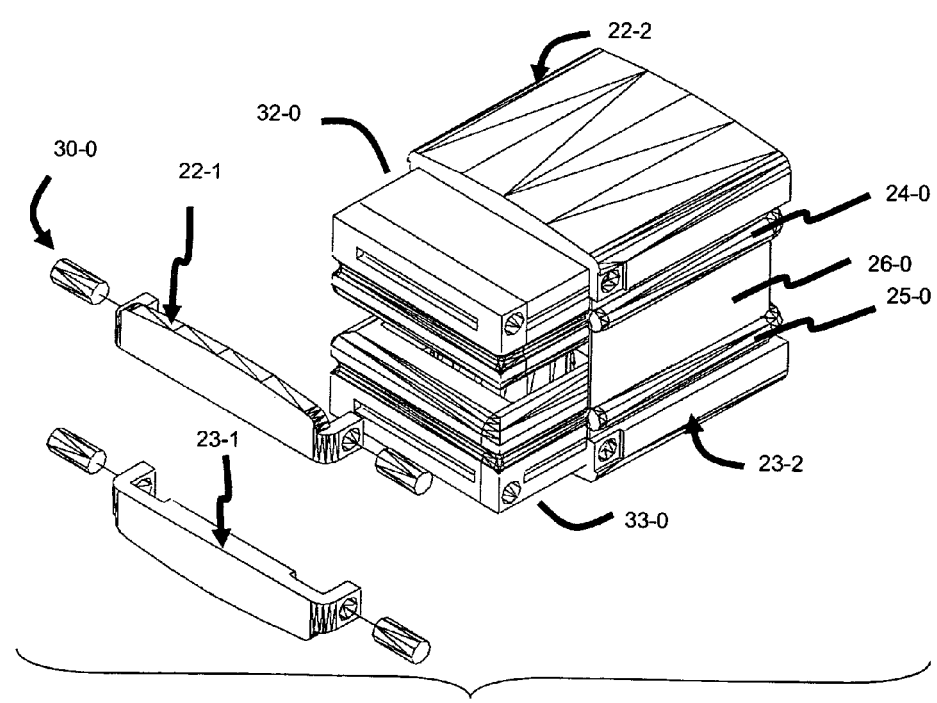
FIG. 42 depicts the modular prosthesis embodiment of FIG. 41 sliding out of a top and a bottom vertebral cap after removal of cap plate retaining bars. The boot and boot-retaining rings, have been cut away to show the grooved sides of the lateral and sagittal cylindrical joint platforms that mesh with tangs on the vertebral plates. Normally, the boot and its retaining rings form part of the modular unit and slide in and out with it. The mounting ring depressions around the platforms provide more secure binding of the boot to the lateral and sagittal joint platforms. The embodiment shown here is rectangular, but FIGS. 52, 53, and 54 show an alternative cylindrical embodiment. Ovoid geometries can also be used, depending upon clinical requirements.

The boot can be affixed to the prosthesis by any of a variety of techniques known to one with skill in the art. For example, in one embodiment, one or more clamps, clips or collars or similar devices known in the art can be used with the subject invention. In an alternative embodiment, shown for example in U.S. Pat. No. 6,237,662, the boot can comprise one or more specially formed or shaped edges (e.g., tire beads) that fit into and are held by ridges, channels or similar structures that circumscribe the interior of the end plates. In this embodiment, inflation of the boot interior with a liquid, colloidal suspension, viscous fluid, gel, gas, etc, helps maintain the position of the one or more boot edges within these ridges or channels. Alternative embodiments can omit the booting and capping, as shown in FIGS. 41 and 52, as dictated by clinical requirements. In a preferred cylindrical-joint embodiment, the prostheses slide tongue-in-groove into vertebral caps, for example as shown in FIG. 42. In this embodiment, the prosthesis locks to the vertebral caps to rigidly fix them to those plates and to allow efficient transfer of vertebral motion of the FSU directly to the lateral and sagittal cylindrical joint platforms that mate with the vertebral caps. As discussed above for the chambered-ball embodiment, boot ring indents on the sides of the cylindrical-joint prosthesis can create a fluid-tight enclosure of the internal mechanism when utilized with clamp rings to seal the boot against the lateral surface of the prosthesis. For booted versions, the compression and extension of the axial spring can cause splashing of a bio-inert hydraulic fluid around the bearing surfaces in all the embodiments. The bearing surfaces between the cylindrical joint platforms and the rocker-slider at each end of the axial spring, while depicted as lower order pairs, can also be realized as higher order bearings as discussed previously for the chambered-ball embodiment.

Figure 40:
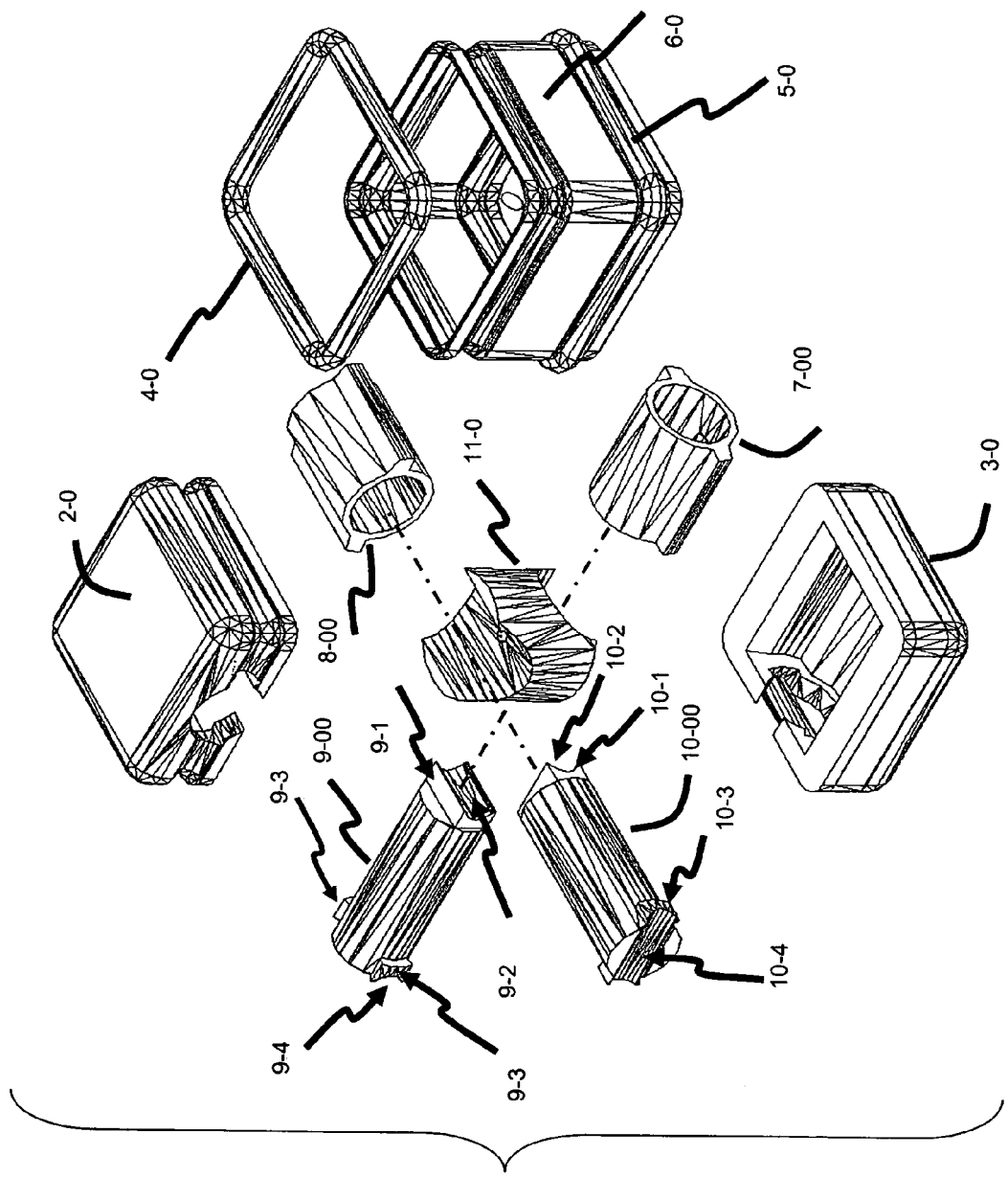
FIG. 40 illustrates a further alternative embodiment, wherein only the rotating axial spring provides dynamical response to vertebral motion in the spine. In this embodiment, the lateral and sagittal helical springs have been replaced by solid shafts about which their respective sleeves to rotate. In this embodiment, the shafts do not have tangs or lateral surface apertures. The lateral and sagittal cylindrical joint platforms and boot have the same embodiment as in FIG. 30.

In a preferred embodiment, shown for example in FIGS. 30 and 40, dynamical response is enabled via a three spring system incorporated into three mutually orthogonal cylindrical joints. A further preferred embodiment, shown for example in FIGS. 41 and 52, can achieve the same or similar load-bearing response as the embodiments shown in FIGS. 30 and 40. This further preferred embodiment can provide the same functionality, motion and load-bearing, as the chambered-ball embodiment, but with fewer, and more robust, parts. A still further preferred embodiment utilizes a cylindrical geometry of the prosthesis, shown for example in FIG. 52. A cylindrical geometry can have a more "natural" geometric fit into the FSU and lock together more simply and seamlessly without protruding elements. In a yet further preferred embodiment, the cylindrical geometry maintains the same motion and dynamic response as other embodiments.

Figure 31:
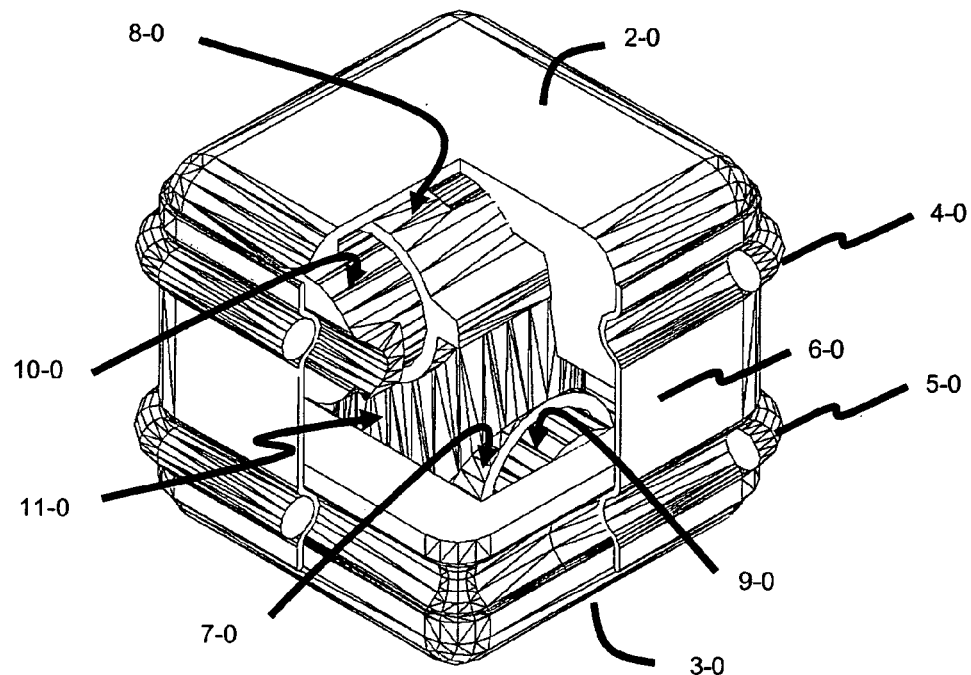
FIG. 31 shows a partial cutaway of the cylindrical-joint device, exposing the three orthogonal, machined, helical-spring-based cylindrical joints. These spring-based cylindrical joints can provide up to 6-Degrees-of-Freedom (DOF) of motion and dynamical response to vertebral motion of the FSU (Functional Spinal Unit) in which the prosthesis is placed. The combined motion, force, and moment-of-force response can be parameterized and engineered directly to correspond to the mechanical characteristics of the human disc, an important, novel distinction of this design. The 6-DOF dynamical response consists of compression/extension of the springs along the three orthogonal axes and torsion about each of those axes.
Figure 33:
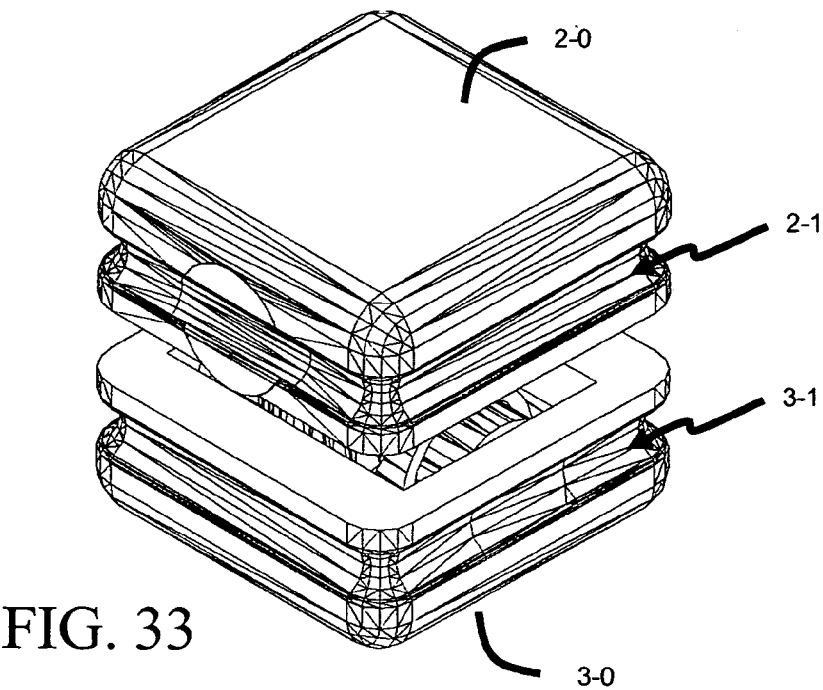
FIG. 33 shows a cylindrical-joint prosthetic device embodiment with the protective boot removed. This alternative embodiment does not isolate the mechanism from the surrounding environment.

To illustrate, the cylindrical-joint embodiment will now be described in more detail and with reference to parts that are illustrated on the accompanying figures. A protecting boot 6-0, clamped with "rings" 4-0 and 5-0 against the sagittal cylindrical-joint platform 3-0 and the lateral cylindrical-joint platform 2-0, protects the motion mechanism of the preferred embodiment FIG. 30. The clamping rings can fit into grooves 2-1 and 3-1 (FIG. 33). The cutaway version in FIG. 31 exposes the internal mechanism. Sagittal sleeve 7-0 slides and rotates about sagittal machined helical spring 9-0 to form the sagittal cylindrical joint, while lateral sleeve 8-0 slides and rotates about the lateral machined helical spring 10-0. The axial spring 11-0 connects the orthogonal lateral and sagittal cylindrical joints. The axial spring 11-0 opposes prosthesis compression, extension and twisting about the central axis of the FSU 42-0, while allowing these motions to within specifications as required by natural spinal motion. Similarly, the lateral and sagittal springs oppose translation along, and twisting about, the lateral joint axis 40-0 and the sagittal joint axis 41-0 (FIG. 37), respectively, but permit the motion as specified by natural motion. Thus, the tension of the spring allows for constant self-alignment of the spring along its central axis, but permits compression, extension, twisting and bending as required for natural spinal motion. These springs can be formed from strong, elastic, bio-inert titanium steel or other such suitable material.

Figure 32:
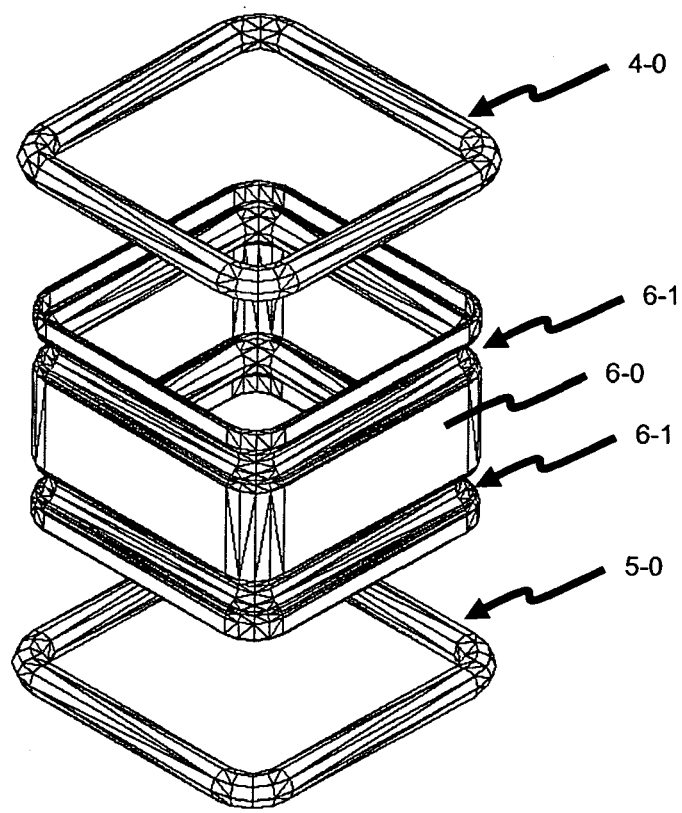
FIG. 32 shows an embodiment of a preformed, fiber-reinforced, flexible boot. Retaining "rings" hold the boot to embodiments of the prosthetic device and fit into the preformed grooves in the boot. These rings appear out of position in the figure to clearly show their structure.

The boot 6-0 can be constructed of fiber reinforced elastomers, as before, possibly pre-formed to add a certain amount of stiffness and integrity of shape, such as the corners and indents 6-1 of FIG. 32. FIG. 33 illustrates example boot indents 3-1 and 2-1 on the sides of the sagittal cylindrical-joint platform 3-0 and the lateral cylindrical-joint platform 2-0. The curved surface 3-8 can provide protection against damage to soft tissue. This figure also illustrates the use of the prosthesis without a boot.

The axial cylindrical joint consists only of the axial spring 11-0 which permits axial translations, through compression and extension, and rotations through axial twisting, but is rigid to lateral bending, to maintain spring performance and linearity of the spring axis. This joint fixedly, and rigidly, links to the sagittal 7-0 and lateral sleeves 8-0. The axial cylindrical joint is orthogonal to both the lateral and sagittal cylindrical joints.

The lateral cylindrical joint for this embodiment consists of a lateral spring 10-0, lateral sleeve 8-0, and a lateral cylindrical joint platform 2-0. The axis of rotation of the joint 40-0 corresponds to the lateral spring axis. The lateral spring 10-0 serves as the joint shaft and can be positioned in, e.g., by sliding through, the cylindrical orifice 8-7 on sleeve 8-0. Sleeve 8-0 serves as the proximal link of the joint and the platform 2-0 the distal link. In an alternative embodiment, the lateral spring is replaced with a solid lateral rod 10-00 which allows the lateral sleeve 8-0 to freely slide and rotate. The lateral joint axis is orthogonal to the sagittal joint axis.

The sagittal cylindrical joint for this embodiment consists of the sagittal spring 9-0, sagittal sleeve 7-0, and the lateral cylindrical joint platform 3-0. The axis of rotation of the joint 41-0 corresponds to the sagittal spring axis. The sagittal spring 9-0 serves as the joint shaft and can be positioned in, e.g., by sliding, through cylindrical orifice 7-7 on sleeve 7-0. Sleeve 7-0 serves as the distal link of the joint and the platform 3-0 the proximal link. In an alternative embodiment, the sagittal spring is replaced with a solid sagittal rod 9-00 which allows the sagittal sleeve 7-0 to freely slide and rotate.

Figure 34:
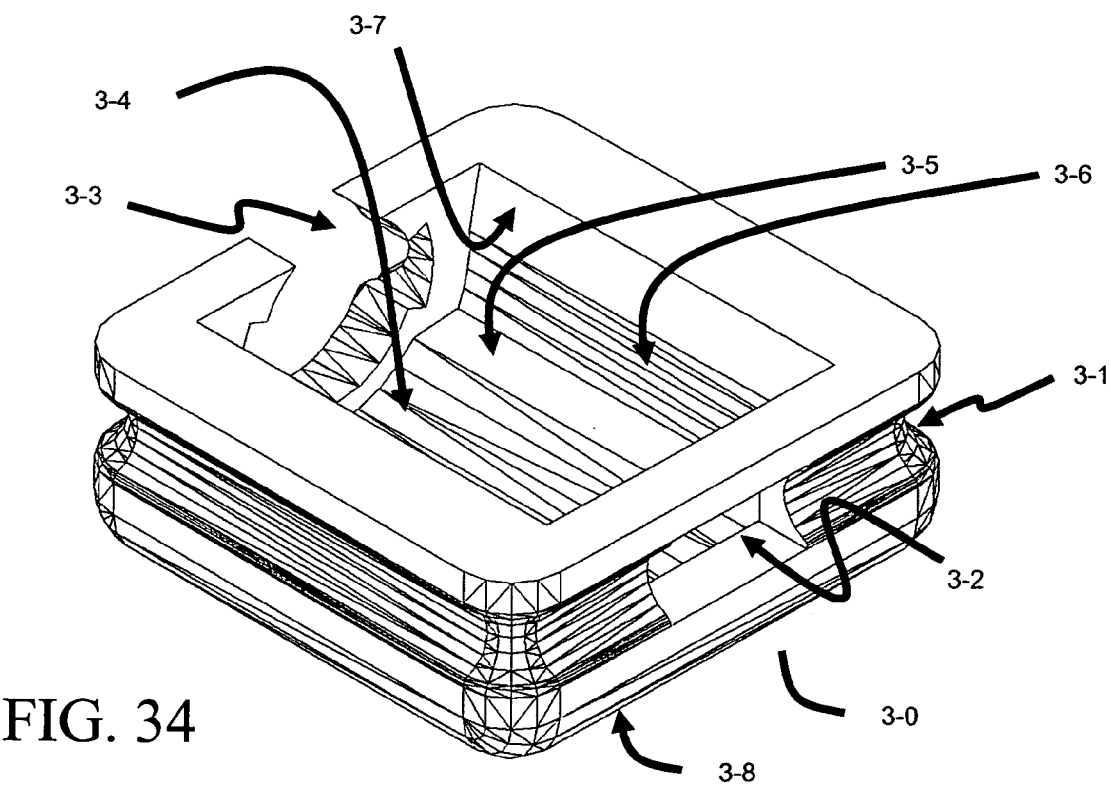
FIG. 34 shows an embodiment of the supporting platform of the (lower) sagittal cylindrical-joint of the cylindrical-joint embodiment of the device and various curved surfaces that can support cylindrical joint motion between itself and the interior mechanism. An alternate (upper) lateral cylindrical-joint platform of the device can be identical, but oriented upside down and at right angles to the sagittal cylindrical-joint platform. The lateral cylindrical-joint platform allows the insertion of a lateral machined helical spring, or lateral spring, and the sagittal cylindrical-joint platform allows the insertion of a sagittal machined helical spring, or sagittal spring. The lateral spring is able to provide mechanical properties that approximate natural human disc torsional dynamic response to lateral twisting as well as spring compression/extension opposing sagittal translations arising from sagittal motion of the FSU and the sagittal spring is able to provide mechanical properties that approximate natural human disc torsional dynamic response for spinal flexion and extension as well as spring compression/extension opposing lateral translations arising from lateral motion. The springs, designed to match human disc mechanical properties with regard to compression, extension and torsion for lateral and sagittal motion, respectively, do not have to be identical. In this embodiment, the springs anchor at both ends of their respective platforms. Preferably, the springs possess especial rigidity with respect to lateral bending to combat binding. Lateral and sagittal cylindrical joint surfaces can use various bearings other than lower pairs.

The sagittal cylindrical-joint platform 3-0 and the lateral cylindrical-joint platform 2-0 (FIG. 34) provide a cavity with complex surfaces to support joint sleeve translations (7-0, 8-0) along the associated cylindrical joint axis and rotations about that axis (40-0, 41-0). Planar surface 3-7 slopes at an angle to the plane perpendicular to the horizontal. This angle limits the amount of lateral or sagittal rotation of the central spring to one side. A corresponding surface on the other side limits the angle of rotation to that side. This slope parameter S can be customized per patient from 0° up to about 10° rotation about the lateral or sagittal axis for the current embodiment, depending on the amount of motion clinically desired. In one embodiment, the two sides can have the same surface slope S°, and, consequently, the same range of angular motion, namely, ±S°. In alternative embodiments, the sides can have different surface slopes S°. Circular surface 3-6 has a constant radius of curvature in any plane perpendicular to the sides of the platform. This radius equals the perpendicular distance from the surface to the cylindrical joint axis. The edges 7-1 and 8-1 projecting from the sleeves 7-0 and 8-0 have a circular surface 7-3 and 8-3 with the same radius of curvature in the plane mentioned. The upper surface 7-4 of projection 7-1 allows joining of the center spring to the sagittal sleeve, which can provide additional rigidity to the sleeve. The planar surfaces 7-2 intersect the horizontal plane at the approximately the same angle surface 3-7 makes with a plane defined by the sagittal and center axes. Planar surfaces 7-2 on the sagittal joint sleeve coincides with surfaces 3-5 on the sagittal joint platform 3-0 at maximum rotation of ±10° in either direction about the sagittal joint axis. This contact serves as a joint stop to rotation about the sagittal axis. The end-surface 7-8 of element 7-0 contacts the end plates of 3-0 at the extreme travel along the sagittal joint axis, limiting the amount of travel along the axis along sectioned cylindrical cavity 3-4. The sleeve and cavity lengths, therefore, can be designed to provide various translation ranges. For example, for a minimum sleeve length, a 11 mm cavity length allows ±1.5 mm translation along the sagittal axis while a 17 mm cavity length allow ±4.5 mm translations along the sagittal axis. Sleeve cylindrical surfaces 7-6 match the opposing cylindrical joint platform surface 3-4.

The surfaces 8-1, 8-2, 8-3, 8-4, 8-6 and 8-8 interact with the cavity surfaces of the lateral joint platform 2-0 in the same manner that surfaces 7-1, 7-2, 7-3, 7-4, 7-6 and 7-8 interact with the cavity surfaces of the sagittal joint platform 3-0 described in the previous paragraphs.

Sagittal spring 9-0 inserts into the sagittal cylindrical-joint platform 3-0 through opening 3-3 and into cylindrical orifice 7-7 of sleeve 7-0 resting on surface 3-4 and end 9-1 slips into orifice 3-2. If the spring has a tang 9-5 then part of the sleeve cylinder must be cut away to allow the spring to slide into place. The cut piece is then bonded back into place after complete insertion of the spring. In one method of manufacture, one side of the aperture, on top and bottom of each sleeve, extends to the edge of the device along the lateral surface of the cylinder, leaving a slot for the tang to slide through. This slot is then filled with a lateral-cylindrical-surface key that just fits the cut out piece of the sleeve, and is bonded into place.

The ends 9-3 and 9-1 of the spring either bond or press fit into the sagittal platform orifices 3-3 and 3-2, respectively, to lock the sagittal joint shaft into place. Indents 9-4 and 9-2 on the ends 9-3 and 9-1 make allowances for a boot clamp. A similar method applies to the lateral cylindrical-joint assembly involving lateral spring elements 10-1, 10-2, 10-3 and 10-4 and the lateral joint platform 2-0.

Further in this embodiment, the central spring has a center bore 11-3 whose size can be dictated by the spring characteristics desired. In one embodiment, surfaces 11-4 permit attaching the central spring to the sagittal and lateral sleeves. In alternative embodiments, the three elements can be manufactured as an integrated piece. Curvilinear cuts 11-1 and 11-2 can allow fitting the central spring over the sagittal and lateral sleeves. The complete integration of the center spring with the sagittal and lateral sleeves 15-01 is illustrated, for example, in FIG. 38.

Figure 35:
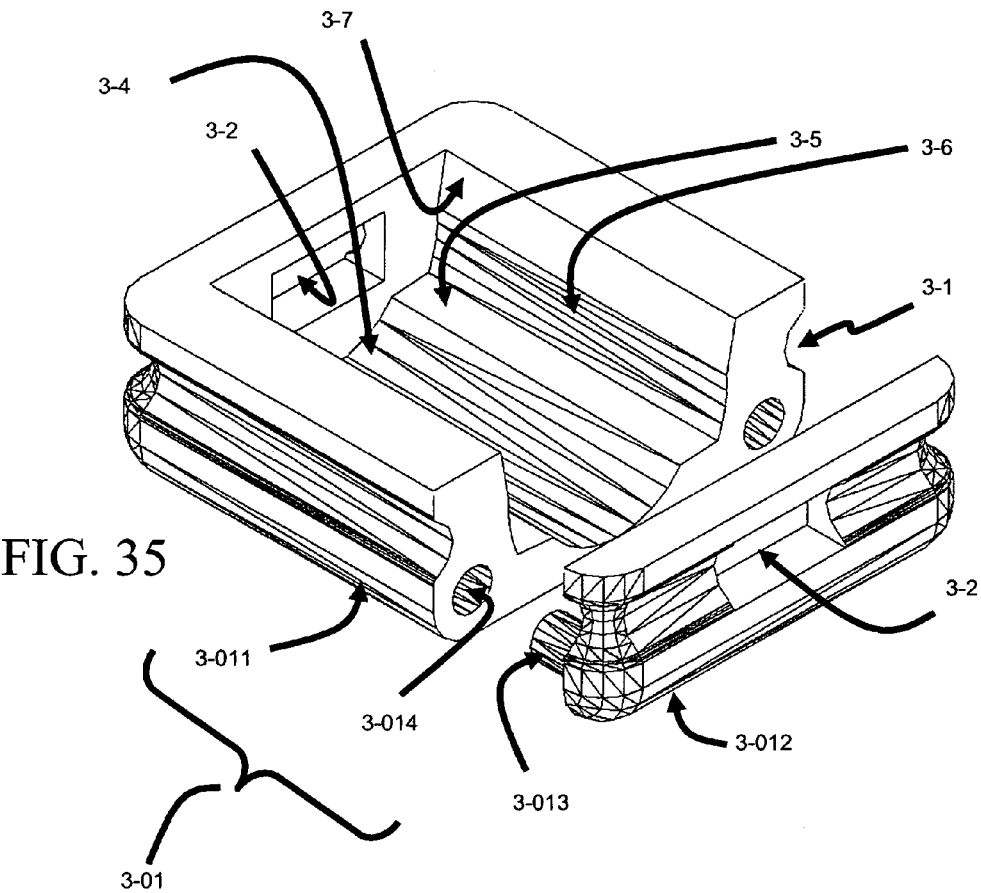
FIG. 35 illustrates an alternative embodiment of the cylindrical-joint embodiment, wherein the cylindrical joint platform has a main body and an endplate with one or more peg-and-hole joints. In this embodiment, the end-tang holes for the joint spring are identical in this case. The corresponding spring has a structure shown, for example, in FIG. 36. In this embodiment, after assembly of the complete internal mechanism, it can be joined to the lateral- and sagittal cylindrical-joint platforms by inserting the spring into one end and then capping the other end with the endplate.
Figure 36:
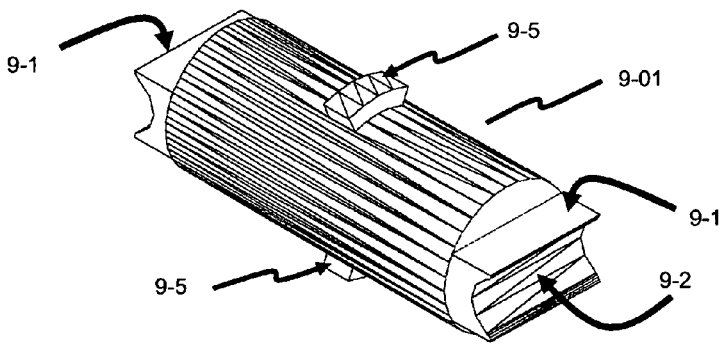
FIG. 36 shows a spring with identical end-tang structure that is compatible with the cylindrical joint platform structure of FIG. 35.

Modification of the cylindrical joint platform 3-01 (FIG. 35) and the lateral and sagittal springs (FIG. 36) can enable an alternative assembly method. For example, the lateral and sagittal springs can be positioned into their sleeves and fixed orthogonally to the axial spring in any desirable way. Further, the sagittal sleeve-spring combination (7-0, 9-0) can be positioned onto the joint platform large body 3-011, a first end of the spring 9-1 tang can be fit into, e.g., via press fitting, the orifice 3-2 in the closed end of the platform 3-011. The second end of the spring tang 9-1 of the spring can be fit into, e.g., via press fitting, into the orifice 3-2 of the endplate 3-012. The pegs 3-013 can be fit into holes 3-014 of element 3-011, via for example press fitting. Once assembled, the endplate 3-012 can be bonded to element 3-011. The same process can be repeated for the assembly of the lateral spring to complete the assembly of the prosthesis.

Figure 38:
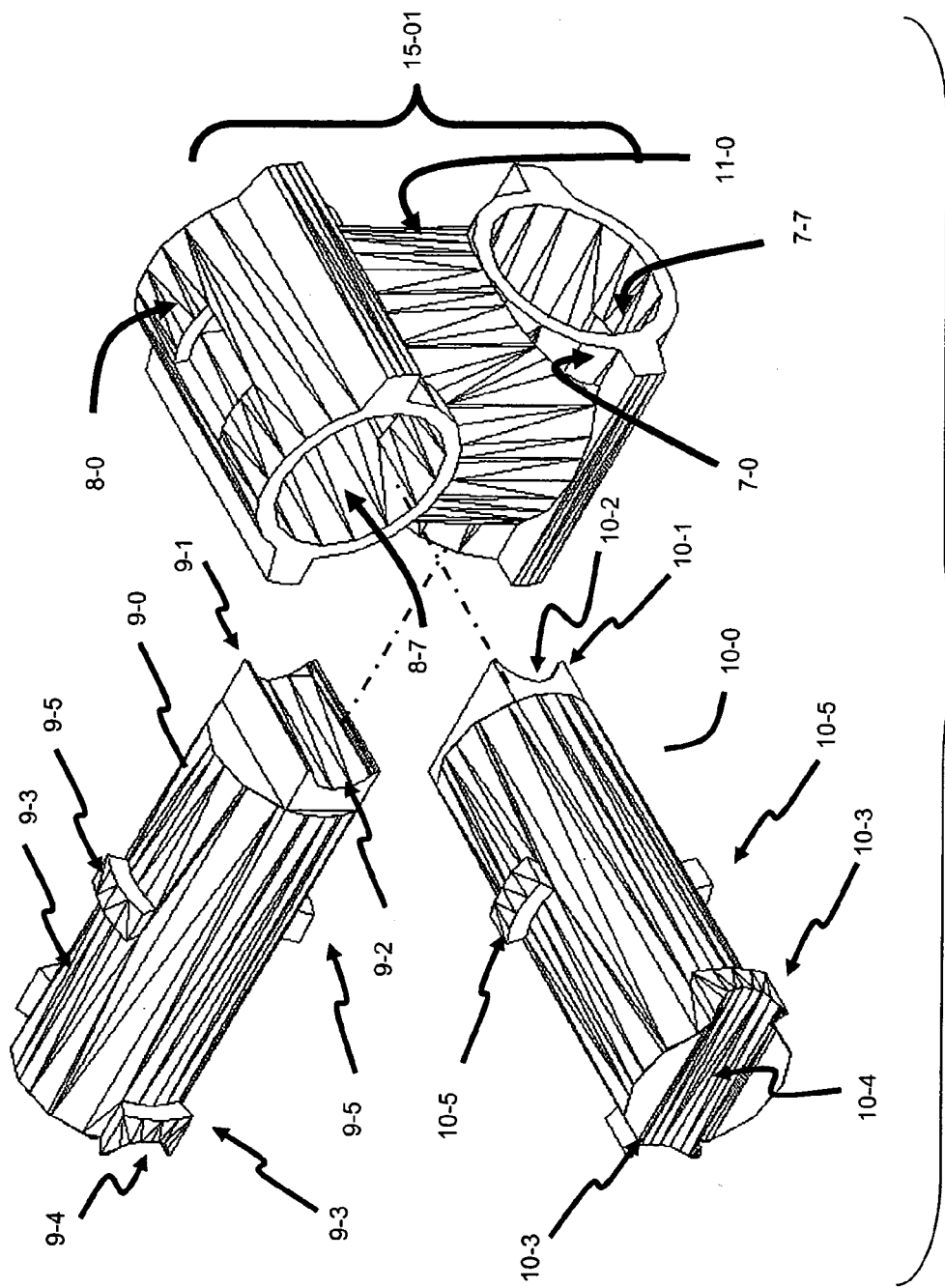
FIG. 38 shows a partially exploded view of the 6-DOF, three orthogonal cylindrical joints embodiment with the lateral and sagittal springs slipped out of their sleeve joints. The joint sleeves rigidly attach to the axial spring. In this embodiment, centrally located tangs on the lateral and sagittal springs essentially divide the spring into two series connected springs. As the axial spring joint moves the tangs along the axis of the lateral/sagittal spring, one side of the lateral/sagittal spring compresses and the other side of the spring extends. If the axial spring turns about the spring axis, the lateral/sagittal spring torsion resists the twisting motion, too. This tang fits in various sized lateral-cylindrical-surface apertures on the cylindrical surface of its respective sleeve. The larger the lateral-cylindrical-surface aperture in the sleeve, the less the lateral/sagittal springs become engaged by axial spring motion and the less resistance proffered to that motion. If the sleeve aperture, after the key is in place, is just large enough to enclose the tang tightly, such as in a pressure fit, any small motion of the axial joint can be opposed by compression/extension along the axis of the spring or torsion about its axis.
Figure 39:
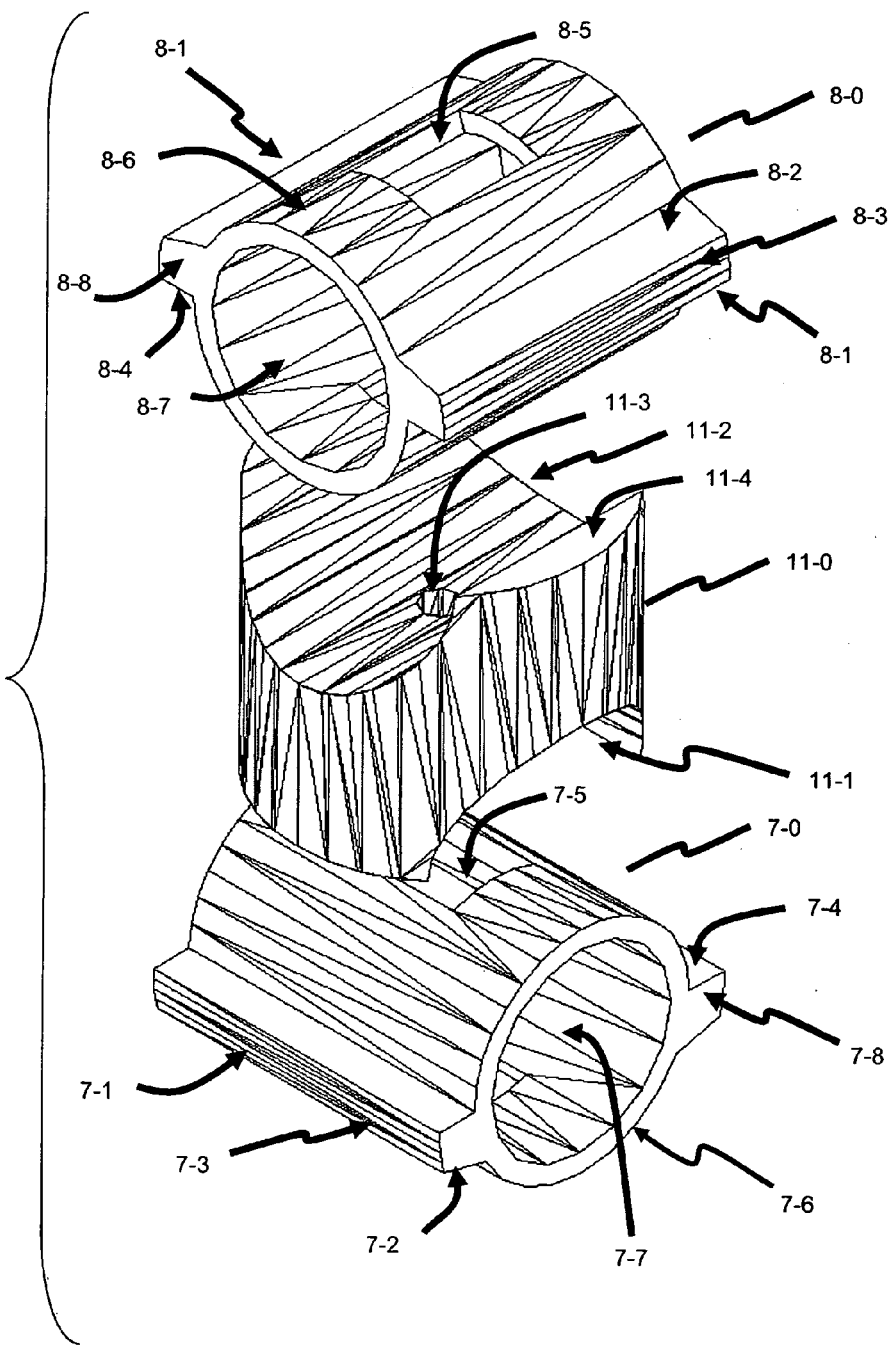
FIG. 39 shows an exploded view of an embodiment of the axial spring and the lateral and sagittal sleeves of the cylindrical-joint embodiment. In the final assembly, these elements attach to each other rigidly. The central bore down the axial spring allows for an appropriately designed machined helical spring. The lateral and sagittal springs can also have central bores (not shown) when machined.

With regard to FIGS. 37, 38 and 39, regardless of the assembly process or elements used, it can be preferable for each tang 10-1 of the lateral spring 10-0 and 9-1 of the sagittal spring 9-0 to be mechanically grounded at each end of its corresponding cylindrical joint platform 2-0 and 3-0, so as to enable torsion resistance to rotation of the axial spring 11-0, and the fixedly attached sleeves 7-0 and 8-0, about the lateral axis 40-0 and the sagittal axis 41-0. To accomplish torsion, the central tangs of the lateral spring 10-5 and the sagittal spring 9-5 must fit into the sleeve apertures 8-5 and 7-5. The sizes of the tang and the aperture determine how much rotation is required before the sleeve engages the tang, both in twisting and sliding the sleeve about axes 40-0 and 41-0. For example, if the angle of arc of the apertures exactly equals the angle of arc of the tang, then any twist can immediately engage the spring torsion response. If, however, the length of the aperture is, for example, 0.5 mm wider to each side of the central tang, the sleeve can then slide ±0.5 mm before engaging any compression/extension response from the spring.

An alternative embodiment utilizes no central spring tangs 9-00, 10-00, such that the sleeves 8-00 and 7-00 require no apertures and slide and rotate freely along and about the spring without engaging it (for example as shown in FIG. 40). In a further alternative embodiment, the sagittal and lateral springs can be replaced with a solid or semi-solid sagittal rod 9-00 and a solid or semi-solid lateral rod 10-00 about which the sleeves 8-00 and 7-00 slide and rotate freely. In these embodiments, the dynamic response of the device can be reduced, but still preserved is the complete six-degrees-of-freedom of motion and the kinematic linkage between the upper and lower vertebrae of the FSU.

The sizes of the sleeve apertures (7-5, 8-5) and spring center tangs (9-5, 10-5) therefore, serve as design parameters that allow direct control of the prosthesis response to torsion and translations about axes 40-0 and 41-0.

The axial spring 11-0 compresses and extends along axis 42-0 and rotates about that axis. The axial spring is designed to be rigid to moments of force about 40-0 and 41-0. The axial spring 11-0 rigidly attaches to the lateral sleeve 8-0 and sagittal sleeve 7-0 forming a rigid structure to lateral and sagittal bending. Such forces and moments can tend to move this structure relative to the joint platforms and, in general, engage all three springs to bear the load.

Figure 43:
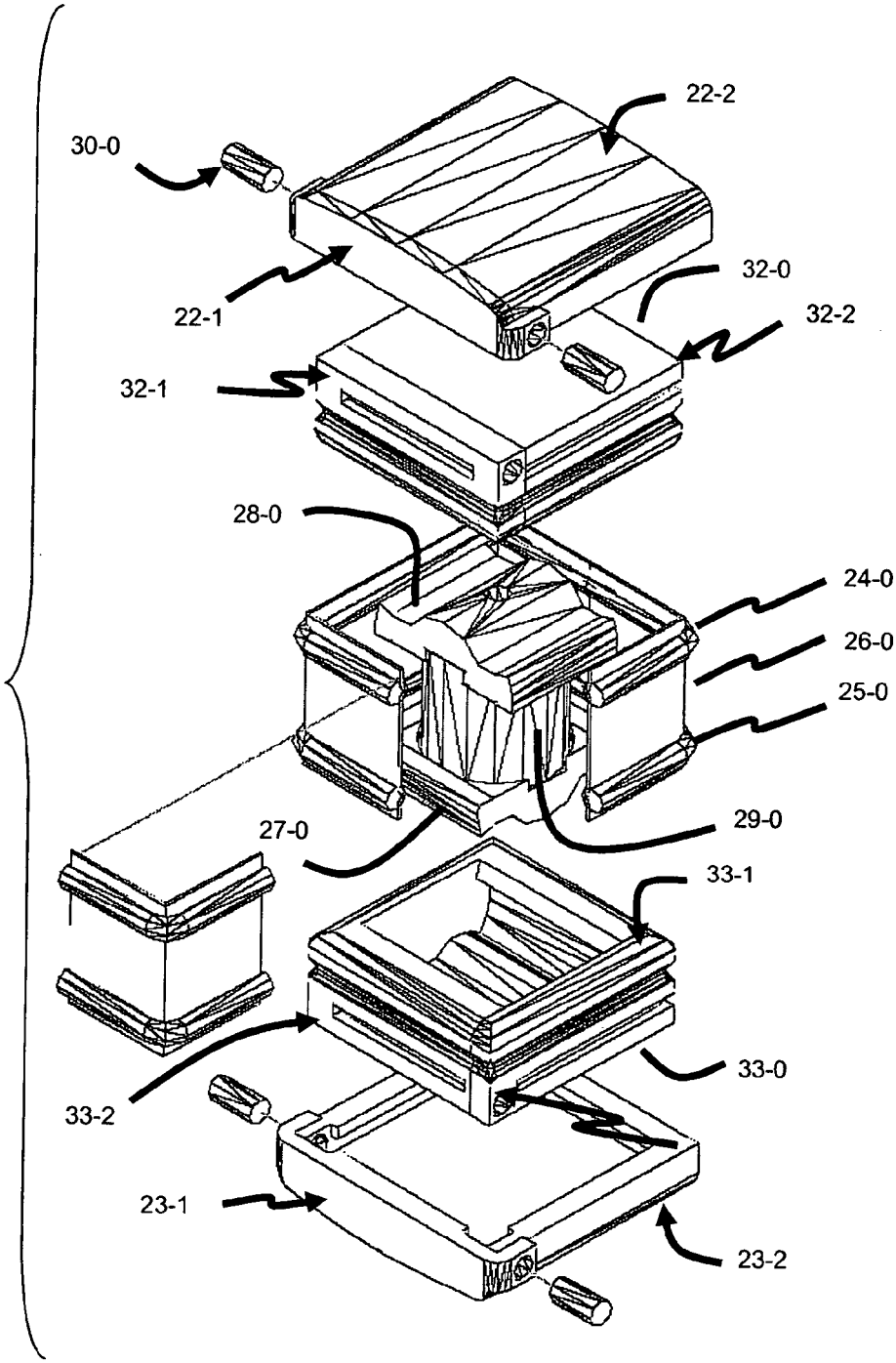
FIG. 43 shows an exploded view of the embodiment of the rocker-slider prosthesis described for FIGS. 41 and 42 with a portion of the boot and boot retaining rings cut away to show the mechanism that controls the motion and dynamical response of the prosthesis. This embodiment of the mechanism differs from the previous embodiment. A cylindrical joint attaches to each end of a large, rotating axial spring. The upper element, the lateral cylindrical-joint, is orthogonal to the lower element, the sagittal cylindrical-joint. Each cylindrical joint consists of the joint platform and the rocker-slider element that attaches rigidly to the axial spring.
Figure 44:
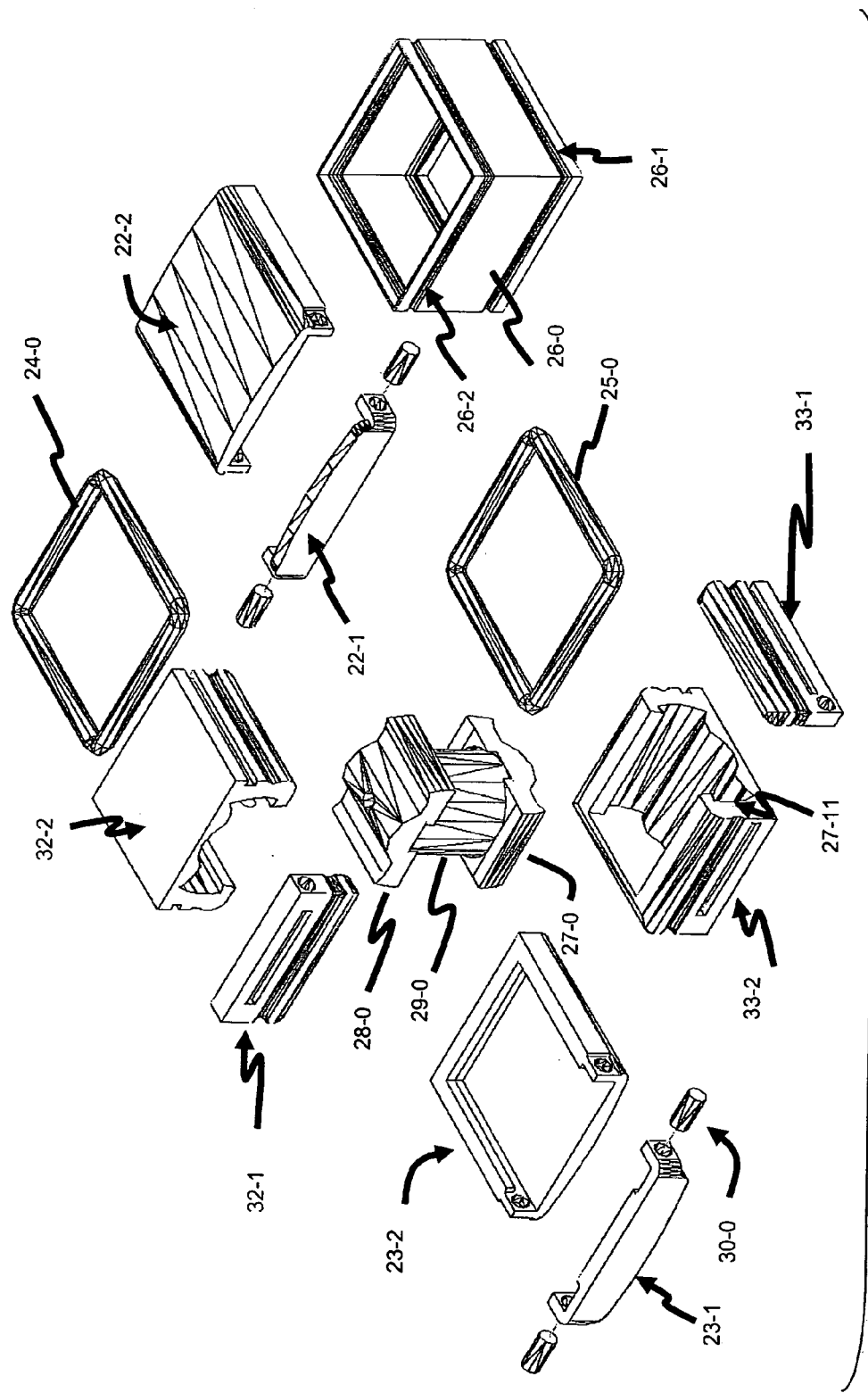
FIG. 44 shows the major elements of the embodiment of FIG. 41. In this embodiment, the lateral and sagittal cylindrical joint platforms consist of two elements joined by the clamping pins or screws that hold the modular prosthesis securely to the vertebral plates. The grooved sides of the platforms mesh with matching runners, or tongues, on the vertebral plates to secure the prosthetic module about its circumference to the plates.
Figure 46:
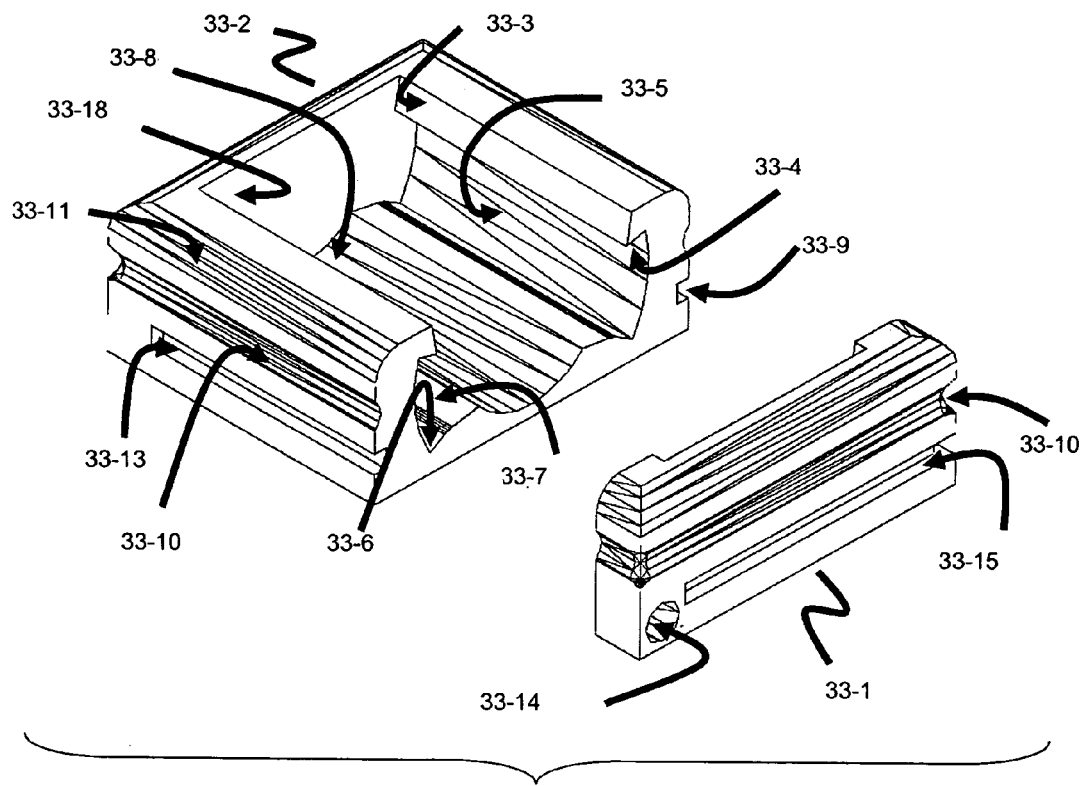
FIG. 46 illustrates the sagittal cylindrical-joint platform structure for the modular rocker-slider embodiment that slides into bone-fixed vertebral plates. The platform consists of a main body and an endplate. The endplate bonds to the main body, after the central mechanism has been inserted. Interlocking surface elements between the two parts (not shown) and other assembly techniques can be employed to strengthen this join. The grooved sides provide a tongue-and-groove insertion into of the upper vertebral cap. The clamping bar has a tongue that meshes with the front groove of the platform. The sides also have an indent for securing a boot with a clamping ring. The figure also highlights the various surfaces that mesh with the rocker-slider.

III. Rocker-slider Spinal Disc Prosthesis:

The preferred embodiment shown, for example, in FIGS. 41, 42, and 43 employs vertebral caps 22-0 and 23-0, each consisting of end brace 22-1 and 23-1 and main body 22-2 and 23-2. One or more pins, screws, removable rivets 30-0, or similar devices, can be inserted into holes 23-14→23-12→33-14 and 23-16→23-10→33-16 (see FIGS. 48 and 51) to secure the end brace 23-1 via tab 23-8 to the tab 23-7 on the main body 23-2, as well as attaching the sagittal cylindrical-joint platforms endplate 33-1 and main body 33-2 (FIG. 46). Vertebral cap 22-0 main body 22-2 is similarly joined to its end brace 22-1 and joint platform endplate 32-1 and 32-2. Complete design of vertebral caps hinge on the FSU involved in the prosthesis. Each vertebral cap must feature the ability to secure the prosthesis in a stable configuration and allow for a previously installed prosthesis to be removed without further invasive bone procedures.

The inside surface 23-6 of the lower vertebral cap 23-2 is flat and smooth to accommodate a corresponding flat smooth surface on the underside of sagittal joint platform 33-0. A similar situation holds for the upper vertebral cap 22-2. The lower surface of the vertebral caps can be modified with standard techniques for encouraging bone growth and anchoring the caps into bone. For example, surface 23-3 of cap main body 23-2 might consist of a porous titanium steel matrix to encourage bone fusion. A ridgeline or matrix of teeth can also be used to anchor the caps. Whatever technique used for bone fusion, the method should discourage bone growth on and around the end braces 22-1 and 23-1 since they should be removable to retain their intended function. Thus, for example, the end braces can have generally smooth underneath surfaces and be impregnated with growth suppression drugs, if necessary.

The axial cylindrical joint is the axial spring 29-0. The cross pattern 29-2 is the distal link and rigidly connects to rocker-slider 28-0. Cross pattern 29-3 (not seen in FIG. 45A) is the proximal link and rigidly inserts into cross pattern indent 27-7 of rocker-slider 27-0. The axial spring is generally rigid to longitudinal forces, but can permit torsion about axis 29-9.

Figure 47:
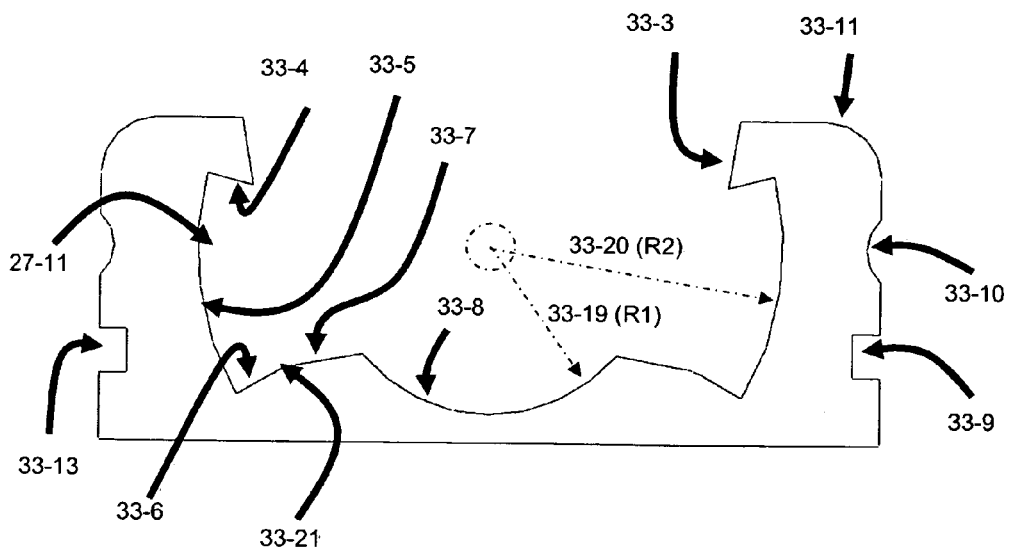
FIG. 47 clarifies the specification of the various interface surfaces between the platform and the rocker-slider component.

In one embodiment, the sagittal cylindrical joint consists of the sagittal rocker-slider 27-0 and the sagittal cylindrical joint platform 33-0. The axis of rotation of the joint 27-9 corresponds to the axis of the half-right circular cylinder surface 27-2. There is no joint shaft per se. In this embodiment, the rocker-slider constitutes the distal link for the sagittal cylindrical joint and the platform 33-0 the proximal link. The sagittal joint axis is orthogonal to the lateral joint axis, as before. The rocker-slider wing elements 27-10 project from the rocker slider and are positioned within rocker-slider wing channels 27-11 and surfaces 27-5 have the same radius of curvature as surfaces 33-5 (FIG. 47). When the rocker slider rotates about the sagittal axis 27-9, surface 27-2 engages with, preferably by sliding, and surface 33-8 and surfaces 27-5 engage with surfaces 33-5, preferably by sliding At one rotation, surfaces 27-6 conform to surfaces 334 and at another rotation, surfaces 274 and 27-3 conform to surfaces 33-6 and 33-7, respectively. The ridge 33-21 in general constitutes the intersection of the planar surfaces 33-6 and 33-7. The different slopes permit element 27-10 to be larger and more robust. In a further embodiment, planar surface 33-18 blocks one end of the sagittal joint cavity.

In a further embodiment, the lateral cylindrical joint for this embodiment consists of the lateral rocker-slider 28-0 and the lateral cylindrical joint platform 32-0. The axis of rotation of the joint 28-9 corresponds to the axis of the half-right circular cylinder surface 28-2. In this particular embodiment, there is no joint shaft per se. The rocker-slider constitutes the proximal link for the lateral cylindrical joint and the platform 32-0 the distal link. The lateral joint axis is orthogonal to the sagittal joint axis, as before. The elements 28-2, 28-3, 28-4, 28-6, 28-10 play the same roll with respect to the cavity surfaces of the lateral joint platform 32-0 as does 27-2, 27-3, 27-4, 27-6, 27-10 do with the cavity surfaces of the sagittal joint platform 33-0 (FIG. 47) as explained above. Planar surface 32-18 of the lateral joint platform blocks one end of the sagittal joint cavity.

Figures 45A, 45B:
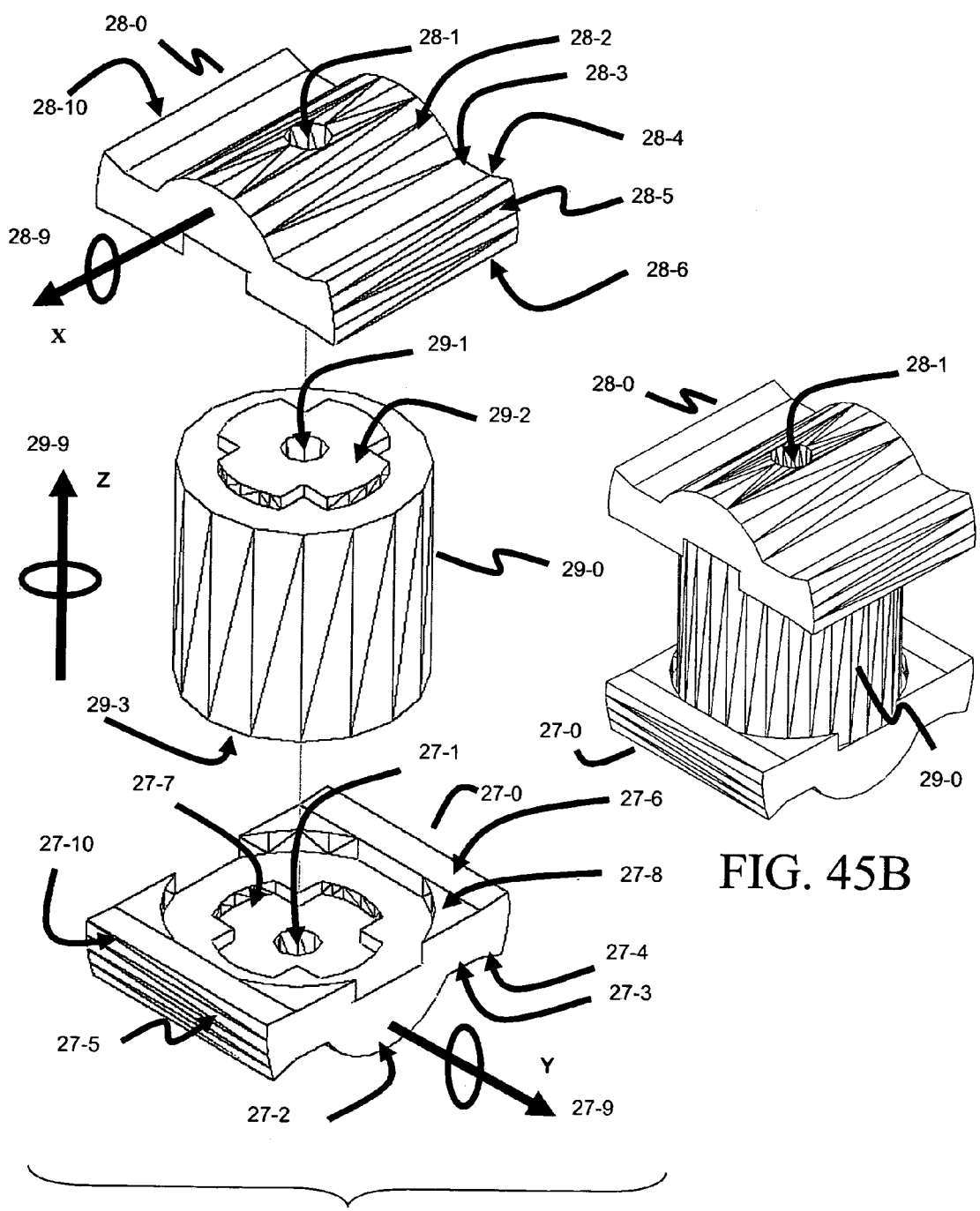
FIG. 45A illustrates the separate components of the internal 6-DOF kinematic chain of the embodiment of FIG. 44. In this embodiment, one end of an axial spring fixes to an upper, lateral rocker-slider element and the other end to a lower, sagittal rocker-slider element. A rocker-slider allows relative translation and rotation, about its principal axis, with respect to the platform in which it moves. Further in this embodiment, the rocker-sliders do not provide any dynamical response other than friction forces that oppose joint motion. In an alternative embodiment, the rocker-sliders can be mounted with cushioned ends that can provide compression resistance to sliding motion in those instances where the rocker-slider does not translate too much in either direction. The shape of the rocker-slider, once inserted from the side of the platform, locks it into the platform when enclosed by the end pieces. The surfaces on each side of a rocker slider permit translation and rotation about the joint axes without jamming. Each rocker-slider provides at least two degrees-of-freedom, as does the axial spring, for a total of 6-DOF. Lateral and sagittal cylindrical joint surfaces can also use various bearings other than lower pairs.
FIG. 45B illustrates the embodiment of FIG. 45A wherein the rocker-sliders are fixed onto each end of the axial spring.

The central mechanism FIG. 45A of the embodiment of FIG. 41 consists of a lateral rocker-slider 28-0, a sagittal rocker-slider 27-0 and a large central machined helical spring 29-0. The helical spring can comprise one or more of a variety of bio-inert materials, including, for example, titanium steel, titanium-carbide-coated stainless steel, or other material suitable for spring realization. The spring can be affixed to the rocker sliders by a variety of techniques known to a person with skill in the art. For example, in one embodiment, the spring can be press fitted to one or both of the rocker sliders, as shown in FIG. 45B. In this embodiment, the cross pattern indent 27-7 of the sagittal rocker-slider 27-0 fixedly mates with a cross pattern projection on the underneath side of the spring. A similar mating occurs with cross pattern projection 29-2 on top of the spring with the underlying cross pattern indent on rocker-slider 28-0. The cross patterns accommodate large torsion loads by the rocker-sliders and can provide more surface contact than a planar surface. These features can enhance secure bonding and joint strength to torsion loads. In a further embodiment, each rocker slider 28-0 and 27-0 is machined from a single element of bio-inert titanium steel or other suitable bio-inert material. The corner elements 27-8 allow extra length and support for the central spring. In a still further embodiment, the entire mechanism is machined from a single piece of material. This embodiment can, perhaps, increase the cost and decrease the useful length of the axial spring. But, this embodiment can, possibly reduce chances of failure during operation. The pass through holes 27-1 and 28-1 permit fluids to flow freely onto the cylindrical joint surface defined by the cylindrical surfaces 28-2 and 32-8 and 27-2 and 33-8. The size of the cylindrical hole 29-1 of the axial spring 29-0 can be dictated by the spring performance requirements for each patient. In addition, the holes in the rocker-sliders can be the same size. The rocker-sliders, being solid, can add robustness to the joints.

Figure 51:
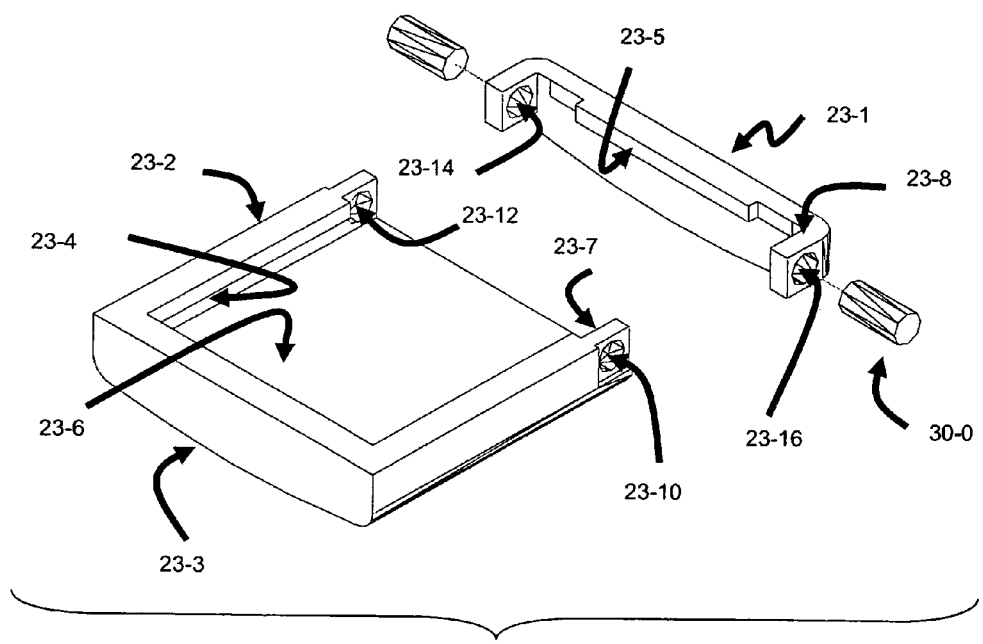
FIG. 51 shows the structure of the top and bottom vertebral caps. The main body fixes to the bone and has surface elements to encourage bone fusion. The clamp bar does not have such elements and can be coated to prevent bone fusion as it must be removable to preserve the modular attachment and detachment feature of various prosthesis models so that damaged or worn out prostheses can be replaced with minimum invasive procedures on the vertebral bone structure.

In a further embodiment, the joint platforms 32-0 and 33-0 (FIGS. 42 and 43) have square-profiled grooves around their lateral surfaces to permit tongue-in-groove joins to the vertebral caps. For example, in this embodiment, the sagittal joint platform 33-0 has grooves 33-9, 33-13, 33-15 (FIG. 46) and a groove like 33-15 on the back end-plate. These grooves fit vertebral cap tongues 23-4, 23-5 on the upper vertebral cap 23-0, consisting of 23-1, 23-2 (FIG. 51). Grooves 32-9 and 33-13 on the lateral joint platform 32-0 (FIG. 49) serve a similar purpose as the grooves 33-9, 33-13 on the sagittal joint platform. The other grooves on 32-0 equivalent to 33-15 and the groove on the back lateral surface cannot be seen in the diagram. Holes 33-14 and 33-16 on the sagittal joint platform permit locking (and reversibly unlocking) the vertebral end-plate 23-1 to the sagittal joint platform element 33-1 and 33-2 by means of screws 30-0. Similarly, holes 32-14 and 32-16 on the lateral joint platform permit locking (and reversibly unlocking) the vertebral end-plate 22-1 to the sagittal joint platform element 32-1 and 32-2 by means of screws 30-0.

Alternative embodiments of the sagittal and lateral joint platforms can utilize shapes other than square or rectangular groove profiles. But, in a preferred embodiment, the profiles are able to totally restrain relative motion between the vertebral caps and the cylindrical joint platforms. Thus, in a still further preferred embodiment, square or rectangular profiled tongue-in-groove profiles are used to join and secure the cylindrical joint platforms to the vertebral caps. This preferred embodiment can provide the capability of removing the end brace and sliding the prosthesis out of the FSU without removing the vertebral caps or damaging bone. This modular capability can permit surgeons to replace aging, installed prostheses that are loosing functionality, with the same, improved, or newer versions.

The rocker-slider arrangement 27-0 and 28-0, joined with central spring 29-0, differs from the cylindrical-joint sliding mechanism of prior art devices, such as for example, Khandkar et al (U.S. Pat. No. 6,994,727 B2 Feb. 7, 2006 FIG. 1), in several significant respects. The interlocking, concave-arcate structures of the joint platforms 32-0 and 33-0, of the subject invention, allow kinematic chaining of the rocker sliders 27-0 and 28-0 to the upper and lower sliding bearing surfaces within the lateral and sagittal joint-platforms 32-0 and 33-0, i.e. the rocker sliders can be slidably fixed to the platform. The interlocking, concave-arcate surfaces feature also permits rotational motion of the rocker-slider along the entire length of the inverted arcate surface without compromising the slidably fixed constraint of the rocker-slider or the mechanical interconnection from lower vertebra to superior vertebra in an FSU. Further, the mechanical interconnects (kinematic chaining) of the device do not compromise the relative motion capability between vertebra joined together by the prosthetic device. In general, the kinematic chaining of the motion elements within the prosthesis maintains mechanical stability and integrity of the prosthesis as a unit without compromising motion capability.

In a further preferred embodiment, two or more indents or grooves 32-10 and 33-10 can allow clamps 24-0 and 25-0 to affix a boot to the cylindrical joint platforms 32-0 and 33-0 to seal out external fluids or seal in internal fluids. The indents or grooves can comprise any of a variety of shapes or forms. For example, the indents can comprise a squared, semi-oval, triangular, semi-circular configuration, or combinations thereof. In a preferred embodiment, the indents comprise a circular configuration. In a further preferred embodiment, neither these indents, nor an installed boot 26-0, which can also have fiber reinforced indents 26-1 and 26-2, interferes with the modular function described above. Thus, in a most preferred embodiment, a completely assembled prosthesis, which includes a boot 26-0, can be installed by a surgeon as a single unit, once the vertebral caps 22-0 and 23-0 have been installed.

In another embodiment, springs or elastomers can be inserted into the lateral and/or sagittal rocket slider wing channels 27-11, in which the rocker slider wing elements 27-10 and 28-10 move, to oppose the motion of the rocker sliders. In one embodiment, the springs and/or elastomers can be fastened at one end to the joint-platform and at the other end to the rocker slider. In an alternative embodiment, the booted version of the device can be filled with viscous fluids or colloidal suspension of viscous fluids with a large number of small biocompatible elastomer particles in suspension to interact with the boot and the moving elements of the device to produce resistance to motion or to absorb sudden shocks. For example, a sudden compression force can be partially absorbed by the colloid compressing the small elastomer particles and the resistance of the boot to the increased fluid pressure. The size of the elastomer particles in the colloid can be spheres varying from 0.25 mm in diameter to as small as 1 micron or even less and have a durometer selected for the application. The number and size of particles will dictate the compressibility of the colloidal suspension under shock.

The separate endplate 32-1 of the lateral cylindrical joint platform and the separate endplate 33-1 of the sagittal cylindrical joint platform can permit the insertion of the internal mechanism, the rocker sliders 27-0, 28-0 and the axial spring 29-0, into the device. Once the central mechanism is in place, the endplates can be fixedly attached to their respective platform main bodies 32-2 and 33-2. In a preferred embodiment, the endplates are permanently attached to their respective platform main bodies. To complete the assembly, the boot 26-0 and the clamping rings 24-0, 25-0 can also be attached. In a preferred embodiment, for use as a cervical prosthesis, the endplates can comprise a thickness of approximately 2.0 mm to approximately up to half the length of the joint platform. In a particular preferred embodiment, for use as a cervical prosthesis, the endplates can comprise a thickness of approximately 2.0 mm to approximately 9 mm. In more particular preferred embodiment, for use as a cervical prosthesis, the endplates can comprise a thickness of approximately 2.0 mm to approximately 7.0 mm. In these embodiments, the surfaces 32-17 and 33-17 (shown for example in FIGS. 48 and 50) will include at least a portion of the motion space of the rocker-sliders. For example, an endplate that is 2 mm thick will include about 0.5 mm of rocker-slider motion space. In another example, an endplate that is 9 mm thick will include about 8.5 mm of rocker-slider motion space. In a preferred embodiment, a cervical prosthesis assembly of the subject invention can fit into a circumscribing rectangular solid whose height is from about 8 mm to about 14 mm, and whose width is from about 14 mm to about 20 mm, and whose depth is from about 14 to about 20 mm. However, it should be understood that other dimensions are possible, and the devices can be scaled to any appropriate size dictated by their application. In addition, the prosthesis need not be scaled in total. Different elements of the prosthesis can be scaled differently, to meet different requirements, as long as the contact surface conformability and required motion limits are maintained. By way of further example, a lumbar prosthetic can be circumscribed by a rectangular solid approximately 40 mm wide, approximately 30 mm deep, and approximately 20 mm high.

One embodiment of the inside surface structure of the cylindrical joint platforms 22-0 and 23-0 can be seen in FIGS. 46 and 47. In this embodiment, these surfaces allow the rocker-slider elements 28-0 and 27-0 to slide back and forth and rock within a cylindrical channel. For purposes of this application, it should be understood that the features and elements of the sagittal cylindrical-joint platform correspond to the lateral cylindrical-joint platform. Note further that for purposes of description, the most positive x of any element is its front and the most positive y of the element constitutes its left side.

In a preferred embodiment, the cylindrical bearing surface 27-2 of the sagittal rocker-slider 27-0 can slide back and forth within the half-cylindrical channel 33-8 of platform 33-2 and rotates about the center of curvature 33-19 of that channel (FIGS. 46 and 47). The sagittal spring axis 27-9 (FIG. 45A) passes through this center. Planar surface 27-6 has a slight tilt and is determined by axis 27-9 and a line drawn from axis 27-9 to the z-most point of the arc-degrees created by a zx-projection of surface element 27-5. Surface 27-5 has the same radius of curvature 33-20 as surface 33-5. The arc-degrees of the zx-projected 33-5 exceed the arc-degrees of the zx-projected 27-5 by the amount of arc-degrees the rocker-slider is able to rotate. In a further preferred embodiment, the arc-degrees of the zx-projected 33-5 exceed the arc-degrees of the zx-projected 27-5 by approximately ±10°. In a still further preferred embodiment, the curved surfaces 33-8 (FIG. 47) and 27-2 (FIG. 45A) can be cylindrical with the same radius of curvature whose center of curvature must fall on the turning axis 27-9. In a yet further preferred embodiment, curved surfaces 33-5 (FIG. 47) and 27-5 (FIG. 45A) can be cylindrical with the same radius of curvature whose radius falls on the turning axis 27-9.

In a further embodiment, when the rocker-slider 27-0 tilts at the maximum positive angle, planar surfaces 27-3 and 27-4 (FIG. 45A) of the rocker-slider rest on planar surfaces 33-7 and 33-6 of platform 33-2 (FIG. 47) in the most positive x-direction, i.e., the front. When tilted at the maximum negative angle the corresponding surfaces on the less positive x side of the rocker-slider and platform coincide. Planar surface 33-3 (FIG. 46) tilts at an angle to the z-axis dictated by the maximum rotation of the axial spring, in this case, −10° for the rear plane (less positive x) and 10° for the front plane (more positive x). The angles of surfaces 33-4 and 33-6 to the horizontal equal the maximum sagittal rotation permitted, but with opposite sign. Planar surfaces 33-3, 33-4 and opposite side planar surfaces 33-6, 33-7 serve as joint stops for sagittal rotation. Further, planar surface 33-4 and cylindrical surface 33-5 oppose forces and moments of forces attempting dislocate sagittal cylindrical joint elements 33-0 and 27-0. In this embodiment, these structures constitute part of the interlocking kinematic chain holding the FSU together throughout its workspace.

Alternative embodiments can utilize the mechanical programmability of the rocker-slider elements 27-0 and 28-0 by altering the arc surfaces. For example, in certain embodiments, it can be preferable for one or both rocker-sliders 27-0 and 28-0 to have a greater or lesser degree of rotation. To accomplish this, the curved surfaces 27-5 and 28-5 (FIG. 45A) can have greater arc-degree angles, resulting in larger arc surfaces, but retaining the angles of surfaces 27-3, 27-4, and 27-6 that correspond to angles 33-4, 33-6 and 33-7. This increased arc-degree angle can provide less movement relative to planar surface 33-5, but still permits planar surfaces 27-3 and 27-4, and 27-6 (FIG. 45A) of the rocker-slider to rest on planar surfaces 33-4, 33-6 and 33-7 of platform 33-2 (FIG. 47) in the most positive x-direction, i.e., the front. Similarly, the equivalent back surfaces can also be augmented as described to alter their degree of rotation as well.

In still further embodiments, the surface 32-11 and 33-11 can be filleted to eliminate a sharp biting edge as the upper and lower cylindrical joint platforms move relative to one another during normal spinal motion.

IV. Right-Circular Cylindrical Embodiment of the Cylindrical-Joint and Rocker-Slider Spinal Disc Prostheses:

A person with skill in the art will recognize that the embodiments shown in FIGS. 30, 40 and 41 can comprise other than the illustrated rectangular forms. For example, an alternative embodiment utilizes a cylindrical form, as shown in FIGS. 52 through 56. Alternative embodiments can utilized a variety of ovoid or circular shapes and forms as well. External dimensions and shapes, dictated by applications of the devices, can be important in so much as they affect the size of the overall joint cavity in the joint-platform and how they fit into the FSU. However, in preferred embodiments, the joint surfaces in the joint platform cavity conform, as described previously, to preserve proper joint operation about and along the sagittal and lateral axes.

Figure 54:
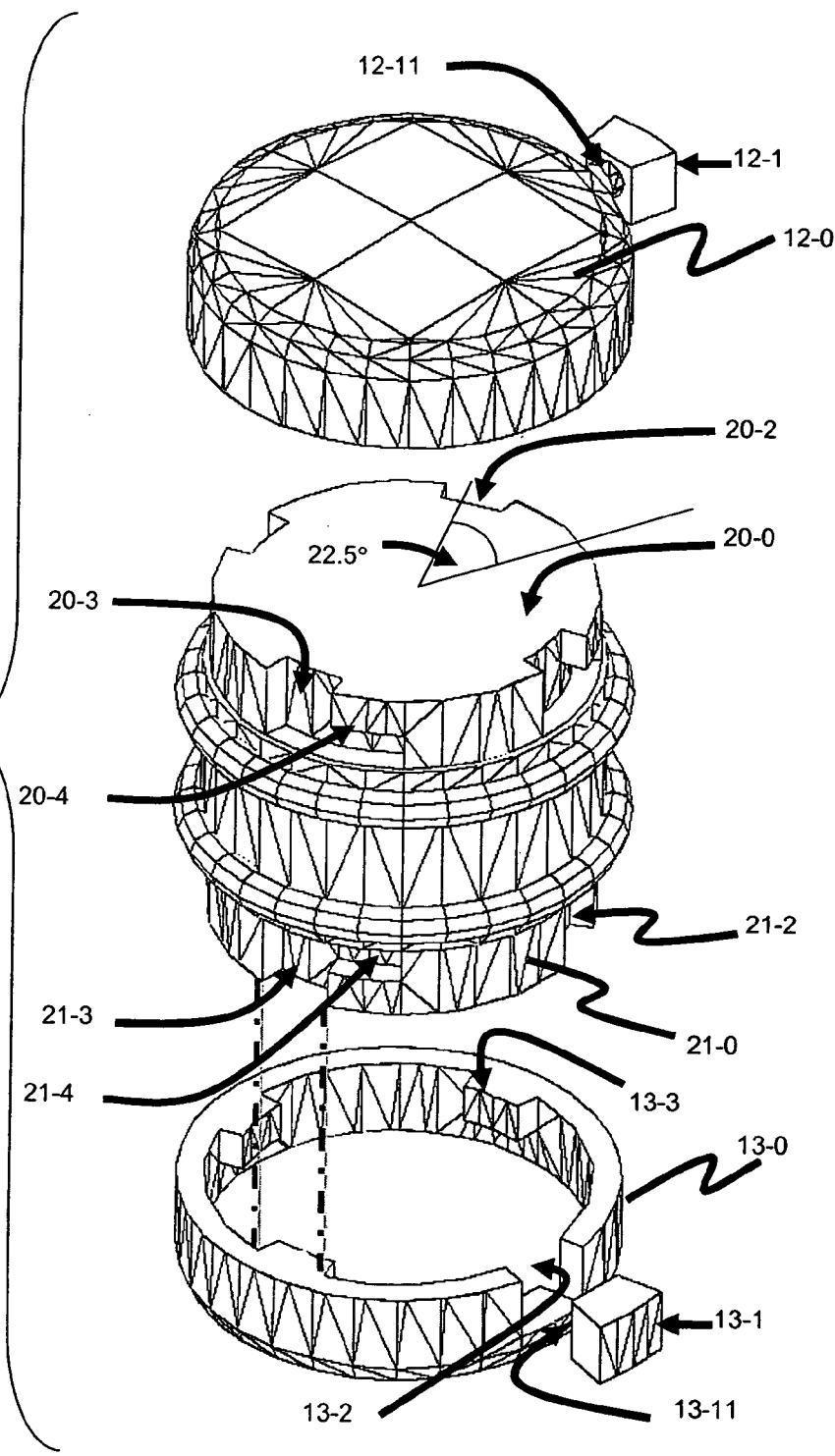
FIG. 54 illustrates the locking features of the prosthesis. To lock the prosthesis to the vertebral caps, place the prosthesis module between them and close them down onto the lateral and sagittal cylindrical-joint platforms and then twist clockwise to latch the prosthesis simultaneously to the top and bottom vertebral plates. Next, insert the locking keys into the gap provide.
Figure 55:
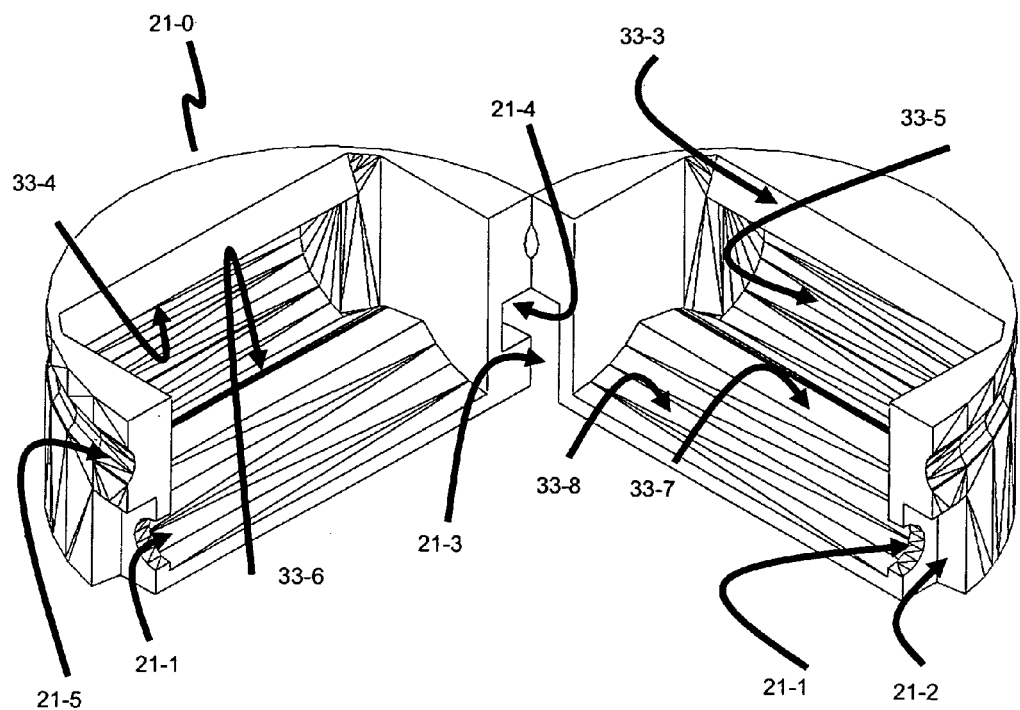
FIG. 55 shows the left and right halves of a cylindrical joint platform. The rocker-slider joint surfaces remain the same as before. In front of the element a means is provided for locking the platform to a vertebral plate by pressure fitting or bonding a plug that blocks relative rotation between a platform and vertebral plate. For assembly purposes, the cylindrical joint platforms can be formed in halves that bond or fix together. In such cases hole-and-peg techniques can be used to strengthen the bond.

In a preferred cylindrical-joint embodiment, the prostheses can slide tongue-in-groove into vertebral caps similarly, for example, as shown in FIG. 42 for the rectangular embodiment. In addition, further embodiments can utilize devices or techniques known to those with skill in the art for simultaneously affixing the device between vertebral plates. For example, the device can utilize opposable threads at each end of the device, or opposable clamps or fittings such that, when positioned between the vertebral plates, the devices of the subject invention can be twisted or turned in one direction to connect each end of the device with a vertebral plate. In a preferred embodiment, the prosthesis comprises opposable threads on each end of the device, such that it can be twisted into the vertebral caps, for example as shown in FIG. 54. In this embodiment, the cylindrical-joint prosthesis can be positioned by twisting or screwing into the superior and inferior vertebral plates 12-0 and 13-0 connected to the respective vertebra. In yet another preferred embodiment, the superior and inferior vertebral plates also possess an opposite screw sense, such that twisting or turning in a single direction connects the cylindrical-joint prosthesis to both vertebral plates simultaneously. This enables easier installation and replacement of the prosthetic device if necessary.

A further alternative embodiment, shown in FIG. 54, allows the prosthesis to be locked to the vertebral caps to rigidly fix them to those plates which can allow efficient transfer of vertebral motion of the FSU directly to the lateral and sagittal cylindrical joint platforms 20-0 and 21-0 that mate with the vertebral caps.

A further embodiment shown in FIG. 52 can utilize a strong, fiber reinforced, flexible boot 16-0 clamped to joint platforms 21-0 and 20-0 by means of clamps 15-0 and 14-0. Ring clamp 15-0 fits firmly into indent 21-5 on 21-0 and ring clamp 14-0 fits in a similar indent on 20-0 to provide, along with the boot, an effective liquid and gas seal.

Still further alternative embodiments can utilize orthogonally positioned cylindrical joint mechanisms that provide torque rotation, as well as translational movements along their axes to provide lateral as well as sagittal movement. Additional cylindrical joint(s) provide axial compression, extension and torque rotation.

Figure 56:
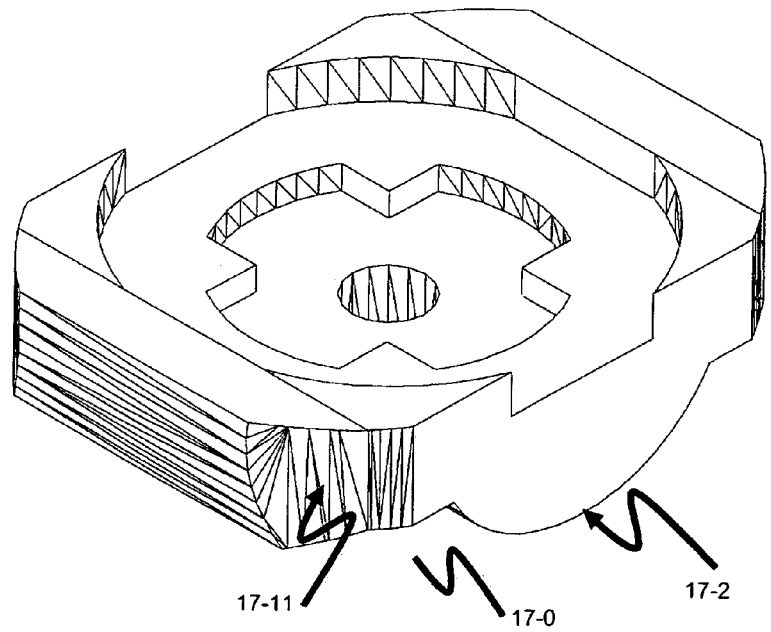
FIG. 56 illustrates the rocker-slider mechanism for this embodiment. The axial spring remains the same as shown in FIG. 45.

In a preferred embodiment, the right-circular-cylindrical prosthesis (FIG. 52) employs an internal mechanism with the same axial spring as the embodiment shown in FIG. 41, but with a modified rocker-slider 17-0, as shown, for example, in FIG. 56. In this embodiment, the rocker-slider has a clipped edge 17-11 that provides greater thickness to the prosthesis wall at the extreme linear line of travel of the rocker-slider in its channel. The cylindrical surface 17-2 matches that of the channel to form a lower kinematic pair joint. In a further embodiment, the internal surfaces, for example as shown in FIG. 25, of the lateral and sagittal cylindrical joint platforms 20-0, 21-0 correspond to the cylindrical joint platforms of the embodiment shown in FIG. 41. However, in this embodiment, these surfaces are "packaged" into a right-circular cylinder arrangement. For convenience, the same reference numbers are assigned to these surfaces to establish the direct relationship to the previous surfaces of FIGS. 46 and 47. In a still further embodiment, for assembly purposes, the cylindrical joint platforms 20-0, 21-0 can be halved, but orthogonal to the cut shown in FIG. 55 which can maintain structural integrity.

The vertebral caps 12-0 and 13-0 can be joined by a variety of methods known to those with skill in the art. In one embodiment, the vertebral caps 12-0, 13-0 and their corresponding cylindrical joint platforms 20-0, 21-0 latch together as shown, for example, in FIG. 54. In this embodiment, one or more tongues 13-3, preferably three tongues, within the vertebral cap 13-0 are aligned with one or more, preferably three, slots 21-3 on the cylindrical joint platform 21-0. This action can align slots 20-3 to the tongues on vertebral cap 12-0 (not shown in FIG. 54). To secure, the caps can be firmly pressed down onto the two cylindrical joint platforms 20-0, 21-0, keeping tongues and slots aligned, and the entire prosthesis twisted either clockwise, looking down onto the device from above, with respect to the vertebral caps 12-0, 13-0 to lock the platforms to their respective vertebral caps as the tongues 13-3 slide into slots 21-4 and the tongues on 12-0 simultaneously slide into slots 20-4. A counterclockwise twist lock version is also possible. In a preferred embodiment, the entire prosthesis is twisted approximately 22.5° in a clockwise direction, with respect to the vertebral caps. This causes three tongues 13-3 to fit into the three corresponding slots 20-4 and tongues on 12-0 to fit into three corresponding slots 21-4 to form a sufficiently tight hold there between. In a further embodiment, a hole 21-1 and an indent 21-2 in the sagittal cylindrical joint platform 21-0 (FIG. 55) can now align with the gap 13-2 (FIG. 54) of the vertebral cap 13-0. Correspondingly, gap 20-2 on platform 20-0 can align with a similar gap on the vertebral cap 12-0. In a still further embodiment, a plug 13-1, or similar device, is positioned, for example by press fitting, or otherwise bonded, into the gaps 13-2 and 21-2 with post 13-11 (same structure as 12-11, but not seen in FIG. 54). This fixes the vertebral cap 13-0 to the sagittal cylindrical joint platform 21-0, especially with respect to rotation, and, in a preferred embodiment, faces anterior and is centered. In a further preferred embodiment, plug 13-1, after insertion into vertebral cap 12-0 and the lateral cylindrical joint platform 20-0, can be oriented at right angles to the other plug, namely, on the left-lateral side of the prosthesis, and fixes the vertebral cap 12-0 to the lateral cylindrical joint platform 20-0, especially with respect to rotation.

Figure 53:
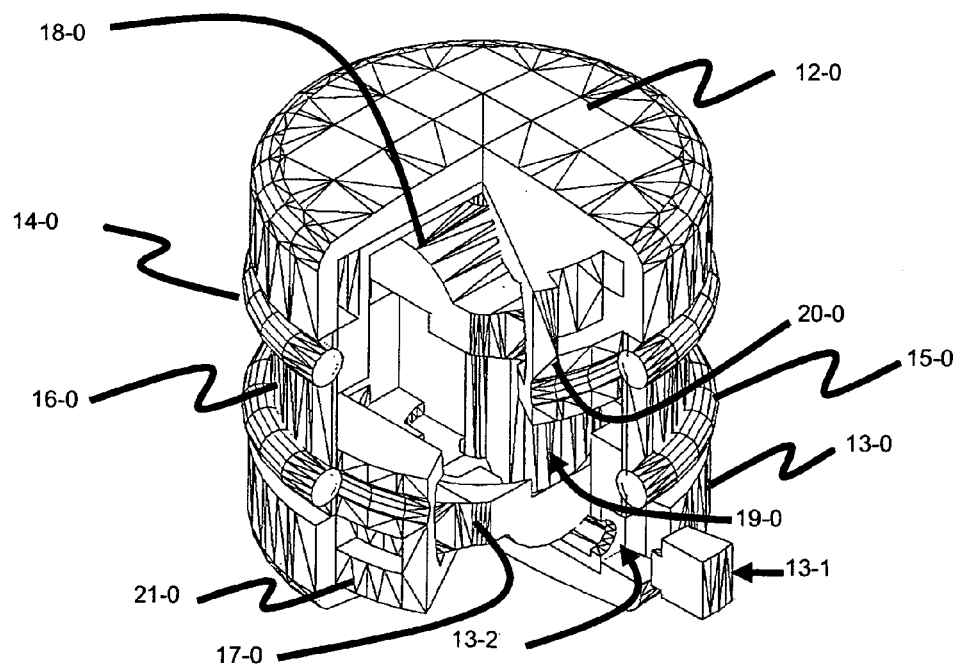
FIG. 53 illustrates a cutaway view of FIG. 41.

In a preferred embodiment, the axial cylindrical joint for the cylindrical embodiment, shown in, for example, FIG. 54, is the axial spring 19-0 (FIG. 53). In a further preferred embodiment, a cross pattern projection on the top of the spring, similar to, for example, cross-pattern 29-2, is the distal link and rigidly connects to rocker-slider 18-0 in a mating indent. In a still further preferred embodiment, a cross pattern on the bottom of the spring, similar to, for example, cross-pattern 29-2, is the proximal link and rigidly inserts into rocker-slider 17-0, mating with a cross pattern indent, similar to, for example, cross pattern 27-7.

In a further preferred embodiment, the lateral cylindrical joint for this embodiment consists of the lateral rocker-slider 18-0 and the lateral cylindrical joint platform 20-0. The axis of rotation of the joint corresponds to the axis of the half-right circular cylinder surface on the bottom of the rocker-slider. In this embodiment, there is no joint shaft per se. The rocker-slider constitutes the proximal link for the lateral cylindrical joint and the platform 20-0 the distal link. The lateral joint axis is orthogonal to the sagittal joint axis, as before.

In a still further preferred embodiment, the sagittal cylindrical joint for this embodiment consists of the sagittal rocker-slider 17-0 and the sagittal cylindrical joint platform 21-0. The axis of rotation of the joint corresponds to the axis of the half-right circular cylinder surface on the bottom of the rocker-slider. There is no joint shaft per se. The rocker-slider constitutes the distal link for the sagittal cylindrical joint and the platform 21-0 the proximal link. The sagittal joint axis is orthogonal to the lateral joint axis, as before.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A prosthetic device for approximating spinal disc movement wherein said device can be implanted in the spine and engaged between a first and second vertebrae, such that when said device is implanted in the spine and engaged with a first and second vertebra, said device forms an interlocking kinematic chain between said first and second vertebra, wherein said kinematic chain comprises:
   an axial spring;
   a lateral sleeve attached to one end of said axial spring;
   a lateral rod disposed within said lateral sleeve;
   a lateral cylindrical joint platform in which said lateral sleeve is movably engaged and said lateral rod is positioned, such that said lateral sleeve can slide along the lateral rod and rotate about the lateral rod within the lateral cylindrical joint platform;
   a sagittal sleeve attached to the opposite end of the axial spring;
   a sagittal rod disposed within said sagittal sleeve; and
   a sagittal cylindrical joint platform in which said sagittal sleeve is movably engaged and said sagittal rod is fixedly positioned, such that said sagittal sleeve can slide along the sagittal rod and rotate about the sagittal rod within the sagittal cylindrical joint platform;
   such that there is provided up to three independent rotational degrees of freedom and up to three independent linear degrees of freedom.

2. The device, according to claim 1, wherein the axial spring is capable of simultaneous movement in the lateral, sagittal, and axial linear directions.

3. The device, according to claim 2, wherein the at east three linear directions are lateral, sagittal and axial.

4. The device, according to claim 1, wherein the axial spring comprises sufficient tension to permit continuous self-alignment with the axis of a functional spinal unit during flexion or extension motions.

5. The device, according to claim 1, further comprising vertebral plates, for engagement with a first and second vertebrae removably attached to the cylindrical joint platforms.

6. The device, according to claim 5, wherein said vertebral plates comprise a material selected from the group consisting of titanium, cobalt-chromium-molybdenum alloy, and titanium-carbide-coated stainless steel with a bone fusion matrix.

7. The device, according to claim 1, further comprising a boot removably connected with each of said cylindrical joint platforms, such that elements of the kinematic chain are sealed within the boot thereby preventing fluids within the device from contacting fluids external to said device.

8. The device, according to claim 7, wherein said boot comprises a strong, flexible, non-homogeneous, fiber reinforced elastomer matrix.

9. The device, according to claim 8, wherein the reinforcing fibers are located external to the elastomer matrix.

10. The device, according to claim 8, wherein said boot is capable of providing torsional load bearing.

11. The device, according to claim 8, wherein said boot is capable of providing non-linear compression and extension.

12. The device, according to claim 7, wherein said boot comprises at least one edge having a shape that removably engages with at least one channel of compatible shape and wherein said channel is positioned around the circumference of a cylindrical joint platform.

13. The device, according to claim 7, further comprising a biocompatible lubricant sealed within the boot.

14. The device, according to claim 7, further comprising one or more pass through holes that allow said biocompatible lubricant to be circulated around and through the moveable elements of the device.

15. The device, according to claim 1, wherein said lateral and sagittal cylindrical joint platforms further comprise at least one removable endplate to permit positioning of the rods and sleeves within the cylindrical joint platforms.

16. A prosthetic device for approximating spinal disc movement wherein said device can be implanted in the spine and engaged between a first and second vertebrae, such that when said device is implanted in the spine and engaged between a first and second vertebra, said device forms an interlocking kinematic chain between said first and second vertebra, wherein said interlocking kinematic chain comprises:
   an axial spring;
   a lateral sleeve, having at least one aperture therein, fixedly attached to one end of said axial spring;
   a lateral spring, disposed within said lateral sleeve, having at least one tang fixedly attached thereon and positioned within the at least one aperture of said lateral sleeve;
   a lateral cylindrical joint platform in which said lateral sleeve is movably engaged and the ends of said lateral spring are fixedly positioned, such that said lateral sleeve can slide along the lateral spring and can rotate about said lateral spring whereby said at least one tang can contact one or more sides of the at least one aperture causing torquing of the lateral spring;
   a sagittal sleeve, having at least one aperture therein, fixedly attached to the opposite end of the axial spring;
   a sagittal spring, disposed within said sagittal sleeve, having at least one tang fixedly attached thereon and positioned within the at least one aperture of said lateral sleeve; and
   a sagittal cylindrical joint platform in which said sagittal sleeve is movably engaged and the ends of said sagittal spring are fixedly positioned, such that said sagittal sleeve can slide along the sagittal spring and can rotate about said sagittal spring whereby said at least one tang can contact one or more sides of the at least one aperture causing torquing of the sagittal spring;
   such that there is provided up to three independent rotational degrees of freedom and up to three independent linear degrees of freedom.

17. The device according to claim 1, wherein the length of the device, from the end of the lateral cylindrical joint platform to the end of the sagittal cylindrical joint platform is approximately 14.0 mm.

18. The device, according to claim 1, wherein the axial spring is capable of movement in at least one linear direction.

19. The device, according to claim 1, wherein the axial spring is capable of simultaneous torsion and extension and/or compression.

20. The device, according to claim 1, wherein one or more elements of said kinematic chain comprise a material selected from the group consisting of titanium steel, titanium-carbide-coated stainless steel, polyurethane, thermoplastics, cobalt-chromium-molybdenum alloy.

21. The device, according to claim 1, wherein the axial spring is capable of movement in at least one linear direction.

22. The device, according to claim 1, wherein the axial spring is capable of simultaneous movement in at least three linear directions.

23. The device, according to claim 22, wherein the at least three linear directions are lateral, sagittal and axial.

24. The device, according to claim 16, wherein the axial, sagittal, and lateral springs are capable of simultaneous torsion and extension and/or compression.

25. The device, according to claim 24, thither comprising a boot with a biocompatible, colloidal, elastomeric suspension sealed therein, said boot being removably connected with each of said cylindrical joint platforms, such that elements of the kinematic chain are sealed within the boot thereby preventing the suspension within the boot from contacting fluids external to said device.

26. The device, according to claim 25, further comprising one or more pass through holes that allow said biocompatible lubricant to be circulated around and through the moveable elements of the device.

27. The device, according to claim 25, wherein said boot comprises a strong, flexible, non-homogeneous, fiber reinforced elastomer matrix.

28. The device, according to claim 27, wherein the reinforcing fibers are located external to the elastomer matrix.

29. The device, according to claim 25, wherein said boot comprises at least one edge having a shape that removably engages with at least one channel of compatible shape and positioned around the circumference of the interior of a cylindrical joint platform.

30. The device, according to claim 25, wherein said boot is capable of providing torsional load bearing.

31. The device, according to claim 25, wherein said boot is capable of providing non-linear compression and extension.

32. The device, according to claim 25, further comprising a biocompatible lubricant sealed within the boot.

33. The device, according to claim 24, wherein said lateral and sagittal cylindrical joint platforms further comprise at least one removable endplate to permit positioning of the rods and sleeves within the cylindrical joint platforms.

34. The device, according to claim 24, wherein one or more elements of said kinematic chain comprise a material selected from the group consisting of titanium steel, titanium-carbide-coated stainless steel, polyurethane, thermoplastics, cobalt-chromium-molybdenum alloy, and plastic.

35. The device, according to claim 24, wherein the lateral, and sagittal springs comprise sufficient tension to resist longitudinal bending and permit continuous self-alignment along their central axis.

36. The device, according to claim 24, wherein the axial spring comprises sufficient tension to permit continuous self-alignment with the axis of a functional spinal unit after flexion or extension motions.

37. The device, according to claim 24, further comprising vertebral plates, for engagement with a first and second vertebrae, removably attached to the cylindrical joint platforms.

38. The device, according to claim 37, wherein said vertebral plates comprise a material selected from the group consisting of titanium, cobalt-chromium-molybdenum alloy, and titanium-carbide-coated stainless steel with a bone fusion matrix.

39. A prosthetic device for approximating spinal disc movement wherein said device can be implanted in the spine between a first and second vertebrae, such that when said device is implanted in the spine and engaged with a first and second vertebra, said device forms an interlocking kinematic chain between said first and second vertebra, wherein said interlocking kinematic chain comprises:

an axial spring;

a lateral rocker-slider fixedly attached to one end of said axial spring, wherein the lateral rocker-slider comprises a first joint shaft slidably disposed within a first sleeve;

a lateral cylindrical joint platform in which said lateral rocker-slider is movably attached within a lateral joint axis such that the lateral rocker-slider sleeve can slide along the lateral joint axis and rotate or rock about the lateral joint axis;

a sagittal rocker-slider fixedly attached to the opposite end of the axial spring, wherein the sagittal rocker slider comprises a second joint shaft slidably disposed within a second sleeve;

a sagittal cylindrical joint platform in which said sagittal rocker-slider is movably attached within a sagittal joint axis such that the sagittal rocker-slider sleeve can slide along the sagittal joint axis and rotate or rock about the sagittal joint axis;

such that there is provided up to three independent rotational degrees of freedom and up to three independent linear degrees of freedom.

40. The device, according to claim 39, wherein a joint shaft comprises one or more springs positioned along the lateral and/or sagittal joint axes to oppose and/or dampen the motion of the lateral and/or sagittal rocker slider.

41. The device, according to claim 39, further comprising vertebral plates, for engagement with a first and second vertebrae, removably attached to the cylindrical joint platforms.

42. The device, according to claim 41, wherein said vertebral plates comprise a material selected from the group consisting of titanium, cobalt-chromium-molybdenum alloy, and titanium-carbide-coated stainless steel with a bone fusion matrix.

43. The device, according to claim 41, further comprising a circumferential shape selected from the group consisting of squared, rectangular, circular, and ovoid.

44. The device, according to claim 43, wherein said circumferential shape is circular.

45. The device, according to claim 39, further comprising a boot removably connected with each of said cylindrical joint platforms, such that elements of the kinematic chain are sealed within the boot thereby preventing fluids within the device from contacting fluids external to said device.

46. The device, according to claim 45, wherein said boot comprises a strong, flexible, non-homogeneous, fiber reinforced elastomer matrix.

47. The device, according to claim 46, wherein the reinforcing fibers are located external to the elastomer matrix.

48. The device, according to claim 45, wherein said boot comprises at least one edge having a shape that removably engages with at least one channel of compatible shape and positioned around the circumference of the interior of a cylindrical joint platform.

49. The device, according to claim 45, wherein said boot is capable of providing torsional load bearing.

50. The device, according to claim 45, wherein said boot is capable of providing non-linear compression and extension.

51. The device, according to claim 45, further comprising a biocompatible lubricant sealed within the boot.

52. The device, according to claim 39, further comprising a boot with a biocompatible colloidal elastomeric suspension sealed therein.

53. The device, according to claim 52, further comprising one or more pass through holes that allow said biocompatible suspension to be circulated around and through the moveable elements of the device.

54. The device, according to claim 39, wherein said lateral and sagittal cylindrical joint platforms further comprise at least one removable end brace to permit positioning of rocker-sliders within the cylindrical joint platforms.

55. The device, according to claim 41, further comprising opposable threads on the vertebral plates that are compatible with opposable threads on the cylindrical joint platforms such that the device can be positioned between the vertebral plates and twisted or turned in one direction to secure the device simultaneously between two vertebral plates.

56. The device, according to claim 39, wherein the axial spring is capable of movement in at least one linear direction.

57. The device, according to claim 39, wherein the axial spring is capable of simultaneous movement in at least three linear directions.

58. The device, according to claim 57, wherein the at least three linear directions are lateral, sagittal and axial.

59. The device, according to claim 39, wherein the lateral and sagittal rocker-slider elements comprise springs having sufficient tension to resist longitudinal bending and permit continuous self-alignment along their central axis.

60. The device, according to claim 39, wherein the axial spring comprises sufficient tension to permit continuous self-alignment with the axis of a functional spinal unit after flexion or extension motions.

61. The device, according to claim 39, wherein the axial spring is capable of simultaneous torsion and extension and/or compression.

62. The device, according to claim 39, wherein one or more elements of said kinematic chain comprise a material selected from the group consisting of titanium steel, titanium-carbide-coated stainless steel, polyurethane, thermoplastics, cobalt-chromium-molybdenum alloy, and plastics.

63. The device, according to claim 39, wherein a joint shaft comprises a rod.

64. A method for approximating spinal disc movement utilizing a device comprising:

an axial spring;

a lateral rocker-slider fixedly attached to one end of said axial spring, wherein the lateral rocker-slider comprises a first joint shaft slidably disposed within a first sleeve;

a lateral cylindrical joint platform in which said lateral rocker-slider is movably attached within a lateral joint axis such that the lateral rocker-slider sleeve can slide along the lateral joint axis and rotate or rock about the lateral joint axis;

a sagittal rocker-slider fixedly attached to the opposite end of the axial spring, wherein he sagittal rocker-slider comprises a second joint shaft slidably disposed within a first sleeve;

a sagittal cylindrical joint platform in which said sagittal rocker-slider is movably attached within a sagittal joint axis such that the sagittal rocker-slider sleeve can slide along the sagittal joint axis and rotate or rock about the sagittal joint axis;

said method comprising implanting the device between a first and second vertebrae, such that with said device engaged between the first and second vertebrae, there is formed a kinematic chain between the first and second vertebrae, such that there is provided at least one and up to three independent rotational degrees of freedom and at least one and up to three independent linear degrees of freedom.

* * * * *

UNITED STATES PATENT AND TRADEMARK OFFICE
CERTIFICATE OF CORRECTION

PATENT NO.         : 7,799,080 B2
APPLICATION NO.    : 11/540620
DATED              : September 21, 2010
INVENTOR(S)        : Keith L. Doty Page 1 of 1

It is certified that error appears in the above-identified patent and that said Letters Patent is hereby corrected as shown below:

<u>Column 52,</u>
Line 40, "at east three" should read --at least three--.

<u>Column 54,</u>
Line 1, "according to claim 1" should read --according to claim 16--.
Line 11, "according to claim 24, thither" should read --according to claim 16, further--.
Line 38, "according to claim 24" should read --according to claim 16--.
Line 42, "according to claim 24" should read --according to claim 16--.
Line 47, "according to claim 24" should read --according to claim 16--.
Line 51, "according to claim 24" should read --according to claim 16--.
Line 55, "according to claim 24" should read --according to claim 16--.

Signed and Sealed this
First Day of February, 2011

David J. Kappos
*Director of the United States Patent and Trademark Office*